(12) United States Patent
Yu et al.

(10) Patent No.: US 11,939,386 B2
(45) Date of Patent: Mar. 26, 2024

(54) AXL-TARGETING ANTIBODY, ANTIBODY-DRUG CONJUGATE, PREPARATION METHOD THEREFOR, AND USE THEREOF

(71) Applicants: FUDAN UNIVERSITY, Shanghai (CN); SHANGHAI INSTITUTE OF MATERIA MEDICA, CHINESE ACADEMY OF SCIENCES, Shanghai (CN)

(72) Inventors: Ke Yu, Shanghai (CN); Jingkang Shen, Shanghai (CN); Tao Meng, Shanghai (CN); Jinpeng Pei, Shanghai (CN); Lanping Ma, Shanghai (CN); Xin Wang, Shanghai (CN); Rui Jin, Shanghai (CN); Zhiyan Du, Shanghai (CN); Lin Chen, Shanghai (CN); Ting Yu, Shanghai (CN); Yongliang Zhang, Shanghai (CN)

(73) Assignee: Shanghai Institute of Materia Medica, Chinese Academy of Sciences, Shanghai (CN)

(*) Notice: Subject to any disclaimer, the term of this patent is extended or adjusted under 35 U.S.C. 154(b) by 700 days.

(21) Appl. No.: 17/055,499

(22) PCT Filed: May 10, 2019

(86) PCT No.: PCT/CN2019/086475
§ 371 (c)(1),
(2) Date: Nov. 13, 2020

(87) PCT Pub. No.: WO2019/218944
PCT Pub. Date: Nov. 21, 2019

(65) Prior Publication Data
US 2021/0214447 A1 Jul. 15, 2021

(30) Foreign Application Priority Data
May 15, 2018 (CN) .......................... 201810464287.1

(51) Int. Cl.
| C07K 16/28 | (2006.01) |
| A61K 39/00 | (2006.01) |
| A61K 45/06 | (2006.01) |
| A61K 47/68 | (2017.01) |
| A61P 35/00 | (2006.01) |
| C12N 5/078 | (2010.01) |

(52) U.S. Cl.
CPC .......... *C07K 16/2863* (2013.01); *A61K 45/06* (2013.01); *A61K 47/6803* (2017.08); *A61K 47/6817* (2017.08); *A61K 47/6849* (2017.08); *A61P 35/00* (2018.01); *C12N 5/0634* (2013.01); *A61K 2039/505* (2013.01)

(58) Field of Classification Search
CPC ............ C07K 16/2863; C07K 2317/24; C07K 2317/33; C07K 2317/77; C07K 2317/92; C07K 2317/565; C07K 2317/622; A61K 45/06; A61K 47/6803; A61K 47/6817; A61K 47/6849; A61K 2039/505; A61K 47/6877; A61K 47/6889; A61K 47/6801; A61P 35/00; C12N 5/0634; G01N 2333/91205; G01N 33/573; G01N 33/6854

See application file for complete search history.

(56) References Cited

U.S. PATENT DOCUMENTS

2012/0121587 A1* 5/2012 Maeda ................ C07K 16/303
424/174.1

FOREIGN PATENT DOCUMENTS

| CN | 107074948 A | 8/2017 |
| WO | 2014/068139 A1 | 5/2014 |
| WO | 2014/174111 A1 | 10/2014 |
| WO | 2016/091891 A1 | 6/2016 |
| WO | 2016/166296 A2 | 10/2016 |
| WO | 2016/187354 A1 | 11/2016 |
| WO | 2017/009258 A1 | 1/2017 |
| WO | 2017/180842 A1 | 10/2017 |
| WO | 2017/220695 A1 | 12/2017 |

OTHER PUBLICATIONS

Edwards et al, J Mol Biol 334:103-118 (2003) (Year: 2003).*
Marchalonis et al., Dev & Comp Immunol 30:223-247 (2006) (Year: 3006).*
Almagro & Fransson, Frontiers in Bioscience 2008; 13:1619-33 (Year: 2008).*
Sela-Culang Front. Immunol. 4(302) (2013) (Year: 2013).*
Li et al., "Repertoire diversification in mice with an IgH-locus-targeted transgene for the rearranged VH domain of a physiologically selected anti-ssDNA antibody," *Molecular Immunology* 42:1475-1484 (2005).

(Continued)

*Primary Examiner* — Julie Wu
*Assistant Examiner* — John L Van Druff
(74) *Attorney, Agent, or Firm* — Seed IP Law Group LLP

(57) ABSTRACT

Disclosed are a new AXL-targeting monoclonal antibody and antibody-drug conjugate. Also disclosed is a method for preparing said antibody and antibody-drug conjugate. The AXL antibody of the present invention can bind with purified human AXL protein and multiple AXL on tumor cell surface with high effectiveness and high specificity. Said humanized antibody also has high affinity and low immunogenicity. Said AXL antibody-drug conjugate has markable performance against tumors having high AXL expression.

15 Claims, 24 Drawing Sheets
Specification includes a Sequence Listing.

(56) References Cited

OTHER PUBLICATIONS

Roark et al., "Breakdown of B Cell Tolerance in a Mouse Model of Systemic Lupus Erythematosus," *J. Exp. Med. 181*: 1157-1167 (Mar. 1995).
Supplemental European Search Report for EP 19 80 3867, 13 pages, dated Jan. 26, 2022.
Wei et al., "A novel AXL chimeric antigen receptor endows T cells with anti-tumor effects against triple negative breast cancers," *Cellular Immunology 331*:49-58 (2018).

* cited by examiner

Breast cancer: AXL mRNA

| MDA-MB-453 (n= 3 tests) | Cell proliferation rate $IC_{50} \pm SD(nM)$ |
|---|---|
| mAb002c-vc-MMAE | >10 |
| mAb002c-BL20-MMAE | >10 |
| AXL107-vc-MMAE | >10 |
| AXL107-BL20-MMAE | >10 |

| MDA-MB-231 (n= 4 tests) | Cell proliferation rate $IC_{50} \pm SD(nM)$ |
|---|---|
| mAb002c-vc-MMAE | 0.0596±0.0112 |
| mAb002c-BL20-MMAE | 0.0391±0.0051 |
| AXL107-vc-MMAE | 0.0912±0.0274 |
| AXL107-BL20-MMAE | 0.0840±0.0256 |

MDA-MB-231

| MDA-MB-231 | Cell proliferation rate IC$_{50}$±SD (nM) |
|---|---|
| Hu002-1-BL20-MMAE | 0.0368±0.0046 |
| Hu002-2-BL20-MMAE | 0.0424±0.0038 |
| Hu002-4-BL20-MMAE | 0.0361±0.0002 |
| Hu002-5-BL20-MMAE | 0.0598±0.0110 |
| Hu002-7-BL20-MMAE | 0.0368±0.0027 |
| Hu002-16-BL20-MMAE | 0.0660±0.0046 |

Hs578T

| Hs578T | Cell proliferation rate IC$_{50}$±SD (nM) |
|---|---|
| Hu002-1-BL20-MMAE | 0.0172±0.0018 |
| Hu002-2-BL20-MMAE | 0.0130±0.0115 |
| Hu002-4-BL20-MMAE | 0.0165±0.0012 |
| Hu002-5-BL20-MMAE | 0.0151±0.0013 |
| Hu002-7-BL20-MMAE | 0.0139±0.0018 |
| Hu002-16-BL20-MMAE | 0.0229±0.0075 |

U87MG

| U87MG | Cell proliferation rate $IC_{50} \pm SD$ (nM) |
|---|---|
| Hu002-1-BL20-MMAE | 0.0450±0.0124 |
| Hu002-2-BL20-MMAE | 0.0453±0.0067 |
| Hu002-4-BL20-MMAE | 0.0445±0.0074 |
| Hu002-5-BL20-MMAE | 0.0440±0.0169 |
| Hu002-7-BL20-MMAE | 0.0332±0.0050 |
| Hu002-16-BL20-MMAE | 0.0413±0.0013 |

LCLC-103H

| LCLC-103H | Cell proliferation rate $IC_{50} \pm SD$ (nM) |
|---|---|
| Hu002-1-BL20-MMAE | 0.0302±0.0011 |
| Hu002-2-BL20-MMAE | 0.0281±0.0019 |
| Hu002-4-BL20-MMAE | 0.03103±0.0008 |
| Hu002-5-BL20-MMAE | 0.0334±0.0028 |
| Hu002-7-BL20-MMAE | 0.0304±0.0016 |
| Hu002-16-BL20-MMAE | 0.0408±0.0052 |

*In vivo* anti-tumor model (LCLC-103H)

HEK293T-transiently transfected and expressed murine AXL

A

HEK293T-transiently transfected and expressed cynomolgus monkey AXL

Western blot primary antibody: Hu002-2

B

SEQUENCE LISTING

```
<160> NUMBER OF SEQ ID NOS: 38

<210> SEQ ID NO 1
<211> LENGTH: 5
<212> TYPE: PRT
<213> ORGANISM: Artificial Sequence
<220> FEATURE:
<223> OTHER INFORMATION: mAb002 HCDR1

<400> SEQUENCE: 1

Asp Phe Tyr Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: mAb002 HCDR2
```

```
<400> SEQUENCE: 2

Trp Ile Tyr Pro Gly Ser Gly Asn Thr Lys Tyr Asn Glu Lys Phe Lys
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: mAb002 HCDR3

<400> SEQUENCE: 3

Ser Thr Gly Phe Phe Asp Tyr
1               5

<210> SEQ ID NO 4
<211> LENGTH: 10
<212> TYPE: PRT
<213> ORGANISM: Artificial Sequence
<220> FEATURE:
<223> OTHER INFORMATION: mAb002 LCDR1

<400> SEQUENCE: 4

Ser Ala Ser Ser Ser Ile Gly Tyr Met Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: mAb002 LCDR2

<400> SEQUENCE: 5

Leu Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: mAb002 LCDR3

<400> SEQUENCE: 6

Gln Gln Trp Ser Ser Asn Pro Pro Thr
1               5

<210> SEQ ID NO 7
<211> LENGTH: 116
<212> TYPE: PRT
<213> ORGANISM: Artificial Sequence
<220> FEATURE:
<223> OTHER INFORMATION: mAb002-VH

<400> SEQUENCE: 7

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Pro Phe Thr Asp Phe
                20                  25                  30

Tyr Ile Asn Trp Val Lys Gln Lys Pro Gly Gln Gly Leu Glu Trp Ile
            35                  40                  45

Gly Trp Ile Tyr Pro Gly Ser Gly Asn Thr Lys Tyr Asn Glu Lys Phe
```

```
                    50                  55                  60
Lys Gly Lys Ala Thr Leu Thr Val Asp Thr Ser Ser Thr Ala Tyr
 65                  70                  75                  80

Met Gln Leu Ser Ser Leu Thr Ser Glu Asp Thr Ala Val Tyr Phe Cys
                 85                  90                  95

Ala Arg Ser Thr Gly Phe Phe Asp Tyr Trp Gly Gln Gly Thr Thr Leu
                100                 105                 110

Thr Val Ser Ser
        115

<210> SEQ ID NO 8
<211> LENGTH: 106
<212> TYPE: PRT
<213> ORGANISM: Artificial Sequence
<220> FEATURE:
<223> OTHER INFORMATION: mAb002-VL

<400> SEQUENCE: 8

Gln Ile Val Leu Thr Gln Ser Pro Ala Leu Met Ser Ala Ser Pro Gly
 1               5                  10                  15

Glu Lys Val Thr Met Thr Cys Ser Ala Ser Ser Ser Ile Gly Tyr Met
                 20                  25                  30

Tyr Trp Tyr Gln Gln Lys Pro Arg Ser Ser Pro Lys Ser Trp Ile Tyr
                 35                  40                  45

Leu Thr Ser Asn Leu Ala Ser Gly Val Pro Ala Arg Phe Ser Gly Ser
         50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Pro Thr
                 85                  90                  95

Phe Gly Ala Gly Thr Lys Leu Glu Leu Lys
                100                 105

<210> SEQ ID NO 9
<211> LENGTH: 5
<212> TYPE: PRT
<213> ORGANISM: Artificial Sequence
<220> FEATURE:
<223> OTHER INFORMATION: mAb005 HCDR1

<400> SEQUENCE: 9

Ser Tyr Tyr Ile His
 1               5

<210> SEQ ID NO 10
<211> LENGTH: 17
<212> TYPE: PRT
<213> ORGANISM: Artificial Sequence
<220> FEATURE:
<223> OTHER INFORMATION: mAb005 HCDR2

<400> SEQUENCE: 10

Trp Ile Tyr Pro Gly Ser Asp Asn Thr Lys Tyr Asn Glu Lys Phe Lys
 1               5                  10                  15

Asp

<210> SEQ ID NO 11
<211> LENGTH: 13
<212> TYPE: PRT
<213> ORGANISM: Artificial Sequence
<220> FEATURE:
```

```
<223> OTHER INFORMATION: mAb005 HCDR3

<400> SEQUENCE: 11

Asn Tyr Tyr Asp Tyr Asp Gly Gly Thr Trp Phe Pro Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: mAb005 LCDR1

<400> SEQUENCE: 12

Arg Ala Ser Gln Asp Ile Asn Tyr Tyr Leu Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: mAb005 LCDR2

<400> SEQUENCE: 13

Tyr Thr Ser Arg Leu His Ser
1               5

<210> SEQ ID NO 14
<211> LENGTH: 9
<212> TYPE: PRT
<213> ORGANISM: Artificial Sequence
<220> FEATURE:
<223> OTHER INFORMATION: mAb005 LCDR3

<400> SEQUENCE: 14

Gln Gln Gly Asn Thr Leu Pro Trp Thr
1               5

<210> SEQ ID NO 15
<211> LENGTH: 122
<212> TYPE: PRT
<213> ORGANISM: Artificial Sequence
<220> FEATURE:
<223> OTHER INFORMATION: mAb005-VH

<400> SEQUENCE: 15

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Tyr Ile His Trp Val Gln Arg Pro Gly Gln Gly Leu Glu Trp Ile
        35                  40                  45

Gly Trp Ile Tyr Pro Gly Ser Asp Asn Thr Lys Tyr Asn Glu Lys Phe
    50                  55                  60

Lys Asp Lys Ala Thr Leu Thr Ala Asp Thr Ser Ser Gly Thr Ala Tyr
65                  70                  75                  80

Met Gln Leu Ser Ser Leu Thr Ser Asp Asp Ser Ala Val Phe Tyr Cys
                85                  90                  95

Ala Arg Asn Tyr Tyr Asp Tyr Asp Gly Gly Thr Trp Phe Pro Tyr Trp
            100                 105                 110

Gly Gln Gly Thr Leu Val Thr Val Ser Ala
        115                 120
```

<210> SEQ ID NO 16
<211> LENGTH: 107
<212> TYPE: PRT
<213> ORGANISM: Artificial Sequence
<220> FEATURE:
<223> OTHER INFORMATION: mAb005-VL

<400> SEQUENCE: 16

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Tyr Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Arg Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 17
<211> LENGTH: 5
<212> TYPE: PRT
<213> ORGANISM: Artificial Sequence
<220> FEATURE:
<223> OTHER INFORMATION: mAb001 HCDR1

<400> SEQUENCE: 17

```
Ser Gly Tyr Trp Ser
1               5
```

<210> SEQ ID NO 18
<211> LENGTH: 16
<212> TYPE: PRT
<213> ORGANISM: Artificial Sequence
<220> FEATURE:
<223> OTHER INFORMATION: mAb001 HCDR2

<400> SEQUENCE: 18

```
Tyr Met Thr Tyr Ser Gly Ala Thr Tyr Tyr Asn Pro Ser Leu Lys Ser
1               5                   10                  15
```

<210> SEQ ID NO 19
<211> LENGTH: 9
<212> TYPE: PRT
<213> ORGANISM: Artificial Sequence
<220> FEATURE:
<223> OTHER INFORMATION: mAb001 HCDR3

<400> SEQUENCE: 19

```
Gly Gly Asn Ser Tyr Phe Phe Asp Tyr
1               5
```

<210> SEQ ID NO 20
<211> LENGTH: 11
<212> TYPE: PRT
<213> ORGANISM: Artificial Sequence
<220> FEATURE:
<223> OTHER INFORMATION: mAb001 LCDR1

```
<400> SEQUENCE: 20

Arg Ala Ser Glu Asn Ile Tyr Ser Asn Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: mAb001 LCDR2

<400> SEQUENCE: 21

Ala Ala Thr Asn Leu Ala Asp
1               5

<210> SEQ ID NO 22
<211> LENGTH: 9
<212> TYPE: PRT
<213> ORGANISM: Artificial Sequence
<220> FEATURE:
<223> OTHER INFORMATION: mAb001 LCDR3

<400> SEQUENCE: 22

Gln His Phe Trp Gly Thr Pro Leu Thr
1               5

<210> SEQ ID NO 23
<211> LENGTH: 117
<212> TYPE: PRT
<213> ORGANISM: Artificial Sequence
<220> FEATURE:
<223> OTHER INFORMATION: mAb001-VH

<400> SEQUENCE: 23

Ala Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Ser Trp Ile Arg Lys Phe Pro Gly Asn Lys Leu Glu Ser Met
        35                  40                  45

Gly Tyr Met Thr Tyr Ser Gly Ala Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Pro Glu Asp Thr Ala Thr Tyr Tyr Cys Ala
                85                  90                  95

Arg Gly Gly Asn Ser Tyr Phe Phe Asp Tyr Trp Gly Gln Gly Thr Thr
            100                 105                 110

Leu Thr Val Ser Ser
        115

<210> SEQ ID NO 24
<211> LENGTH: 107
<212> TYPE: PRT
<213> ORGANISM: Artificial Sequence
<220> FEATURE:
<223> OTHER INFORMATION: mAb001-VL

<400> SEQUENCE: 24

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
```

```
            20                  25                  30

Leu Ala Trp Tyr Gln Leu Lys Gln Gly Lys Ser Pro His Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Ile Ser Leu Gln Ser
65                  70                  75                  80

Glu Asp Phe Gly Thr Tyr Tyr Cys Gln His Phe Trp Gly Thr Pro Leu
                85                  90                  95

Thr Phe Gly Ala Gly Thr Lys Leu Glu Leu Lys
            100                 105

<210> SEQ ID NO 25
<211> LENGTH: 116
<212> TYPE: PRT
<213> ORGANISM: Artificial Sequence
<220> FEATURE:
<223> OTHER INFORMATION: Humanized heavy chain variable region of
      mAb002c

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Asp Phe
            20                  25                  30

Tyr Ile Asn Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Gly Phe Phe Asp Tyr Trp Gly Gln Gly Thr Leu Val
            100                 105                 110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: Humanized heavy chain variable region of
      mAb002c

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Asp Phe
            20                  25                  30

Tyr Ile Asn Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
```

```
                85                  90                  95
Ala Arg Ser Thr Gly Phe Phe Asp Tyr Trp Gly Gln Gly Thr Leu Val
                100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Humanized heavy chain variable region of
      mAb002c

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Asp Phe
                20                  25                  30

Tyr Ile Asn Trp Val Lys Gln Ala Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Gly Phe Phe Asp Tyr Trp Gly Gln Gly Thr Leu Val
                100                 105                 110

Thr Val Ser Ser
        115

<210> SEQ ID NO 28
<211> LENGTH: 106
<212> TYPE: PRT
<213> ORGANISM: Artificial Sequence
<220> FEATURE:
<223> OTHER INFORMATION: Humanized light chain variable region of
      mAb002c

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Gly Tyr Met
                20                  25                  30

Tyr Trp Tyr Gln Gln Lys Pro Gly Gln Ala Pro Arg Leu Leu Ile Tyr
            35                  40                  45

Leu Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
                100                 105

<210> SEQ ID NO 29
<211> LENGTH: 106
<212> TYPE: PRT
```

<213> ORGANISM: Artificial Sequence
<220> FEATURE:
<223> OTHER INFORMATION: Humanized light chain variable region of mAb002c

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Gly Tyr Met
            20                  25                  30

Tyr Trp Tyr Gln Gln Lys Pro Gly Gln Ala Pro Arg Leu Leu Ile Tyr
        35                  40                  45

Leu Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 30
<211> LENGTH: 106
<212> TYPE: PRT
<213> ORGANISM: Artificial Sequence
<220> FEATURE:
<223> OTHER INFORMATION: Humanized light chain variable region of mAb002c

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Gly Tyr Met
            20                  25                  30

Tyr Trp Tyr Gln Gln Lys Pro Gly Gln Ser Pro Arg Ser Leu Ile Tyr
        35                  40                  45

Leu Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 31
<211> LENGTH: 106
<212> TYPE: PRT
<213> ORGANISM: Artificial Sequence
<220> FEATURE:
<223> OTHER INFORMATION: Humanized light chain variable region of mAb002c

<400> SEQUENCE: 31

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Gly Tyr Met
            20                  25                  30

Tyr Trp Tyr Gln Gln Lys Pro Gly Gln Ser Pro Arg Ser Leu Ile Tyr
        35                  40                  45

Leu Thr Ser Asn Leu Ala Ser Gly Ile Pro Ala Arg Phe Ser Gly Ser
            50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
                100                 105

<210> SEQ ID NO 32
<211> LENGTH: 106
<212> TYPE: PRT
<213> ORGANISM: Artificial Sequence
<220> FEATURE:
<223> OTHER INFORMATION: Humanized light chain variable region of
      mAb002c

<400> SEQUENCE: 32

Glu Ile Val Leu Thr Gln Ser Pro Asp Phe Gln Ser Val Thr Pro Lys
 1               5                  10                  15

Glu Lys Val Thr Ile Thr Cys Ser Ala Ser Ser Ser Ile Gly Tyr Met
                20                  25                  30

Tyr Trp Tyr Gln Gln Lys Pro Asp Gln Ser Pro Lys Leu Leu Ile Lys
                35                  40                  45

Leu Thr Ser Asn Leu Ala Ser Gly Val Pro Ser Arg Phe Ser Gly Ser
            50                  55                  60

Gly Ser Gly Thr Asp Phe Thr Leu Thr Ile Asn Ser Leu Glu Ala Glu
 65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys
                100                 105

<210> SEQ ID NO 33
<211> LENGTH: 106
<212> TYPE: PRT
<213> ORGANISM: Artificial Sequence
<220> FEATURE:
<223> OTHER INFORMATION: Humanized light chain variable region of
      mAb002c

<400> SEQUENCE: 33

Glu Ile Val Leu Thr Gln Ser Pro Asp Phe Gln Ser Val Thr Pro Lys
 1               5                  10                  15

Glu Lys Val Thr Ile Thr Cys Ser Ala Ser Ser Ser Ile Gly Tyr Met
                20                  25                  30

Tyr Trp Tyr Gln Gln Lys Pro Asp Gln Ser Pro Lys Leu Leu Ile Tyr
                35                  40                  45

Leu Thr Ser Asn Leu Ala Ser Gly Val Pro Ser Arg Phe Ser Gly Ser
            50                  55                  60

Gly Ser Gly Thr Asp Tyr Thr Leu Thr Ile Asn Ser Leu Glu Ala Glu
 65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys
                100                 105

<210> SEQ ID NO 34

<211> LENGTH: 106
<212> TYPE: PRT
<213> ORGANISM: Artificial Sequence
<220> FEATURE:
<223> OTHER INFORMATION: Humanized light chain variable region of
      mAb002c

<400> SEQUENCE: 34

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Gly Tyr Met
            20                  25                  30

Tyr Trp Tyr Gln Gln Lys Pro Asp Gln Ser Pro Lys Ser Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 35
<211> LENGTH: 106
<212> TYPE: PRT
<213> ORGANISM: Artificial Sequence
<220> FEATURE:
<223> OTHER INFORMATION: Humanized light chain variable region of
      mAb002c

<400> SEQUENCE: 35

Gln Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Gly Tyr Met
            20                  25                  30

Tyr Trp Tyr Gln Gln Lys Pro Asp Gln Ser Pro Lys Ser Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 36
<211> LENGTH: 429
<212> TYPE: PRT
<213> ORGANISM: Artificial Sequence
<220> FEATURE:
<223> OTHER INFORMATION: Extracellular domain of human AXL protein

<400> SEQUENCE: 36

Gln Ala Glu Glu Ser Pro Phe Val Gly Asn Pro Gly Asn Ile Thr Gly
1               5                   10                  15

Ala Arg Gly Leu Thr Gly Thr Leu Arg Cys Gln Leu Gln Val Gln Gly
            20                  25                  30

Glu Pro Pro Glu Val His Trp Leu Arg Asp Gly Gln Ile Leu Glu Leu

```
            35                  40                  45
Ala Asp Ser Thr Gln Thr Gln Val Pro Leu Gly Glu Asp Glu Gln Asp
 50                  55                  60

Asp Trp Ile Val Val Ser Gln Leu Arg Ile Thr Ser Leu Gln Leu Ser
 65                  70                  75                  80

Asp Thr Gly Gln Tyr Gln Cys Leu Val Phe Leu Gly His Gln Thr Phe
                     85                  90                  95

Val Ser Gln Pro Gly Tyr Val Gly Leu Glu Gly Leu Pro Tyr Phe Leu
                100                 105                 110

Glu Glu Pro Glu Asp Arg Thr Val Ala Ala Asn Thr Pro Phe Asn Leu
            115                 120                 125

Ser Cys Gln Ala Gln Gly Pro Pro Glu Pro Val Asp Leu Leu Trp Leu
130                 135                 140

Gln Asp Ala Val Pro Leu Ala Thr Ala Pro Gly His Gly Pro Gln Arg
145                 150                 155                 160

Ser Leu His Val Pro Gly Leu Asn Lys Thr Ser Ser Phe Ser Cys Glu
                165                 170                 175

Ala His Asn Ala Lys Gly Val Thr Thr Ser Arg Thr Ala Thr Ile Thr
                180                 185                 190

Val Leu Pro Gln Gln Pro Arg Asn Leu His Leu Val Ser Arg Gln Pro
            195                 200                 205

Thr Glu Leu Glu Val Ala Trp Thr Pro Gly Leu Ser Gly Ile Tyr Pro
210                 215                 220

Leu Thr His Cys Thr Leu Gln Ala Val Leu Ser Asp Asp Gly Met Gly
225                 230                 235                 240

Ile Gln Ala Gly Glu Pro Asp Pro Pro Glu Glu Pro Leu Thr Ser Gln
                245                 250                 255

Ala Ser Val Pro Pro His Gln Leu Arg Leu Gly Ser Leu His Pro His
                260                 265                 270

Thr Pro Tyr His Ile Arg Val Ala Cys Thr Ser Ser Gln Gly Pro Ser
            275                 280                 285

Ser Trp Thr His Trp Leu Pro Val Glu Thr Pro Glu Gly Val Pro Leu
290                 295                 300

Gly Pro Pro Glu Asn Ile Ser Ala Thr Arg Asn Gly Ser Gln Ala Phe
305                 310                 315                 320

Val His Trp Gln Glu Pro Arg Ala Pro Leu Gln Gly Thr Leu Leu Gly
                325                 330                 335

Tyr Arg Leu Ala Tyr Gln Gly Gln Asp Thr Pro Glu Val Leu Met Asp
                340                 345                 350

Ile Gly Leu Arg Gln Glu Val Thr Leu Glu Leu Gln Gly Asp Gly Ser
            355                 360                 365

Val Ser Asn Leu Thr Val Cys Val Ala Ala Tyr Thr Ala Ala Gly Asp
370                 375                 380

Gly Pro Trp Ser Leu Pro Val Pro Leu Glu Ala Trp Arg Pro Gly Gln
385                 390                 395                 400

Ala Gln Pro Val His Gln Leu Val Lys Glu Pro Ser Thr Pro Ala Phe
                405                 410                 415

Ser Trp Pro His His His His His His His His
                420                 425

<210> SEQ ID NO 37
<211> LENGTH: 114
<212> TYPE: PRT
<213> ORGANISM: Artificial Sequence
```

-continued

```
<220> FEATURE:
<223> OTHER INFORMATION: AXL107-VH

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Thr Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Trp Ile Ala Phe Asp Ile Trp Gly Gln Gly Thr Met Val
            100                 105                 110

Thr Val

<210> SEQ ID NO 38
<211> LENGTH: 108
<212> TYPE: PRT
<213> ORGANISM: Artificial Sequence
<220> FEATURE:
<223> OTHER INFORMATION: AXL107-VL

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105
```

AXL-TARGETING ANTIBODY, ANTIBODY-DRUG CONJUGATE, PREPARATION METHOD THEREFOR, AND USE THEREOF

The Sequence Listing associated with this application is provided in text format in lieu of a paper copy, and is hereby incorporated by reference into the specification. The name of the text file containing the Sequence Listing is 370094_402USPCa_Sequence_Listing. The text file is 26 KB, was created on Nov. 13, 2020 and is being submitted electronically via EFS-Web.

TECHNICAL FIELD

The present invention relates to the field of medicine, and in particular to an AXL-targeting antibody, an antibody-drug conjugate (ADC), preparation method therefor, and uses thereof.

BACKGROUND

AXL is a member of the receptor tyrosine kinase subfamily-TAM family. The TAM family includes Tyro-3, Axl and Mer. Their ligands are all protein molecules encoded by growth arrest-specific gene 6 (Gas6). AXL is activated after binding to Gas6, thereby activating its downstream signal transduction pathways such as PI3K/AKT, RAS/ERK and β-Catenin/TCF, thereby regulating a variety of physiological functions such as cell proliferation, apoptosis, chemotaxis, adhesion, and recognition.

Studies have found that AXL is activated and expressed in a variety of cancers, such as in the tumor tissues of lung cancer, breast cancer, prostate cancer, thyroid cancer, endometrial cancer, ovarian cancer and kidney cancer, and participates in a variety of mechanisms such as tumor cell epithelial-mesenchymal transition, angiogenesis, apoptosis and immune regulation. It is also associated with poor prognosis (Cancer Cell 2015, 27:533-46) and drug resistance in many cases (Oncotarget 2015, 6:15321-31; Cancer Res. 2013, 19:279-90), including lung cancer refractory to EGFR inhibitors (Nat. Genet. 2012, 44:852-60) and head and neck cancer resistant to PI3K inhibitors (Cancer Cell 2015, 27:533-46), breast cancer resistant to anti-HER2 (Biochem Soc Trans. 2014, 42:822-30), kidney cancer resistant to sunitinib (Oncogene 2016, 35:2687-97) and neuroblastoma resistant to ALK inhibitors (Oncogene 2016, 35:3681-91). In addition, the expression of AXL is associated with the acquired resistance of traditional chemotherapy and radiotherapy (Theranostics 2016, 6:1205-19). After inhibiting AXL, drug-resistant cells are more sensitive to cytotoxic drugs and targeted inhibitors (Nat. Commun. 2016, 7:13898).

In view of the importance of AXL in tumor targeted therapy and the use as a potential drug target, it is expected to research and develop more antibodies that specifically bind to AXL with good characteristics.

The inventor's previous studies also found that compared with normal tissues, AXL is abnormally activated and expressed in tumor tissues, especially in highly invasive, highly metastatic basal-like and/or triple negative breast cancer, metastatic lung cancer, pancreatic cancer, etc. Compared with other targets, antibodies targeting AXL can be quickly internalized in large quantities. It can be seen that AXL may be a more preferred target for developing antibody-drug conjugate (ADC). However, there is still a lack of highly specific antibody drug conjugates targeting human AXL in the world, especially in China.

Antibody-drug conjugates generally consist of three parts: antibodies or antibody-like ligands, small molecule drugs, and linkers that couple the ligand to the drug. In the structures of antibody drug conjugates currently entering clinical trials, highly active cytotoxic drugs are usually linked to lysine residues on the ligand surface through linkers, or cysteine residues (obtained by the reduction of interchain disulfide bond) in the hinge region of the antibody, and the best drug/ligand ratio (DAR) is 2-4. The large number of lysine residues (over 80) on the surface of the antibody and the non-selectivity of the coupling reaction result in the uncertainty of the number and site of coupling, which in turn leads to the heterogeneity of the antibody-drug conjugate produced. Genmab reported a class of AXL-targeted antibody conjugates (CN201580045131.4), which are also antibody-drug conjugates based on traditional coupling technology.

In addition, the mechanism of action of antibody-drug conjugates seems simple, but whether an antibody-drug conjugate can become a safe and effective drug is very complicated and unpredictable, depending on many factors, such as:

1) the characteristics of the target: whether the target can be effectively endocytosed, the expression level of the target, whether the target has sufficient difference in expression levels between cancer cells and normal cells, and whether the target will be secreted or fall off to the extracellular region and enter the bloodstream.
2) the characteristics of the monoclonal antibody: whether the monoclonal antibody is specific enough for the target (no cross-reactivity with other proteins), the stability of the monoclonal antibody, and the rate and degree of endocytosis after binding to the target.
3) the characteristics of the linker: the linker needs to be stable enough in the blood, and the change of the linker will vary depending on the number and the location of drugs linked on the ADC, which will eventually lead to changes in the safety and effectiveness of the entire ADC drug.

It can be seen that the development of ADC drugs requires a lot of experimentation and verification, and its safety and effectiveness cannot be predicted before the experiment.

In summary, there is an urgent need in the art to develop antibodies and antibody drug conjugates targeting AXL with high affinity, low immunogenicity and good stability.

SUMMARY OF THE INVENTION

The present invention provides an antibody targeting human AXL, which has the biological activity of blocking AXL, the activity of inhibiting tumor growth and metastasis, and can reduce the emergence of resistance to anti-tumor therapy.

The invention also provides an antibody-drug conjugate targeting AXL that has a significant antitumor effect on tumor cells with high expression of AXL.

In a first aspect of the present invention, it provides a heavy chain variable region of an antibody, wherein the heavy chain variable region comprises the following three complementarity determining regions or CDRs:
CDR1 as shown in SEQ ID NO. 1,
CDR2 as shown in SEQ ID NO. 2, and
CDR3 as shown in SEQ ID NO. 3;
or,
CDR1 as shown in SEQ ID NO. 9, CDR2 as shown in SEQ ID NO. 10, and
CDR3 as shown in SEQ ID NO. 11;
or,
CDR1 as shown in SEQ ID NO. 17,
CDR2 as shown in SEQ ID NO. 18, and
CDR3 as shown in SEQ ID NO. 19;
wherein any one of the above amino acid sequences further comprises a derivative sequence which is obtained through optional addition, deletion, modification and/or substitution of at least one amino acid and is capable of retaining AXL binding affinity.

In another preferred embodiment, the heavy chain variable region comprises the following complementarity determining regions:
heavy chain complementarity determining regions HCDR1, HCDR2, and HCDR3 of mAb002c as shown in SEQ ID NO. 1, SEQ ID NO. 2, and SEQ ID NO. 3; or
heavy chain complementarity determining regions HCDR1, HCDR2, and HCDR3 of mAb005c as shown in SEQ ID NO. 9, SEQ ID NO. 10, and SEQ ID NO. 11; or
heavy chain complementarity determining regions HCDR1, HCDR2, and HCDR3 of mAb001c as shown in SEQ ID NO. 17, SEQ ID NO. 18, and SEQ ID NO. 19.

In another preferred embodiment, the heavy chain variable region further comprises human FR regions or mouse FR regions.

In another preferred embodiment, the heavy chain variable region has the amino acid sequence as shown in SEQ ID NO. 7.

In another preferred embodiment, the heavy chain variable region has the amino acid sequence as shown in SEQ ID NO. 15.

In another preferred embodiment, the heavy chain variable region has the amino acid sequence as shown in SEQ ID NO. 23.

In another preferred embodiment, the heavy chain variable region has the amino acid sequence as shown in SEQ ID NO. 25, SEQ ID NO. 26, or SEQ ID NO. 27.

In a second aspect of the present invention, it provides a heavy chain of an antibody, which has the heavy chain variable region of the first aspect of the present invention.

In another preferred embodiment, the heavy chain of the antibody further comprises a heavy chain constant region.

In another preferred embodiment, the heavy chain constant region is of human, mouse or rabbit.

In a third aspect of the present invention, it provides a light chain variable region of an antibody, wherein the light chain variable region comprises the following three complementarity determining regions or CDRs:
or,
CDR1' as shown in SEQ ID NO. 4,
CDR2' as shown in SEQ ID NO. 5, and
CDR3' as shown in SEQ ID NO. 6;
or,
CDR1' as shown in SEQ ID NO. 12,
CDR2' as shown in SEQ ID NO. 13, and
CDR3' as shown in SEQ ID NO. 14;
or,
CDR1' as shown in SEQ ID NO. 20,
CDR2' as shown in SEQ ID NO. 21, and
CDR3' as shown in SEQ ID NO. 22;
wherein any one of the above amino acid sequences further comprises a derivative sequence which is obtained through optional addition, deletion, modification and/or substitution of at least one amino acid and is capable of retaining AXL binding affinity.

In another preferred embodiment, the light chain variable region comprises the following complementarity determining regions:
light chain complementarity determining regions LCDR1, LCDR2, and LCDR3 of mAb002c as shown in SEQ ID NO. 4, SEQ ID NO. 5, and SEQ ID NO. 6; or
light chain complementarity determining regions LCDR1, LCDR2, and LCDR3 of mAb005c as shown in SEQ ID NO. 12, SEQ ID NO. 13, and SEQ ID NO. 14; or
light chain complementarity determining regions LCDR1, LCDR2, and LCDR3 of mAb001c as shown in SEQ ID NO. 20, SEQ ID NO. 21, and SEQ ID NO. 22.

In another preferred embodiment, the light chain variable region further comprises human FR regions or mouse FR regions.

In another preferred embodiment, the light chain variable region has the amino acid sequence as shown in SEQ ID NO. 8.

In another preferred embodiment, the light chain variable region has the amino acid sequence as shown in SEQ ID NO. 16.

In another preferred embodiment, the light chain variable region has the amino acid sequence as shown in SEQ ID NO. 24.

In another preferred embodiment, the light chain variable region has the amino acid sequence as shown in SEQ ID NO. 28, SEQ ID NO. 29, SEQ ID NO. 30, or SEQ ID NO. 31.

In another preferred embodiment, the light chain variable region has the amino acid sequence as shown in SEQ ID NO. 32, SEQ ID NO. 33, SEQ ID NO. 34, or SEQ ID NO. 35.

In a fourth aspect of the present invention, it provides a light chain of an antibody, which has the light chain variable region of the third aspect of the present invention.

In another preferred embodiment, the light chain of the antibody further comprises a light chain constant region.

In another preferred embodiment, the light chain constant region is of human, mouse or rabbit.

In a fifth aspect of the present invention, it provides an antibody having:
(1) the heavy chain variable region of the first aspect of the present invention; and/or
(2) the light chain variable region of the third aspect of the present invention;
alternatively, the antibody has: the heavy chain of the second aspect of the present invention; and/or the light chain of the fourth aspect of the present invention.

In another preferred embodiment, the antibody is selected from the group consisting of an animal-derived antibody, a chimeric antibody, a humanized antibody, and a combination thereof.

In another preferred embodiment, the CDR region of the humanized antibody comprises 1, 2, or 3 amino acid changes.

In another preferred embodiment, the animal is a non-human mammal, preferably a mouse, sheep, or rabbit.

In another preferred embodiment, the antibody is a double chain antibody or a single chain antibody.

In another preferred embodiment, the antibody is a monoclonal antibody.

In another preferred embodiment, the antibody is a partially or fully humanized monoclonal antibody.

In another preferred embodiment, the number of added, deleted, modified and/or substituted amino acids does not exceed 40%, preferably 20%, more preferably 10% of the total number of amino acids in the initial amino acid sequence.

In another preferred embodiment, the number of added, deleted, modified and/or substituted amino acids is 1-7, preferably 1-3, and more preferably one.

In another preferred embodiment, the sequence obtained through addition, deletion, modification and/or substitution of at least one amino acid is an amino acid sequence with at least 80% homology.

In another preferred embodiment, the derivative sequence obtained through addition, deletion, modification and/or substitution of at least one amino acid has the function of inhibiting cell surface AXL or recombinant AXL protein.

In another preferred embodiment, the antibody is in the form of a drug conjugate.

In another preferred embodiment, the affinity $EC_{50}$ of the antibody to AXL (such as the extracellular domain of human AXL protein, AXL-ECD) is 0.04-0.5 nM, preferably 0.04-0.1 nM, more preferably is 0.04-0.05 nM.

In another preferred embodiment, the affinity $EC_{50}$ of the antibody to AXL on the tumor cell surface is 0.1-1.5 nM, preferably 0.1-1 nM, more preferably 0.1-0.2 nM.

In another preferred embodiment, the toxic effect $IC_{50}$ of the antibody-drug conjugate (AXL-ADC) on AXL highly expressed tumor cell is 0.01-1 nM, preferably 0.01-0.1 nM, more preferably 0.01-0.05 nM.

In a sixth aspect of the invention, it provides a recombinant protein which comprises:
  (i) the heavy chain variable region of the first aspect of the present invention, the heavy chain of the second aspect of the present invention, the light chain variable region of the third aspect of the present invention, the light chain of the fourth aspect of the present invention, or the antibody of the fifth aspect of the present invention; and
  (ii) an optional tag sequence that assists in expression and/or purification.

In another preferred embodiment, the tag sequence comprises a 6His tag.

In another preferred embodiment, the recombinant protein (or polypeptide) comprises a fusion protein.

In another preferred embodiment, the recombinant protein is a monomer, a dimer, or a multimer.

In a seventh aspect of the present invention, it provides a CAR construct, wherein the scFv segment of the monoclonal antibody antigen binding region of the CAR construct is a binding region that specifically binds to AXL, and the scFv has the heavy chain variable region of the first aspect of the present invention and the light chain variable region of the third aspect of the present invention.

In an eighth aspect of the present invention, it provides a recombinant immune cell expressing exogenous CAR construct of the seventh aspect of the present invention.

In another preferred embodiment, the immune cell is selected from the group consisting of: a NK cell and a T cell.

In another preferred embodiment, the immune cell is derived from human or non-human mammals (such as mice).

In a ninth aspect of the present invention, it provides an antibody-drug conjugate comprising:
  (a) an antibody moiety selected from the group consisting of: the heavy chain variable region of claim 1, the heavy chain of claim 2, the light chain variable region of claim 3, the light chain of claim 4, and the antibody of claim 5, and a combination thereof; and
  (b) a coupling moiety coupled to the antibody moiety, and the coupling moiety is selected from the group consisting of a detectable label, a cytotoxic drug, a cytokine, a radionuclide, an enzyme, and a combination thereof;

In another preferred embodiment, the antibody-drug conjugate or ADC is as shown in the following molecular formula:

wherein,

Ab is an anti-ALX antibody,

LU is a linker;

D is a drug;

and the subscript p is a value selected from 1-10, and preferably 1-8.

In another preferred embodiment, the coupling moiety (D) is a cytotoxic drug, and the cytotoxic drug is a microtubule targeting drug and/or a DNA targeting drug and/or a topoisomerase inhibitor.

In another preferred embodiment, the microtubule targeting drug is selected from the group consisting of: monomethyl auristatin E (MMAE), monomethyl auristatin F (MMAF), maytansine derivative DM1 and tubulysin.

In another preferred embodiment, the DNA targeting drug is selected from the group consisting of docamycin, and pyrrolo[2,1-c][1,4]benzodiazepine (PBD).

In another preferred embodiment, the topoisomerase inhibitor is selected from the group consisting of: 7-ethyl-10-hydroxycamptothecin (SN38), Exatecan and analogs thereof.

In another preferred embodiment, the antibody moiety is coupled to the coupling moiety via a chemical bond or linker.

In another preferred embodiment, the linker (LU) is selected from the group consisting of 4-(N-maleimidomethyl)cyclohexane-1-carboxylic acid succinate (MCC), maleimidocaproyl (MC), 6-maleimidocaproyl-valine-citrulline-p-aminobenzyloxycarbonyl (mc-val-cit-PAB), CL2A (US20140170063, CN201480041766.2) and disubstituted maleimide linkers (CN201611093699.6, CN201711169847.2).

In another preferred embodiment, the toxic effect $IC_{50}$ of the antibody-drug conjugate on AXL highly expressed tumor cell is 0.01-1 nM, preferably 0.01-0.1 nM, more preferably 0.01-0.05 nM.

In a tenth aspect of the present invention, it provides use of an active ingredient selected from the group consisting of: the heavy chain variable region of the first aspect of the present invention, the heavy chain of the second aspect of the present invention, the light chain variable region of the third aspect of the present invention, the light chain of the fourth aspect of the present invention, the antibody of the fifth aspect of the present invention, the recombinant protein of the sixth aspect of the present invention, the immune cell of the eighth aspect, the antibody-drug conjugate of the ninth aspect of the present invention, and a combination thereof, wherein the active ingredient is used for (a) preparing a detection reagent, a detection plate or a kit; and/or (b) preparing a drug for the prevention and/or treatment of an AXL-related disease.

In another preferred embodiment, the detection reagent, detection plate or kit is used for:
(1) detecting AXL protein in the sample; and/or
(2) detecting endogenous AXL protein in tumor cells; and/or
(3) detecting tumor cells expressing AXL protein.

In another preferred embodiment, the detection reagent, detection plate or kit is used for diagnosing an AXL-related disease.

In another preferred embodiment, the drug is used for treating or preventing an AXL highly expressed tumor, tumor migration, or tumor resistance.

In another preferred embodiment, the tumor resistance comprises: resistance of tumor immunotherapy drug, resistance of tumor targeted therapy drug, resistance of conventional tumor chemotherapy, and insensitivity to radiotherapy.

In another preferred embodiment, the drug is used for a use selected from the group consisting of:
(a) specifically binding to tumor cells, and/or AXL of the immune/stromal cells in the tumor microenvironment;
(b) inhibiting over-activated AXL biological function in the tumor/tumor microenvironment;
(c) inhibiting tumor cell migration or metastasis;
(d) inhibiting tumor growth and improving the anti-tumor efficacy of combination drug therapy;
(e) antibody-dependent cell-mediated cytotoxicity (ADCC).

In another preferred embodiment, the AXL-related disease is selected from the group consisting of cancer, an autoimmune disease, a metabolism-related disease, an infectious disease, and a combination thereof.

In another preferred embodiment, the cancer comprises a solid tumor and a hematologic cancer.

In another preferred embodiment, the cancer is a tumor with high AXL expression.

In another preferred embodiment, the tumor with high AXL expression is selected from the group consisting of breast cancer, lung cancer, pancreatic cancer, ovarian cancer, prostate cancer, rectal cancer, glioma, melanoma, leukemia, lymphoma, and a combination thereof.

In another preferred embodiment, the cancer is a drug-resistant tumor.

In another preferred embodiment, the tumor with high AXL expression refers to the ratio of the level L1 of AXL transcript and/or protein in tumor tissue to the level L0 of AXL transcript and/or protein in normal tissue, and L1/L0 is ≥2, preferably ≥3.

In another preferred embodiment, the metabolism-related diseases comprises diabetes, diet-induced obesity, and adipose inflammation.

In another preferred embodiment, the infectious disease comprises bacterial and viral infection.

In an eleventh aspect of the present invention, it provides a pharmaceutical composition comprising:
(i) an active ingredient selected from the group consisting of: the heavy chain variable region of the first aspect of the present invention, the heavy chain of the second aspect of the present invention, the light chain variable region of the third aspect of the present invention, the light chain of the fourth aspect of the present invention, the antibody of the fifth aspect of the present invention, the recombinant protein of the sixth aspect of the present invention, the immune cell of the eighth aspect, the antibody-drug conjugate of the ninth aspect of the present invention, and a combination thereof; and
(ii) a pharmaceutically acceptable carrier.

In another preferred embodiment, the pharmaceutical composition is a liquid formulation.

In another preferred embodiment, the pharmaceutical composition is an injection.

In a twelfth aspect of the present invention, it provides a polynucleotide encoding a polypeptide selected from the group consisting of:
(1) the heavy chain variable region of the first aspect of the present invention, the heavy chain of the second aspect of the present invention, the light chain variable region of the third aspect of the present invention, the light chain of the fourth aspect of the present invention, or the antibody of the fifth aspect of the present invention; or
(2) the recombinant protein of the sixth aspect of the present invention;
(3) the CAR construct of the seventh aspect of the present invention.

In a thirteenth aspect of the invention, it provides a vector comprising the polynucleotide of the twelfth aspect of the present invention.

In another preferred embodiment, the vector comprises: a bacterial plasmid, a phage, a yeast plasmid, a plant cell virus, a mammalian cell virus such as an adenovirus, retrovirus, or other vectors.

In a fourteenth aspect of the invention, it provides a genetically engineered host cell comprising the vector of the thirteenth aspect of the present invention or having the polynucleotide of the twelfth present aspect of the invention integrated into its genome.

In a fifteenth aspect of the present invention, it provides an in vitro method (including diagnostic or non-diagnostic method) for detecting AXL in a sample, wherein the method comprising the steps:
(1) contacting a sample with the antibody of the fifth aspect of the present invention in vitro;
(2) detecting whether an antigen-antibody complex is formed, wherein the formation of a complex indicates the presence of AXL in the sample.

In a sixteenth aspect of the present invention, it provides a detection plate comprising a substrate (or support plate) and a test strip, wherein the test strip comprising the antibody of the fifth aspect of the present invention or the immunoconjugate of the ninth aspect of the present invention.

In a seventeenth aspect of the present invention, it provides a kit comprising:
(1) a first container containing the antibody of the fifth aspect of the present invention; and/or
(2) a second container containing a secondary antibody against the antibody of the fifth aspect of the present invention;
alternatively, the kit comprises the detection plate of the sixteenth aspect of the present invention.

In an eighteenth aspect of the present invention, it provides a method for preparing a recombinant polypeptide, which comprises the steps of:
(i) culturing the host cell of the fourteenth aspect of the present invention under a condition suitable for expression;
(b) isolating a recombinant polypeptide from the culture, wherein the recombinant polypeptide is the antibody of the fifth aspect of the present invention or the recombinant protein of the sixth aspect of the present invention.

In a nineteenth aspect of the present invention, it provides a method for treating AXL-related diseases, wherein the method comprises: administering the antibody of the fifth aspect of the present invention, the antibody-drug conjugate of the antibody, or the CAR-T cell expressing the antibody, and a combination thereof, to a subject in need.

In another preferred embodiment, the method further comprises: administering other drugs or treatment methods to the subject in need for a combined therapy.

In another preferred embodiment, the other drugs or treatment methods comprise: an anti-tumor immunotherapy drug, a tumor-targeted drug, a tumor chemotherapeutic agent, and tumor radiotherapy.

In another preferred embodiment, the anti-tumor immunotherapy drug comprises a PD-1 and PD-L1 monoclonal antibody.

In a twentieth aspect of the invention, it provides a method for the preparation of an chimeric antibody, comprising the steps of:
cloning the nucleotide sequence of the heavy chain variable region of the first aspect of the present invention and/or the light chain variable region of the third aspect of the present invention into an expression vector containing the nucleotide sequence of a human antibody constant region, and expressing the human-mouse chimeric antibody by transfecting animal cells.

In a twenty-first aspect of the present invention, it provides a method for the preparation of an humanized antibody, comprising the steps of:
implanting the nucleotide sequences of the CDR regions in the heavy chain variable region of the first aspect of the present invention and/or the light chain variable region of the third aspect of the present invention into a nucleoside sequence template containing human antibody FR regions, then cloning the resultant template into an expression vector containing the constant region of a human antibody, and expressing the humanized antibody by transfecting animal cells.

In a twenty-second aspect of the present invention, it provides a method for inhibiting tumor cell growth and migration, comprising the steps of: administering the antibody of the fifth aspect of the present invention and an antibody-drug conjugate of the antibody, a CAR-T cell expressing the antibody, and a combination thereof to a subject in need.

In a twenty-third aspect of the present invention, it provides a method for inhibiting tumor growth in a model animal, comprising the steps of: administering the antibody of the fifth aspect of the present invention and an antibody-drug conjugate of the antibody, or a CAR-T cell expressing the antibody to a subject in need.

In another preferred embodiment, the drug can be administered alone or in combination with, such as, tumor immunotherapy, a tumor-targeted drug, a cytotoxic drug, and radiotherapy.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

DESCRIPTION OF DRAWINGS

FIG. 1A shows the binding activity of original discovered anti-human AXL monoclonal antibodies (original hybridoma) culture supernatant to human breast cancer cells MDA-MB-231 (AXL-P) with AXL high expression and MDA-MB-453 (AXL-N) with AXL low expression as detected by Fluorescence Activated Cell Sorter (FACS). FIG. 1B shows the numbers of six monoclonal antibodies (mAb001, mAb002, mAb003, mAb004, mAb005 and mAb006) and the identification of the subtypes of the purified antibodies.

FIG. 50A shows the protein expression level 24 hours after the transient transfection of monkey AXL vector in HEK293T as detected by Western blot; FIG. 50B shows the binding affinity $EC_{50}$ of Hu002-2 to HEK293T cells as detected by FASC, wherein the HEK293T cells were harvested 24 hours after the transient transfection to express monkey AXL.

MODES FOR CARRYING OUT THE PRESENT INVENTION

Figure 1:
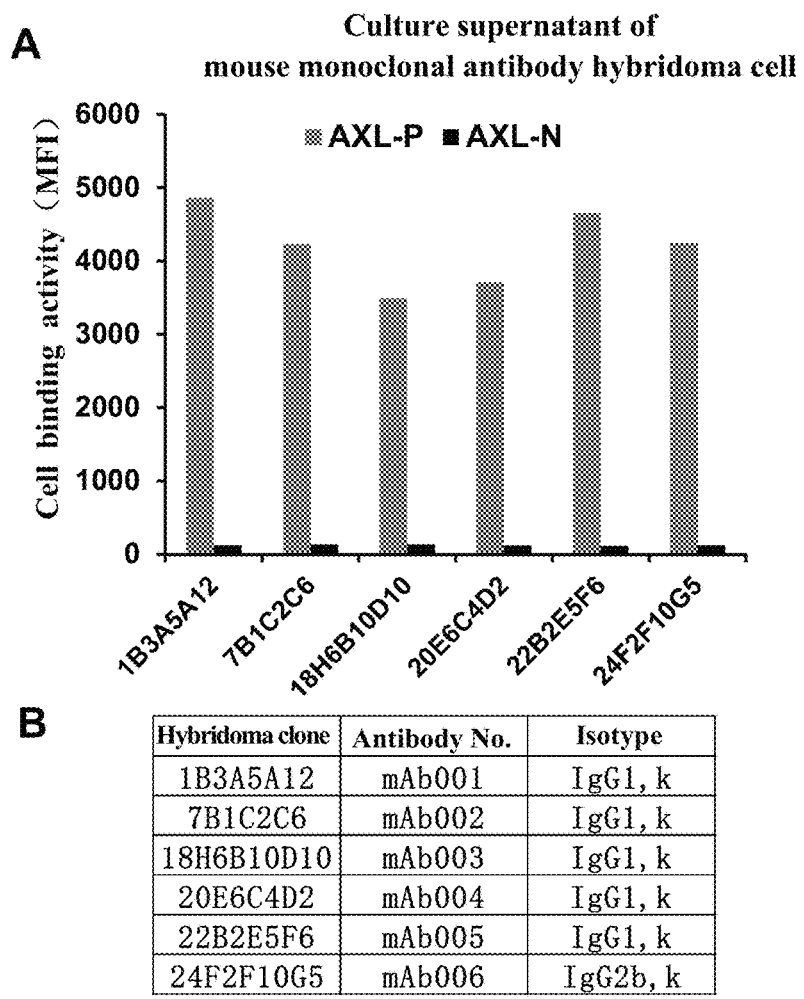
FIG. 1 shows the discovery of the anti-human AXL antibody of the present invention.

Through extensive and intensive research, the inventors unexpectedly obtained 6 anti-AXL monoclonal antibodies after extensive screening, named mAb001 to mAb006, respectively. According to the activity test results, mAb001 (IgG1-κ), mAb002 (IgG1-κ), mAb005 (IgG1-κ) and mAb006 (IgG2b-κ) were selected to construct human-mouse chimeric antibodies, which were named as mAb001c, mAb002c, mAb005c and mAb006c, respectively. The above antibodies were further tested, and the results are as follows.

Firstly, all the chimeric antibodies can bind to AXL antigen with high specificity, and the $EC_{50}$ determined by ELISA were 0.092 nM, 0.073 nM, 0.103 nM and 0.101 nM, respectively.

Secondly, the chimeric antibody has extremely high binding affinities against multiple tumor cells with high expression of AXL, and the $EC_{50}$ determined by FACS were 0.174 nM-1.5 nM, and gene sequencing showed that the complementarity determining regions (CDRs) of mAb006c and mAb005c were highly overlapping, so the follow-up study on mAb006c was terminated.

Thirdly, a series of humanized antibodies designed based on mAb002c have higher AXL protein binding affinity and cell binding affinity; the $EC_{50}$ determined by ELISA were 0.045 nM-0.08 nM; the $EC_{50}$ determined by FACS were 0.09 nM-0.14 nM.

Fourthly, the antibody drug conjugate (ADC) has excellent characteristics, that is, it has no obvious toxic and side effects on cells with AXL-normal expression, but has extremely high killing activity on tumor cells with AXL high expression, and the cell proliferation inhibition $IC_{50}$ values were 0.01 nM-0.07 nM.

Fifthly, the AXL-ADC product obtained with the novel linker of the present invention has the advantages of high uniformity and further improved stability in vitro and in vivo.

Sixthly, the antibodies and antibody-drug conjugates preferred in the present invention have better and more sustained anti-tumor therapeutic effects in vivo than those of the prior art.

The present invention has been completed on the basis of this.

Antibody

As used herein, the term "antibody" or "immunoglobulin" is a heterotetrameric glycoprotein of about 150,000 Da having the same structural characteristics, which consists of two identical light chains (L) and two identical heavy chains (H). Each light chain is linked to a heavy chain via a covalent disulfide bond, and different immunoglobulin isotypes have different numbers of disulfide bonds between the heavy chains. There are also regularly spaced intrachain disulfide bonds in each heavy and each light chain. Each heavy chain has a variable region (VH) at one end, followed by a plurality of constant regions. Each light chain has a variable region (VL) at one end and a constant region at the other end; the constant region of a light chain pairs with the first constant region of a heavy chain, and the variable region of a light chain pairs with the variable region of a heavy chain. Special amino acid residues form an interface between the variable regions of a light chain and a heavy chain.

As used herein, the term "variable" means that antibodies are different from each other in terms of sequence in certain parts of variable regions, which is responsible for the binding and specificity of various specific antibodies to their specific antigens. However, the variability is not distributed evenly throughout the variable regions of an antibody. It is concentrated in three segments called complementarity determining regions (CDRs) or hypervariable regions in the light and heavy chain variable regions. The conserved parts of variable regions are called framework regions (FRs). Each of the variable regions of naturally occurring heavy and light chains comprises four FR regions, which are generally in β-sheet configuration, joined by the three CDRs forming a linking loop, and in some cases, may form a partial β-sheet structure. The CDRs in each chain are closely linked together via the FR regions, and together with the CDRs of the other chain, form the antigen binding site of an antibody (see Kabat et al., NIH Publ. No. 91-3242, Vol. I, pp. 647-669 (1991)). The constant regions are not directly involved in the binding of an antibody to an antigen, however, they exhibit different effector functions, for example, they are involved in the antibody-dependent cytotoxicities of an antibody.

The "light chain" of a vertebrate antibody (immunoglobulin) can be classified into one of the two obviously different classes (referred to as κ and λ) depending on the amino acid sequence of its constant region. Immunoglobulins can be classified into different classes depending on the amino acid sequences of their heavy chain constant regions. There are mainly five classes of immunoglobulins: IgA, IgD, IgE, IgG, and IgM, some of which can be further classified into subclasses (isotypes), such as IgG1, IgG2, IgG3, IgG4, IgA, and IgA2. The heavy chain constant regions corresponding to different classes of immunoglobulins are called α, δ, ε, γ, and μ, respectively. The subunit structures and three-dimensional configurations of different classes of immunoglobulins are well known for those skilled in the art.

In general, the antigen binding characteristics of an antibody can be described by three specific regions located in the heavy and light chain variable regions, called complementarity determining regions (CDRs), which divide the variable region into four framework regions (FRs); the amino acid sequences of the four FRs are relatively conservative and are not directly involved in the binding reaction. These CDRs form a ring structure, and approach to each other in the steric structure by virtue of the β-sheets formed by the FRs between them, and the CDRs on the heavy chain and the CDRs on the corresponding light chain constitute the antigen-binding site of an antibody. By comparison of the amino acid sequences of antibodies of the same type, it can be determined which amino acids form FRs or CDRs.

The present invention includes not only an intact antibody, but also the fragments of the antibody having an immunological activity or a fusion protein formed by the antibody and another sequence. Therefore, the present invention also includes fragments, derivatives and analogs of the antibody.

In the present invention, antibodies include murine, chimeric, humanized or fully human antibodies as prepared by techniques well known to those skilled in the art. Recombinant antibodies, such as chimeric and humanized monoclonal antibodies, including human and non-human portions, can be obtained by standard DNA recombination techniques, all of which are useful antibodies. A chimeric antibody is a molecule in which different portions are derived from different animal species, for example, a chimeric antibody having a variable region from a monoclonal antibody from a mouse and a constant region from a human immunoglobulin (see, for example, U.S. Pat. Nos. 4,816,567 and 4,816,397, which are incorporated herein by reference in its entirety). A humanized antibody refers to an antibody molecule derived from a non-human species, which has one or more complementarity determining regions (CDRs) derived from a non-human species and framework regions derived from a human immunoglobulin molecule (see U.S. Pat. No. 5,585,089, which is incorporated herein by reference in its entirety). These chimeric and humanized monoclonal antibodies can be prepared by recombinant DNA techniques well known in the art.

In the present invention, an antibody may be monospecific, bispecific, trispecific, or multispecific.

In the present invention, the antibody of the present invention further includes a conservative variant thereof, which refers to a polypeptide formed by substitution of at most 10, preferably at most 8, more preferably at most 5, and most preferably at most 3 amino acids with amino acids having similar or analogous property, as compared to the amino acid sequence of the antibody of the present invention. These conservative variant polypeptides are preferably formed by carrying out the amino acid substitution according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Anti-AXL Antibody

The present invention provides three types of AXL targeting antibodies with high specificity and high affinity, which comprise a heavy chain and a light chain. The heavy chain comprises the amino acid sequence of heavy chain variable region (VH), and the light chain comprises the amino acid sequence of light chain variable region (VL).

Preferably, the amino acid sequence of heavy chain variable region (VH) and the amino acid sequence of light chain variable region (VL) comprise HCDR1, HCDR2, HCDR3, LCDR1, LCDR2 and LCDR3 having the following polypeptide sequences:

a1) HCDR1 is SEQ ID NO. 1: DFYIN, SEQ ID NO. 9: SYYIH, or SEQ ID NO. 17: SGYWS;
a2) HCDR2 is SEQ ID NO. 2: WIYPGSGNTKYNEKFKG, SEQ ID NO. 10: WIYPGSDNTKYNEKFKD, or SEQ ID NO. 18: YMTYSGATYYNPSLKS;
a3) HCDR3 is SEQ ID NO. 3: STGFFD, SEQ ID NO. 11: NYYDYDGGTWFPY, or SEQ ID NO. 19: GGNSYFFDY;
a4) LCDR1 is SEQ ID NO. 4: SASSSIGYMY, SEQ ID NO. 12: RASQDINYYLN, or SEQ ID NO. 20: RASENIYSNLA;
a5) LCDR2 is SEQ ID NO. 5: LTSNLAS, SEQ ID NO. 13: YTSRLHS, or SEQ ID NO. 21: AATNLAD;
a6) LCDR3 is SEQ ID NO. 6: QQWSSNPPT; SEQ ID NO. 14: QQGNTLPWT, or SEQ ID NO. 22: QHFWGTPLT;
a7) a sequence with AXL binding affinity which is obtained through addition, deletion, modification and/or substitution of at least one amino acid of any amino acid sequence of the above amino acid sequences.

In another preferred embodiment, the sequence obtained through addition, deletion, modification and/or substitution of at least one amino acid is preferably an amino acid sequence having a homology of at least 80%, preferably at least 85%, and more preferably at least 90%, most preferably at least 95%.

Preferably, the antibody can inhibit the function of AXL on the cell surface and recombinant AXL, and the antibody can be quickly internalized into intracellular lysosome.

The antibody of the present invention may be a double-chain or single-chain antibody, and may be selected from an animal-derived antibody, a chimeric antibody, a human-animal chimeric antibody, preferably is a humanized antibody, and more preferably a fully humanized antibody.

The antibody derivative of the present invention may be a single-chain antibody, and/or an antibody fragment, for example, Fab, Fab', (Fab')2 or other antibody derivatives known in the art, etc., and may be any one or more of IgA, IgD, IgE, IgG and IgM antibodies or other subtype antibodies.

In the present invention, the animal is preferably a mammal, such as mouse.

The antibody of the present invention may be a chimeric antibody, a humanized antibody, a CDR grafted and/or modified antibody that targets human AXL.

In a preferred embodiment of the present invention, any one or more sequences of SEQ ID NOs. 1-3, SEQ ID NOs. 9-11, and SEQ ID NOs. 17-19, or sequences thereof that are obtained through addition, deletion, modification and/or substitution of at least one amino acid and have AXL binding affinity, are located in the CDRs of heavy chain variable region (VH).

In a preferred embodiment of the present invention, any one or more sequences of SEQ ID NOs. 4-6, SEQ ID NOs. 12-14, and SEQ ID NOs. 20-22, or sequences thereof that are obtained through addition, deletion, modification and/or substitution of at least one amino acid and have AXL binding affinity, are located in the CDRs of light chain variable region (VL).

In a more preferred embodiment of the present invention, VH CDR1, CDR2, CDR3 are independently selected from any one or more sequences of SEQ ID NO. 1, SEQ ID NO. 2, and SEQ ID NO. 3, or selected from SEQ ID NO. 9, SEQ ID NO. 10, and SEQ ID NO. 11, or selected from SEQ ID NO. 17, SEQ ID NO. 18, and SEQ ID NO. 19, or sequences thereof that are obtained through addition, deletion, modification and/or substitution of at least one amino acid and have AXL binding affinity; VL CDR1, CDR2, CDR3 are independently selected from any one or more sequences of SEQ ID NO. 4, SEQ ID NO. 5, and SEQ ID NO. 6, or selected from SEQ ID NO. 12, SEQ ID NO. 13, and SEQ ID NO. 14, or selected from SEQ ID NO. 20, SEQ ID NO. 21, and SEQ ID NO. 22, or sequences thereof that are obtained through addition, deletion, modification and/or substitution of at least one amino acid and have AXL binding affinity.

In above content of the present invention, the number of the added, deleted, modified and/or substituted amino acids, preferably does not exceed 40%, more preferably does not exceed 35%, is more preferably 1-33%, is more preferably 5-30%, is more preferably 10-25%, and is more preferably 15-20% of the total number of the amino acids of the initial amino acid sequence.

In the above content of the present invention, more preferably, the number of the added, deleted, modified and/or substituted amino acids, may be 1-7, more preferably 1-5, more preferably 1-3, and more preferably 1-2.

In another preferred embodiment, the antibodies are the original murine antibody mAb001, mAb002, mAb003, mAb004, mAb005 and mAb006.

In another preferred embodiment, the antibodies are human-mouse chimeric antibodies mAb001c, mAb002c, mAb005c and mAb006c.

In another preferred embodiment, the antibodies are humanized antibodies Hu002c-1, Hu002c-2, Hu002c-3, Hu002c-4, Hu002c-5, Hu002c-6, Hu002c-7, Hu002c-8, Hu002c-9, Hu002c-10, Hu002c-11, Hu002c-12, Hu002c-13, Hu002c-14, Hu002c-15, Hu002c-16, Hu002c-17, Hu002c-18, Hu002c-19, Hu002c-20, Hu002c-21, Hu002c-22, Hu002c-23 and Hu002c-24.

The three types of antibodies of the present invention can be used in combination, for constructing CAR constructs, recombinant immune cells containing CAR constructs, antibody drug conjugates, etc., and can also be used for (a) preparation of a detection reagent, detection plate or kit; and/or (b) preparation of a medicine for preventing and/or treating an AXL-related disease.

The representative meanings of each sequence involved in the sequence listing of the present invention are as shown in the Table B below:

TABLE B

| Sequence number | Sequence name |
| --- | --- |
| SEQ ID NO. 1 | mAb002 HCDR1 |
| SEQ ID NO. 2 | mAb002 HCDR2 |
| SEQ ID NO. 3 | mAb002 HCDR3 |
| SEQ ID NO. 4 | mAb002 LCDR1 |
| SEQ ID NO. 5 | mAb002 LCDR2 |
| SEQ ID NO. 6 | mAb002 LCDR3 |
| SEQ ID NO. 7 | mAb002-VH |
| SEQ ID NO. 8 | mAb002-VL |
| SEQ ID NO. 9 | mAb005 HCDR1 |
| SEQ ID NO. 10 | mAb005 HCDR2 |
| SEQ ID NO. 11 | mAb005 HCDR3 |
| SEQ ID NO. 12 | mAb005 LCDR1 |
| SEQ ID NO. 13 | mAb005 LCDR2 |
| SEQ ID NO. 14 | mAb005 LCDR3 |
| SEQ ID NO. 15 | mAb005-VH |
| SEQ ID NO. 16 | mAb005-VL |
| SEQ ID NO. 17 | mAb001 HCDR1 |
| SEQ ID NO. 18 | mAb001 HCDR2 |
| SEQ ID NO. 19 | mAb001 HCDR3 |
| SEQ ID NO. 20 | mAb001 LCDR1 |
| SEQ ID NO. 21 | mAb001 LCDR2 |
| SEQ ID NO. 22 | mAb001 LCDR3 |
| SEQ ID NO. 23 | mAb001-VH |
| SEQ ID NO. 24 | mAb001-VL |
| SEQ ID NO. 25 | mAb002-VH_HuG0 |
| SEQ ID NO. 26 | mAb002-VH_HuG1 |
| SEQ ID NO. 27 | mAb002-VH_HuG2 |
| SEQ ID NO. 28 | mAb002-VK_HuG0 |
| SEQ ID NO. 29 | mAb002-VK_HuG1 |
| SEQ ID NO. 30 | mAb002-VK_HuG2 |
| SEQ ID NO. 31 | mAb002-VK_HuG3 |
| SEQ ID NO. 32 | mAb002-VK_HuG4 |
| SEQ ID NO. 33 | mAb002-VK_HuG5 |
| SEQ ID NO. 34 | mAb002-VK_HuG6 |

TABLE B-continued

| Sequence number | Sequence name |
| --- | --- |
| SEQ ID NO. 35 | mAb001-VK_HuG7 |
| SEQ ID NO. 36 | Extracellular domain of human AXL protein |
| SEQ ID NO. 37 | AXL107-VH |
| SEQ ID NO. 38 | AXL107-VL |

The present invention also involves monkey AXL protein sequence and mouse AXL protein sequence, and the Genebank ID are XP_014979499.1 (monkey) and NP_033491.2 (mouse), respectively.

Antibody Preparation

The sequence of the DNA molecule for the antibody or a fragment thereof according to the present invention can be obtained by conventional techniques, for example, methods such as PCR amplification or genomic library screening. In addition, the sequences encoding light chain and heavy chain can be fused together, to form a single-chain antibody.

Once a relevant sequence is obtained, the relevant sequence can be obtained in bulk using a recombination method. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence.

At present, it is possible to obtain a DNA sequence encoding the antibody of the present invention (or fragments thereof, or derivatives thereof) completely by chemical synthesis. The DNA sequence can then be introduced into a variety of existing DNA molecules (or, for example, vectors) and cells known in the art. In addition, mutations can also be introduced into the protein sequences of the present invention by chemical synthesis.

The present invention further relates to a vector comprising said suitable DNA sequence and a suitable promoter or a control sequence. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as a mammalian cell. Preferred animal cells include, but are not limited to, CHO-S, HEK-293 cells.

In general, under conditions suitable for expression of the antibody according to the present invention, the host cell obtained is cultured. Then, the antibody of the present invention is purified by using conventional immunoglobulin purification steps, for example, the conventional separation and purification means well known to those skilled in the art, such as protein A-Sepharose, hydroxyapatite chromatography, gel electrophoresis, dialysis, ion exchange chromatography, hydrophobic chromatography, molecular sieve chromatography or affinity chromatography.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)). The binding affinity of a monoclonal antibody can be determined by, for example, the Scatchard analysis (Munson et al., Anal. Biochem., 107: 220 (1980)).

The antibody according to the present invention can be expressed in a cell or on the cell membrane, or is secreted extracellularly. If necessary, the recombinant protein can be separated and purified by various separation methods according to its physical, chemical, and other properties. These methods are well known to those skilled in the art. The examples of these methods comprise, but are not limited to, conventional renaturation treatment, treatment by protein precipitant (such as salt precipitation), centrifugation, cell lysis by osmosis, ultrasonic treatment, supercentrifugation, molecular sieve chromatography (gel chromatography), adsorption chromatography, ion exchange chromatography, high performance liquid chromatography (HPLC), and any other liquid chromatography, and the combination thereof.

Antibody-Drug Conjugate

The present invention also provides an antibody-drug conjugate (ADC) based on the antibody according to the present invention.

Typically, the antibody-drug conjugate comprises the antibody and an effector molecule, wherein the antibody is conjugated to the effector molecule, and chemical conjugation is preferred. Preferably, the effector molecule is a therapeutically active drug. In addition, the effector molecule may be one or more of a toxic protein, a chemotherapeutic drug, a small-molecule drug or a radionuclide.

The antibody according to present invention and the effector molecule may be coupled by a coupling agent. Examples of the coupling agent may be any one or more of a non-selective coupling agent, a coupling agent utilizing a carboxyl group, a peptide chain, and a coupling agent utilizing a disulfide bond. The non-selective coupling agent refers to a compound that results in a linkage between an effector molecule and an antibody via a covalent bond, such as glutaraldehyde, etc. The coupling agent utilizing a carboxyl group may be any one or more of cis-aconitic anhydride coupling agents (such as cis-aconitic anhydride) and acyl hydrazone coupling agents (the coupling site is acyl hydrazone).

Certain residues on an antibody (such as Cys or Lys, etc.) are used to link a variety of functional groups, including imaging agents (such as chromophores and fluorophores), diagnostic agents (such as MRI contrast agents and radioisotopes), stabilizers (such as poly(ethylene glycol)) and therapeutic agents. An antibody can be conjugated to a functional agent to form a conjugate of the antibody-functional agent. A functional agent (e.g. a drug, a detection reagent, a stabilizer) is conjugated (covalently linked) to an antibody. A functional agent can be linked to an antibody either directly or indirectly via a linker.

Antibodies can be conjugated to drugs to form antibody-drug conjugates (ADCs). Typically, an ADC comprises a linker between a drug and an antibody. The linker can be a degradable or non-degradable linker. Typically, degradable linkers are easily degraded in an intracellular environment, for example, the linker is degraded at the target site, thereby releasing the drug from the antibody. Suitable degradable linkers include, for example, enzyme-degradable linkers, including peptidyl-containing linkers that can be degraded by protease (e.g. lysosomal protease or endosomal protease) in a cell, or sugar linkers, for example, glucuronide-containing linkers that can be degraded by glucuronidase. Peptidyl linkers may include, for example, dipeptides, such as valine-citrulline, phenylalanine-lysine or valine-alanine. Other suitable degradable linkers include, for example, pH sensitive linkers (e.g. linkers that are hydrolyzed at a pH of below 5.5, such as hydrazone linkers) and linkers that are degraded under reducing conditions (e.g. disulfide-bond linkers). A non-degradable linker typically releases a drug under conditions that the antibody is hydrolyzed by protease.

Prior to linkage to an antibody, a linker has a reactive group capable of reacting with certain amino acid residues, and the linkage is achieved by the reactive group. A thiol-specific reactive group is preferred, and includes, for example, a maleimide compound, a halogenated (e.g. iodo-, bromo- or chloro-substituted) amide; a halogenated (e.g. iodo-, bromo- or chloro-substituted) ester; a halogenated (e.g. iodo-, bromo- or chloro-substituted) methyl ketone, a benzyl halide (e.g. iodide, bromide or chloride); vinyl sulfone, pyridyl disulfide; a mercury derivative such as 3,6-di-(mercurymethyl)dioxane, wherein the counter ion is $CH^3COO^-$, $Cl^-$ or $NO^{3-}$; and polymethylene dimethyl sulfide thiosulfonate. The linker may include, for example, a maleimide linked to an antibody via thiosuccimide.

A drug may be any cytotoxic drug which inhibits cell growth or immunosuppression. In an embodiment, an antibody is linked to a drug via a linker, and the drug has a functional group that can form a bond with the linker. For example, a drug may have an amino group, a carboxyl group, a thiol group, a hydroxyl group, or a ketone group that can form a bond with a linker. When a drug is directly linked to a linker, the drug has a reactive group before being linked to an antibody.

Useful drugs include, for example, anti-tubulin drugs, DNA minor groove binding agents, DNA replication inhibitors, alkylating agents, antibiotics, folic acid antagonists, antimetabolites, chemotherapy sensitizers, topoisomerase inhibitors, vinca alkaloids, etc. Examples of particularly useful cytotoxic drugs include, for example, DNA minor groove binding agents, DNA alkylating agents, and tubulin inhibitors; typical cytotoxic drugs include, for example, auristatins, camptothecins, docamycin/duocarmycins, etoposides, maytansines and maytansinoids (e.g. DM1 and DM4), taxanes, benzodiazepines or benzodiazepine containing drugs (e.g. pyrrolo[1,4]benzodiazepines (PBDs), indolinobenzodiazepines and oxazolidinobenzodiazepines), and vinca alkaloids, 7-ethyl-10-hydroxycamptothecin (SN38), Exatecan and analogues thereof, etc.

In the present invention, a drug-linker can be used to form an ADC in a simple step. In other embodiments, a bifunctional linker compound can be used to form an ADC in a two-step or multi-step process. For example, a cysteine residue is reacted with the reactive moiety of a linker in a first step, and then the functional group on the linker is reacted with a drug in the subsequent step, so as to form an ADC.

In general, the functional group on a linker is selected so that it can specifically react with the suitable reactive group on a drug moiety. As a non-limiting example, an azide-based moiety can be used to specifically react with the reactive alkynyl group on a drug moiety. The drug is covalently bound to the linker by 1,3-dipolar cycloaddition between the azide and alkynyl group. Other useful functional groups include, for example, ketones and aldehydes (suitable for reacting with hydrazides and alkoxyamines), phosphines (suitable for reacting with azides); isocyanates and isothiocyanates (suitable for reacting with amines and alcohols); and activated esters, for example, N-hydroxysuccinimide esters (suitable for reacting with amines and alcohols). These and other linkage strategies, for example, those described in "Bioconjugation Technology" (2nd Edition (Elsevier)), are well known to those skilled in the art. Those skilled in the art could understand that when a complementary pair of reactive functional groups are selected for a selective reaction between a drug moiety and a linker, each member of the complementary pair can be used for the linker, and can also be used for the drug.

The present invention further provides a method for preparing an ADC, which may further comprise: under conditions sufficient to form an antibody-drug conjugate (ADC), binding an antibody to a drug-linker compound.

In certain embodiments, the method according to the present invention comprises: under conditions sufficient to form an antibody-linker conjugate, binding an antibody to a bifunctional linker compound. In these embodiments, the method according to the present invention further comprises: under conditions sufficient to covalently link the drug moiety to the antibody via a linker, binding the antibody-linker conjugate to the drug moiety.

In some embodiments, an antibody-drug conjugate (ADC) has a formula as follows:

wherein:
Ab is an antibody,
LU is a linker;
D is a drug;
And the subscript p is a value selected from 1 to 8.

AXL Antibody-Drug Conjugate

The present invention relates to an antibody-drug conjugate, and more specifically, the present invention relates to an AXL antibody-drug conjugate with therapeutic applications. The anti-AXL antibody can be coupled to a chemotherapeutic drug or a small molecule toxin through a specific linker. The invention also relates to a method for treating mammalian cells or related pathological conditions using the anti-AXL antibody-drug conjugate.

The large number of lysine residues (over 80) on the surface of the antibody and the non-selectivity of the coupling reaction result in the uncertainty of the number and site of coupling, which further leads to the heterogeneity of the antibody-drug conjugate produced. For example, T-DM1 (average DAR value is 3.5) has a DAR value distribution of 0-8. Similarly, although there are only four pairs of interchain disulfide bonds in the hinge region of an antibody, in order to achieve the best average DAR value (2-4), it is necessary to partially reduce the interchain disulfide bonds. Since the existing reducing agents (DTT, TCEP, etc.) cannot selectively reduce the interchain disulfide bonds, the resulting conjugate is not a uniform product, and consists of multiple components. The DAR values of the main components are 0, 2, 4, 6, 8, and each component corresponding to a specific DAR value has isomers formed due to different attachment sites. The heterogeneity of antibody-drug conjugate products can lead to heterogeneities in the pharmacokinetic property, titer, and toxicity of each component. For example, components with higher DAR values are cleared faster in vivo and cause higher toxicity.

In view of the problems of the above coupling technology, a simple chemical method to achieve the purpose of targeted coupling of existing antibodies will save a lot of human resources, material resources and financial resources, so it is more attractive. Related researches include: CN200480019814.4 applied by Polytherics Ltd.; WO2014197871A2 applied by Igenica Biotherapeutics Ltd.; CN201380025774.3 applied by Concortis Biosystems Corp.; CN201310025021.4 applied by Shanghai Newbio Therapeutics, Inc., etc. However, the above technologies have problems of long synthetic routes for coupling reagents, poor chemical stability of coupling reagents, and messy electrophoretogram of antibody conjugates (suggesting that there may be side reactions during the coupling process), and sulfhydryl exchange (reverse Michael addition reaction) during the in vivo circulation which has not been solved by existing solutions, etc.

Genmab reported a class of AXL-targeted antibody conjugates (CN201580045131.4), which are also antibody-drug conjugates based on traditional coupling technology.

In view of the problems of the above coupling technology, the targeted coupling of antibody-drug conjugate targeting AXL achieved by a simple chemical method can improve the uniformity of the drug and save a large amount of human resources, material resources and financial resources in process and quality control, and can also improve the druggability of the conjugate including stability, efficacy and safety.

A new type of linker substructure (a novel disubstituted maleimide linker previously developed by the inventors, CN201611093699.6, CN201711169847.2) is applied for coupling the AXL-targeting antibody in the present invention. The linker can full/partially cross-couple the reduced cysteine sulfhydryl group of the disulfide bond in the light chain-heavy chain and heavy chain-heavy chain of the antibody. Compared with traditional antibody-drug conjugates, the antibody-drug conjugate targeting AXL obtained by using this coupling method has a narrow drug/antibody ratio (DAR) distributed. The structure of the AXL antibody-drug conjugate having the disubstituted maleimide linker is shown in Formula Ia or Ib:

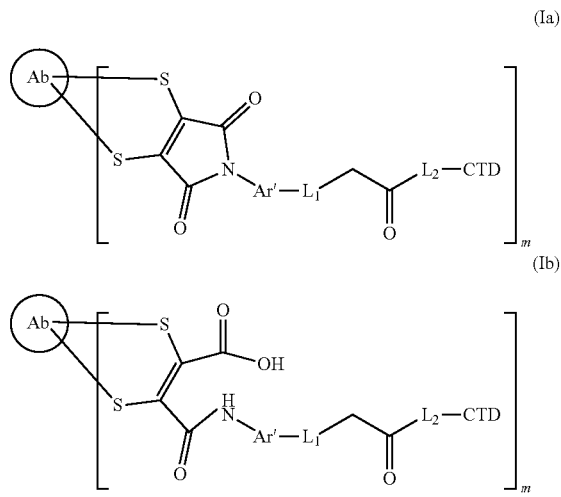

wherein,
Ar' is selected from the group consisting of substituted or unsubstituted C6-C10 arylene, and substituted or unsubstituted 5-12 membered heteroarylene;
$L_1$ is —O(CH$_2$CH$_2$O)$_n$— linked to the Ar' group, wherein n is selected from any integer from 1-20.
$L_2$ is a chemical bond, or AA-PAB structure; wherein AA is a polypeptide fragment consisted of 2-4 amino acids, and PAB is p-aminobenzylcarbamoyl;
CTD is a cytotoxic small molecule drug bonded to $L_2$ through an amide bond.
M is 3.8-4.2;
Ab is an antibody targeting AXL.

The present invention provides a coupling method that couples a small molecule toxin to an AXL targeting antibody through a specific linker, and greatly improves the tumor cell killing capability of the antibody without changing the affinity of the antibody.

The present invention provides a linker or coupling reagent, which comprises a diarylthio maleimide unit and a coupling group. The diarylthio maleimide unit is used for crosslinking with the inter-chain sulfhydryl of the antibody (upon reduction), while the coupling group is used to couple with the small molecule drug or a drug-linker unit. Compared to traditional ADCs with mono-dentate linker, the ADCs of the present invention are homogeneous and have stronger stability due to the bidentate binding between the diarylthio maleimide unit and the two sulfur atoms of the opened cysteine-cysteine disulfide bond in the antibody. Therefore, they will have an increased half-life in vivo, a reduced amount of systemically released cytotoxins, and safer drug properties than ADCs with mono-dentate linker.

In another aspect, the drug-linker units can be coupled to antibody via the linkers, producing partially inter-chain crosslinked conjugates. Compared to traditional ADCs, the antibody drug conjugates prepared by the method of the present invention have much narrower DAR distribution, and thus have greatly improved structural and pharmacological homogeneities. The antibody drug conjugates can be used in targeted delivery of drugs to cell populations of interest, for example, tumor cells. The antibody drug conjugates bind specifically to cell surface proteins, and the binding complex will be internalized rapidly into the cells.

The drug will be released in an active form and produce effects in cells. The antibody includes chimeric, humanized, or human antibody, antibody fragment that can bind to antigen; or Fc fused protein; or protein. The "drug" is a highly potent drug (see above), and can be polyethylene glycol in some case.

The conjugation product provided by the invention, albeit still a mixture, has a much narrower DAR-distribution, as compared to antibody drug conjugates produced traditionally. The average DAR obtained is close to 4, within an optimized DAR range of 2-4 of ADCs. In addition, the conjugation product does not contain or contain minimal naked antibodies (DAR=0), which are ineffective for cell killing. Also, the conjugation product does not contain heavily conjugated antibodies (DAR=8), which will be cleared more rapidly than those with low DAR values. As a result, the ADC product provided in the invention shows much improved homogeneity.

Preparation of AXL Antibody-Drug Conjugate

The preparation route of the antibody-drug conjugate is shown below. The disulfide bonds between antibody chains are reduced, resulting in 2n (such as 8) sulfhydryl groups. The substituted maleimide linker-drug conjugate (compound of formula Ic) of the present invention is cross-linked with the reduced antibody sulfhydryl group to generate the corresponding antibody-drug conjugate, wherein the antibody-drug conjugate exists as one or two of the forms as shown below.

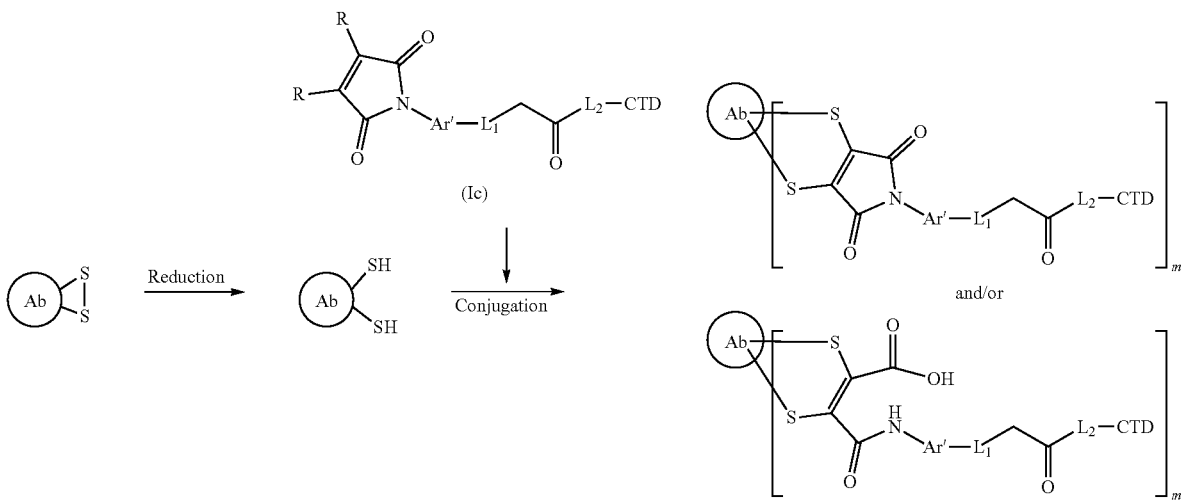

Wherein, the compound of formula Ic is selected from the group consisting of:

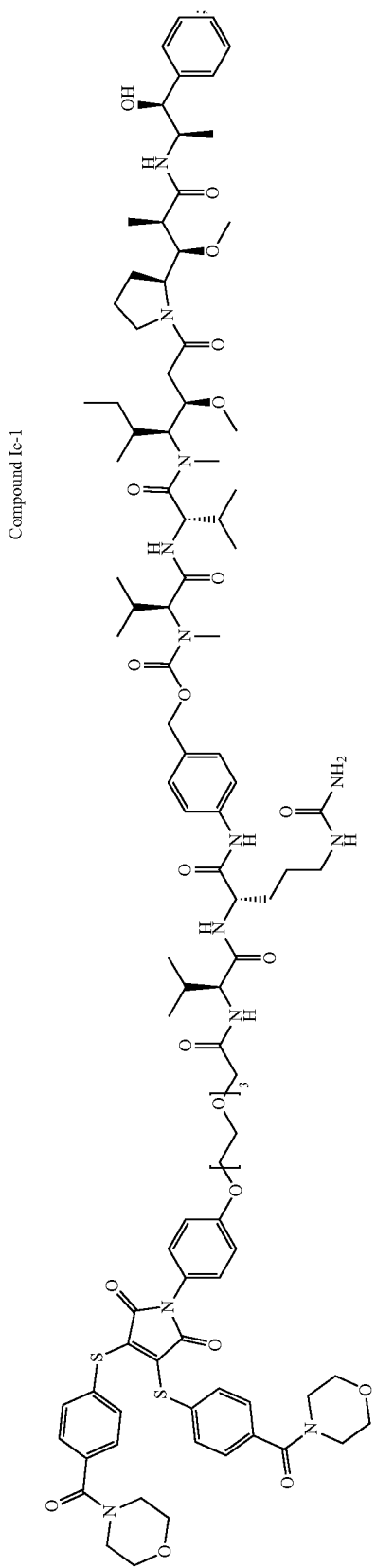
Compound Ic-1
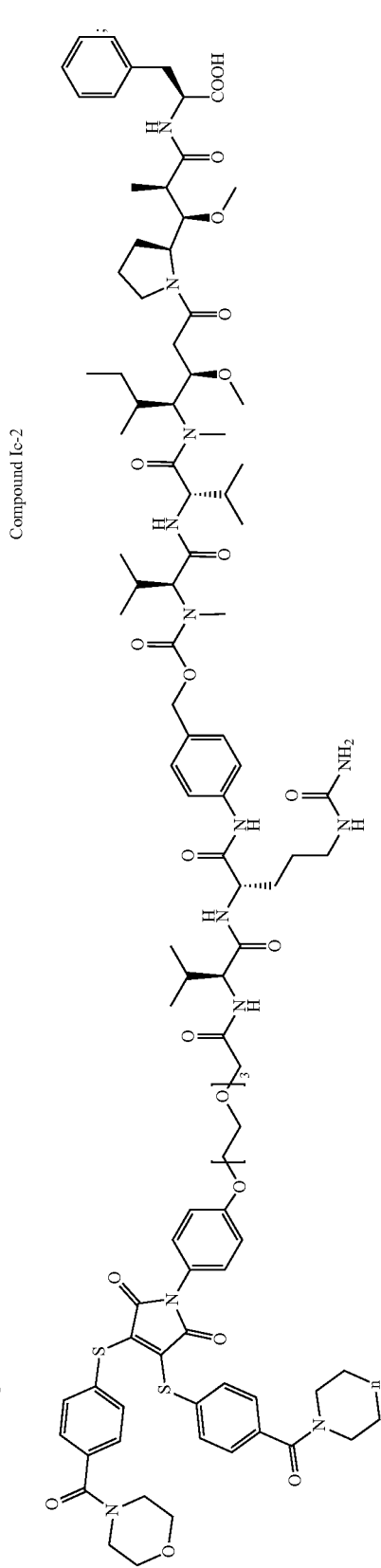
Compound Ic-2

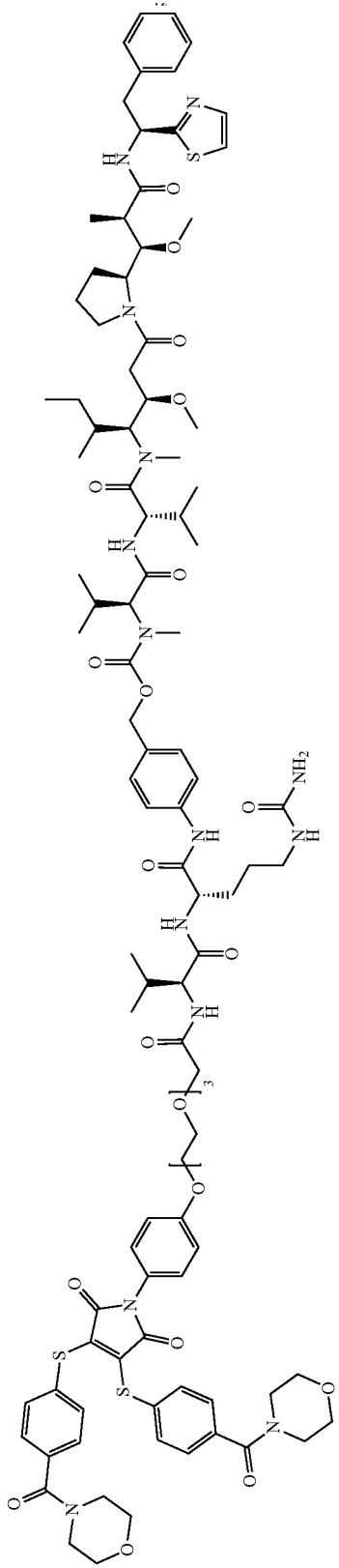
Compound Ic-3
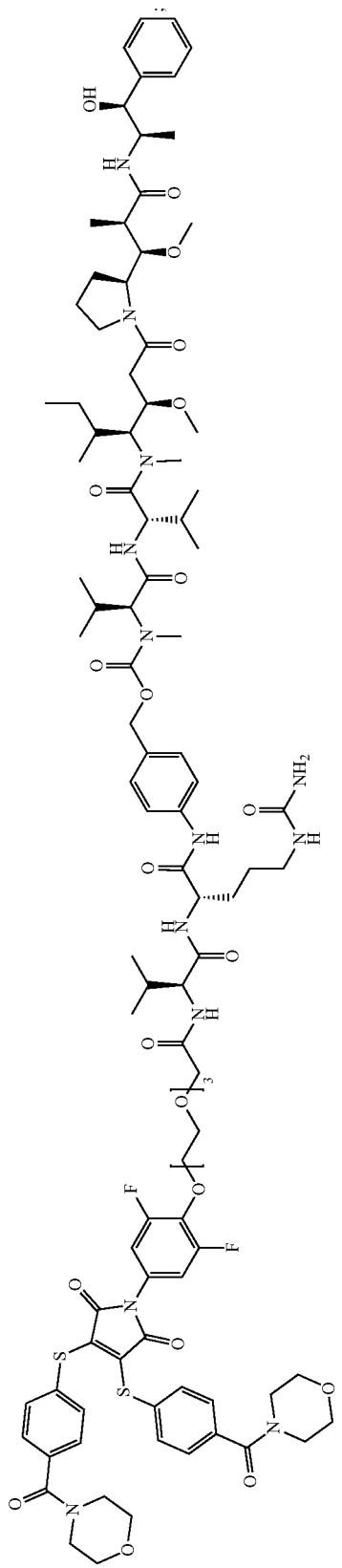
Compound Ic-4

-continued
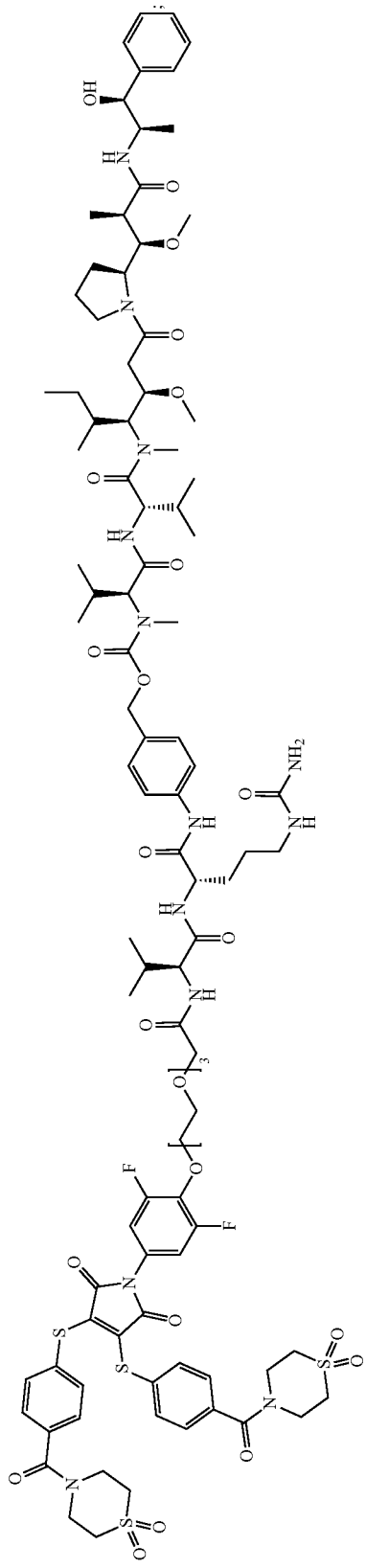
Compound Ic-5
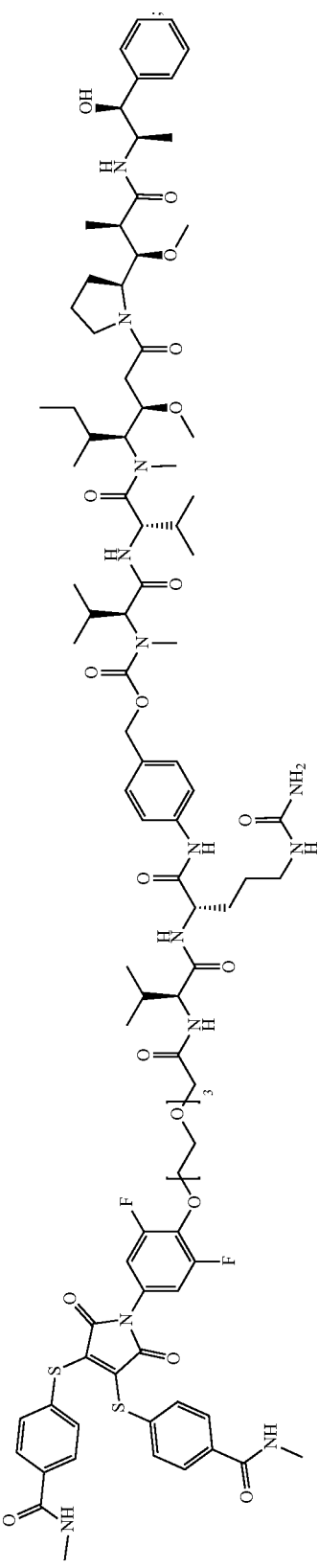
Compound Ic-6

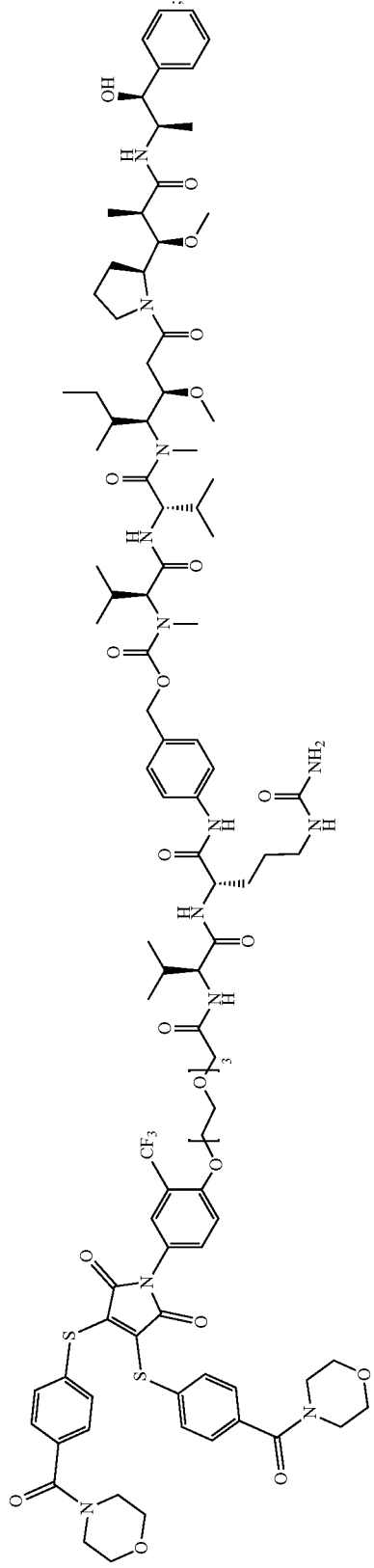
Compound Ic-7
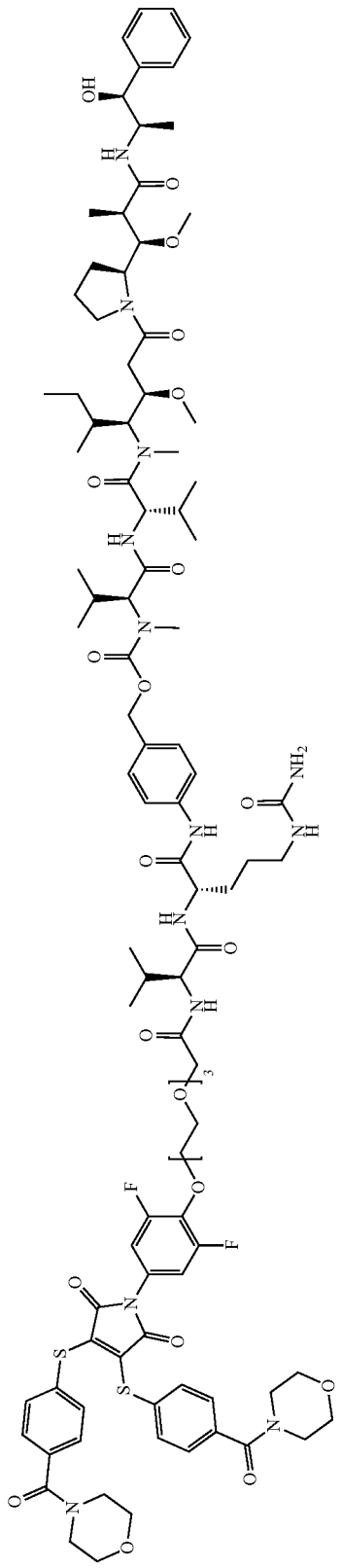
Compound Ic-8

A typical preparation method comprises: diluting the antibody stock solution to 2-10 mg/mL with reaction buffer, adding excess dithiothreitol (DTT) of 140-200 fold molar ratio, or adding excess tris(2-carboxyethyl)phosphine hydrochloride (TCEP) of 6.0-20 fold molar ratio, and stirring the reaction solution at 10-35° C. for 2-48 hours. The reaction buffer herein can be a buffer prepared in the following proportion 50 mM potassium dihydrogen phosphate-sodium hydroxide ($KH_2PO_4$—NaOH)/150 mM sodium chloride (NaCl)/1 mM diethylene triamine penlaacetic acid (DTPA), pH6-9; 50 mM disodium hydrogenphosphate-citric acid/150 mM sodium chloride (NaCl)/1 mM diethylene triamine penlaacetic acid (DTPA), pH 6-9; 50 mM boric acid-borax/150 mM sodium chloride (NaCl)/1 mM diethylene triamine penlaacetic acid (DTPA), pH 6-9; 50 mM histidine-sodium hydroxide/150 mM sodium chloride (NaCl)/1 mM diethylene triamine penlaacetic acid (DTPA), pH 6-9 and PBS/1 mM diethylene triamine penlaacetic acid (DTPA), pH 6-9.

The above reaction solution is cooled to 0-10° C. If DTT reduction is used, it is necessary to pass through a desalting column or ultrafiltration to remove excess DTT after the reduction reaction is completed. Then the substituted maleimide compounds (10 mg/ml, previously dissolved in acetonitrile (ACN), dimethylsulfoxide (DMSO), dimethylformamide (DMF) or diethylacetamide (DMA)) is added. It should be ensured that the volume ratio of the organic solvent in the reaction solution is no more than 15%. The coupling reaction is performed at 0-37° C. with stirring for 2-4 hours. If TCEP reduction is used, it is unnecessary to remove the remaining TCEP and the substituted maleimide compounds can be directly added for coupling.

The coupling reaction mixture is filtrated and purified by using a desalting column with sodium succinate/NaCl buffer or histidine-acetic acid/sucrose gel, and the peak samples are collected according to UV280 absorption value. Alternatively, ultrafiltration is performed for several times. After filtration and sterilization, the resultant product is stored at low temperature. The preferred temperature is −100 to −60° C., and the pore size of the filter device is preferably 0.15-0.3 microns.

The drug/antibody coupling ratio (DAR) of the obtained antibody-drug conjugate is relatively uniform. When the maleimide linker (linker moiety) with different substitutions of the present invention is used, the uniformity of ADC product is very high (usually, the DAR advantage product (such as DAR is about 4) accounts for at least 60%, at least 70%, at least 80%, at least 90% or higher of all ADCs). For ADCs with certain differences in DAR, if a sample with better uniformity is needed, the following non-limitative methods can be further used for separation and purification: hydrophobic interaction chromatography (HIC), sizs-exclusion chromatography (SEC), ion exchange chromatography (IEC).

Pharmaceutical Composition and Methods of Administration

The antibody-drug conjugate provided by the present invention can target a specific cell population and bind to a specific protein (antigen) on cell surface, thereby releasing the drug into the cell in an active form through endocytosis or drug infiltration of the conjugate. Therefore, the antibody-drug conjugate of the invention can be used to treat diseases of interest, and the antibody-drug conjugate mentioned above can be administered to a subject (e.g., a human) by a suitable route in a therapeutically effective amount. A subject in need of treatment can be a patient at risk of having or suspected of having a condition associated with the activity or amount of expression of a particular antigen. Such patients can be identified by routine physical examination.

Conventional methods, known to those of ordinary skill in the art of medicine, can be used to administer the pharmaceutical composition to the subject, depending upon the type of diseases to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or by infusion techniques. In addition, it can be administered to the subject via injectable depot routes of administration such as using 1-, 3-, or 6-month depot injectable or biodegradable materials and methods.

Injection compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

When the antibody drug conjugate as described herein is used as the therapeutic agent, it can be delivered in situ by methods conventional in the art. For example, it can be introduced into cells using liposomes, hydrogels, cyclodextrins, biodegradable nanocapsules, or bioadhesive microspheres. Alternatively, nucleic acids or vectors can be locally delivered by direct injection or by use of an infusion pump. Other methods include the use of various transport and carrier systems through the use of conjugates and biodegradable polymers.

The pharmaceutical composition of the present invention contains a safe and effective amount of the antibody-drug conjugate of the present invention and a pharmaceutically acceptable carrier. Such carriers include, but are not limited to, saline, buffer solution, glucose, water, glycerin, ethanol or the combination thereof. Usually the drug preparation should match the method of administration. The pharmaceutical composition of the present invention can be prepared in the form of liquores, for example, prepared by a conventional method using physiological saline or an aqueous solution containing glucose and other adjuvants. The pharmaceutical composition should be prepared under sterile conditions. The dosage of active ingredient is therapeutically effective amount.

The effective amount of the antibody-drug conjugate of the present invention may vary with the mode of administration and the severity of the disease to be treated. The selection of the preferred effective amount can be determined by a person of ordinary skill in the art according to various factors (for example, through clinical trials). The factors include but are not limited to: the pharmacokinetic parameters of the bifunctional antibody conjugate such as bioavailability, metabolism, half-life, etc.; the severity of the disease to be treated, the patient's weight, and the patient's immunity condition, route of administration, etc. Generally, when the antibody-drug conjugate of the present invention is administered at a dose of about 0.0001 mg-50 mg/kg animal body weight (preferably 0.001 mg-10 mg/kg animal body weight), satisfactory effects can be obtained. For example, due to the urgent need to treat the condition, several divided doses can be given every day, or the dose can be reduced proportionally.

The dosage form of the compound of the present invention for topical administration includes ointment, powder, patch, spray and inhalant. The active ingredient is mixed under sterile conditions with a physiologically acceptable carrier and any preservatives or buffer agents, or propulsive agents that may be required if necessary.

The compounds of the present invention can be administered alone or in combination with other pharmaceutically acceptable therapeutic agents.

When using the pharmaceutical composition, a safe and effective amount of the compound of the present invention is administered to a mammal (such as a human) in need of treatment, wherein the dosage of administration is the pharmaceutically effective dosage, and for a person weighing 60 kg, the daily dosage is usually 1 to 2000 mg, preferably 5 to 500 mg. Of course, the particular dose should also depend on various factors, such as the route of administration, patient healthy status, which are well within the skills of an experienced physician.

Use for Detection and Kit

The antibody or ADC thereof of the present invention can be used for detection, for example, for detecting samples, thereby providing diagnostic information.

In the present invention, the samples (sample) used include cells, tissue samples and biopsy specimens. The term "biopsy" used in the present invention shall include all kinds of biopsy known to those skilled in the art. Therefore, the biopsy used in the present invention may include, for example, excision samples of tumors, tissue samples prepared by endoscopic methods or organ puncture or needle biopsy.

The samples used in the present invention include fixed or preserved cell or tissue samples.

The present invention also provides a kit comprising the antibody (or fragment thereof) of the present invention. In a preferred embodiment of the present invention, the kit further includes a container, an instruction for use, buffer, and the like. In a preferred embodiment, the antibody of the present invention can be immobilized on a detection plate.

Application

The present invention further provides use of the antibody of the present invention, for example, for preparation of a diagnostic agent, or for preparation of a medicine for preventing and/or treating an AXL-related disease. The AXL-related disease includes tumorigenesis, tumor growth and/or metastasis, a tumor resistance-related disease, inflammation, a metabolism-related disease, etc.

Use of the antibody, ADC or CAR-T according to the present invention includes but is not limited to:
  (i) diagnosis, prevention and/or treatment of tumorigenesis, for tumor growth and/or metastasis, particularly, for a tumor with AXL high expression; wherein the tumor includes but is not limited to: breast cancer (e.g. triple negative breast cancer), lung cancer (such as non-small cell lung cancer), pancreatic cancer, malignant glioma, gastric cancer, liver cancer, esophageal cancer, kidney cancer, colorectal cancer, bladder cancer, prostate cancer, endometrial cancer, ovarian cancer, cervical cancer, leukemia, bone marrow cancer, angiosarcoma, etc.; preferably triple negative breast cancer, non-small cell lung cancer, pancreatic cancer, malignant glioma; and more preferably triple negative breast cancer and/or non-small cell lung cancer;
  (ii) diagnosis, prevention and/or treatment of an autoimmune disease; wherein the autoimmune disease includes (but are not limited to): systemic lupus erythematosus, rheumatoid arthritis, ulcerative colitis, type I diabetes, psoriasis, multiple sclerosis;
  (iii) diagnosis, prevention and/or treatment of inflammation; wherein the inflammation includes (but is not limited to): rheumatic arthritis, osteoarthritis, ankylosing spondylitis, gout, Lytle syndrome, psoriasis arthritis, infectious arthritis, tuberculous arthritis, viral arthritis, fungal arthritis, glomerular Nephritis, systemic lupus erythematosus, Crohn's disease, ulcerative colitis, acute lung injury, chronic obstructive pulmonary disease, and idiopathic pulmonary fibrosis;
  (iv) diagnosis, prevention and/or treatment of a metabolism-related disease, wherein the metabolism-related disease includes (but is not limited to): diabetes, diet-induced obesity, adipose inflammation.

The Main Advantages of the Present Invention Include:
1. The antibody described in the present invention has novel and excellent biological activity. Specifically, the preferred antibody has a very high affinity for AXL ($EC_{50}$ determined by ELISA was 0.04-0.05 nM). In addition, the preferred antibody has good binding affinity to AXL on the surface of tumor cells (the $EC_{50}$ determined by FACS was 0.07-0.14 nM), and can be used as a therapeutic antibody targeting AXL.
2. The humanized antibody of the present invention has not only activity comparable to or higher than that of murine antibody, but also lower immunogenicity.
3. The antibody-drug conjugate (ADC) of the present invention has specific AXL-dependent anti-tumor activity. The preferred humanized antibody drug conjugate (ADC) has no obvious toxic and side effects on cells with AXL-normal expression, but has extremely high killing activity on tumor cells with AXL high expression, and the $IC_{50}$ determined by cell proliferation inhibition test was 0.01 nM-0.05 nM.
4. The novel linker provided by the present invention can couple with an AXL-targeting antibody through a simple chemical method, and the DAR distribution of the AXL antibody-drug conjugate obtained by using the linker is very narrow as compared with conventional coupling ways. Therefore, the resulting product has high homogeneity. The obtained cross-linked product has a single distribution (with a DAR of 4) which accounts for more than 80%. Compared with traditional cVC-PAB cross-linked product, the cross-linked product has improved or comparable inhibitory activity on tumor cell proliferation in vitro, the biological activity, safety and other proprietary properties.
5. The disulfide bond linkage based on maleimide of the present invention has better stability. The introduction of substituent at Ar' position can adjust the reaction rate of maleimide ring opening hydrolysis and slow down the secondary hydrolysis of cyclization of ring opened maleimide. And sulfhydryl exchange and secondary hydrolysis of cyclization after ring opening are less likely to occur, which further strengthens the stability of the AXL antibody-drug conjugate in vitro and in vivo.
6. Compared with AXL07-vc-MMAE in the prior art, the preferred antibodies and antibody-drug conjugates of the present invention have better anti-tumor therapeutic effects in vitro and in vivo.

The present invention will be further illustrated below with reference to the specific examples. It is to be understood that these examples are for illustrative purposes only and are not intended to limit the scope of the invention. For the experimental methods in the following examples, in which the specific conditions are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Unless indicated otherwise, parts and percentage are weight parts and weight percentage. The cell strain is a conventional commercially available product or purchased from ATCC, and the plasmids are all commercially available products.

Example 1 Discovery and Preparation of Monoclonal Antibodies Targeting Human AXL Step (1), Preparation of Hybridoma Cells:

First, the extracellular domain of human AXL protein (AXL-ECD) was prepared as an antigen. Refer to NCB: By referring to the amino acids at positions 33 to 449 in NP_068713.2, C-terminus polyhistidine-tagged antigen was obtained using gene cloning technology and mammalian vector expression system, the specific amino acid sequence was as follows (SEQ ID NO. 36):

QAEESPFVGNPGNITGARGLTGTLRCQLQVQGEPPEVHWLRDGQILELAD

STQTQVPLGEDEQDDWIVVSQLRITSLQLSDTGQYQCLVFLGHQTFVSQP

GYVGLEGLPYFLEEPEDRTVAANTPFNLSCQAQGPPEPVDLLWLQDAVPL

ATAPGHGPQRSLHVPGLNKTSSFSCEAHNAKGVTTSRTATITVLPQQPRN

LHLVSRQPTELEVAWTPGLSGIYPLTHCTLQAVLSDDGMGIQAGEPDPPE

EPLTSQASVPPHQLRLGSLHPHTPYHIRVACTSSQGPSSWTHWLPVETPE

GVPLGPPENISATRNGSQAFVHWQEPRAPLQGTLLGYRLAYQGQDTPEVL

MDIGLRQEVTLELQGDGSVSNLTVCVAAYTAAGDGPWSLPVPLEAWRPGQ

AQPVHQLVKEPSTPAFSWPHHHHHHHHHH

The above human AXL extracellular domain protein expressed and prepared in HEK293T cells was used to immunize Balb/c mice with a dosage of 50 μg/mouse to prepare immunized splenocytes. Mouse myeloma cells (SP2/0) and feeder cells were prepared at an appropriate time for fusion.

After the above three kinds of cells were prepared, the fusion of splenocytes with SP2/0 cells was mediated by PEG. PEG was then removed, and the resultant cells were re-suspended in HAT complete medium containing feeder cells, and were seeded and cultured in a 96-well plate. Positive wells were screened by ELISA/FACS. Finally, the cells in the positive wells were subjected to clonal culture by using limited dilution method, and the cells, which had a high titer, were in a good morphology and grew in a monoclonal manner, were screened by ELISA or FASCS. The cells were further subjected to subcloning screening until the positive cloning rate was 100% for three consecutive screening. Then the cell line was subjected to amplification and library construction.

Step (2), Purification of Murine Monoclonal Antibody Targeting Human AXL:

The hybridoma cells selected in step (1) were expanded and cultured in a roller bottle for 14 days, then the cell culture supernatant was collected and filtered through a 0.22 μm filter membrane. Subsequently, the obtained culture supernatant was added to the pre-balanced Protein A resin column at a constant rate, and the column was equilibrated with 0.1M Tris-HCl (PH=8.0, containing 1.5M NaCl). Then the balance column was eluted with 0.1M sodium citrate buffer, and the eluate was collected and quantified, and subjected to SDS-PAGE electrophoresis, SEC-HPLC and endotoxin detection. The purified antibodies obtained were subpackaged and stored at −80° C. for later use.

Steps (3), Detection of Biological Activity and Specificity of the Murine Monoclonal Antibody Targeting Human AXL:

After repeated screening, the biological activity and target specificity of the selected 6 hybridoma monoclonal antibodies were determined. As shown in FIG. 1A, the culture supernatant of the monoclonal cell was detected by a Fluorescence Activated Cell Sorter (FACS). All 6 monoclonals could specifically bind to human MDA-MB-231 cells with AXL high expression (AXL-P), but had no obvious binding activity to MDA-MB-453 cells with AXL low expression (AXL-N). As shown in FIG. 1B, the purified antibody samples were used for subtype detection, wherein mAb001 to mAb005 were all identified as IgG1/k, and mAb006 was IgG2b/k.

Step (4), the purified antibody samples were used for ELISA detection after gradient dilution. As shown in Table-1, mAb001 to mAb006 had excellent binding affinity to AXL-ECD, wherein the $EC_{50}$ of mAb001, mAb002, mAb005 and mAb006 were all <0.1 nM.

TABLE 1

| Activity of the original murine antibodies targeting human AXL by ELISA | |
|---|---|
| original Murine antibody | AXL-ECD ELISA $EC_{50}$ (nM) |
| mAb001 | 0.073 |
| mAb002 | 0.063 |
| mAb003 | 0.459 |
| mAb004 | 0.232 |
| mAb005 | 0.092 |
| mAb006 | 0.093 |

Example 2 Antibody Sequencing and Identification of Complementarity Determining Regions (CDRs)

Figure 2:
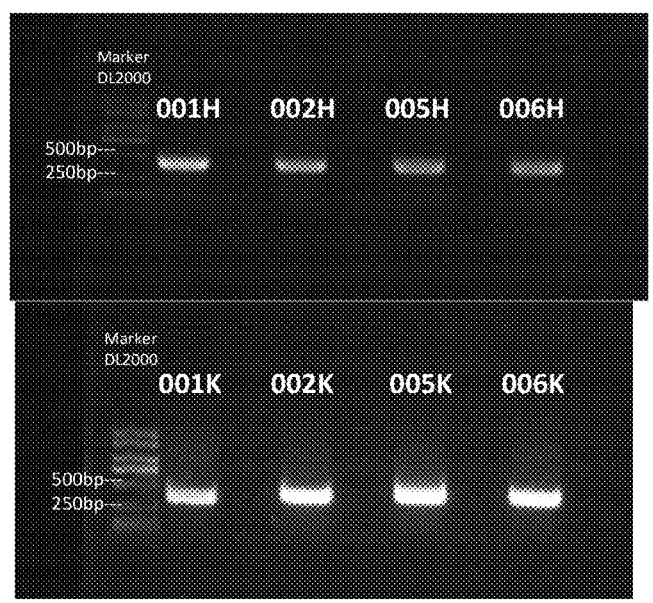
FIG. 2 shows the results of agarose gel electrophoresis of PCR amplified heavy chain variable region (VH) and light chain variable region (VL) fragments of mAb001, mAb002, mAb005 and mAb006. VH/VL fragments are used to clone and assemble human-mouse chimeric antibody expression vector after sequencing and identification.

Based on their excellent specificity and affinity, mAb001, mAb002, mAb005 and mAb006 were preferentially selected for antibody sequencing and identification. Primers were designed to amplify heavy chain (VH) and light chain (VL) variable region fragments by conventional PCR technology (see FIG. 2). The fragments were cloned into vector and sequenced. Using routine sequencing and Kabat database analysis (www.bioinf.org.uk), the following amino acid sequences of heavy chain variable region (VH) and light chain variable region (VL), and the information of complementarity determining region (CDR) were obtained (The amino acid sequence of CDR-1/2/3 were shown by underline). After gene sequencing, it was noticed that the CDR sequences of mAb006c and mAb005c were highly similar, and were not listed separately.

amino acid sequence of heavy chain variable
region (VH) of mAb002
                                  SEQ ID NO. 7
QIQLQQSGPELVKPGASVKISCKASGYPFTDFYINWVKQKPGQGLEWIG

WIYPGSGNTKYNEKFKGKATLTVDTSSSTAYMQLSSLTSEDTAVYFCAR

STGFFDYWGQGTTLTVSS amino acid sequence of heavy chain variable
region (VH) of mAb005
                                  SEQ ID NO. 15
QVQLQQSGPELVKPGASVKISCKASGYSFTSYYIHWVQQRPGQGLEWIG

WIYPGSDNTKYNEKFKDKATLTADTSSGTAYMQLSSLTSDDSAVFYCAR

NYYDYDGGTWFPYWGQGTLVTVSA amino acid sequence of heavy chain variable
region (VH) of mAb001
                                  SEQ ID NO. 23
AVQLQESGPSLVKPSQTLSLTCSVTGDSITSGYWSWIRKFPGNKLESMG

YMTYSGATYYNPSLKSRISITRDTSKNQYYLQLNSVTPEDTATYYCAR

GGNSYFFDYWGQGTTLTVSS amino acid sequence of light chain variable
region (VL) of mAb002
                                  SEQ ID NO. 8
QIVLTQSPALMSASPGEKVTMTCSASSSIGYMYWYQQKPRSSPKSWIY

LTSNLASGVPARFSGSGSGTSYSLTISSMEAEDAATYYCQQWSSNPPT

FGAGTKLELK amino acid sequence of light chain variable
region (VL) of mAb005
                                  SEQ ID NO. 16
DIQMTQTTSSLSASLGDRVTISCRASQDINYYLNWYQQKPDGTVKLLIY

YTSRLHSRVPSRFSGSGSGTDYSLTISNLEQEDIATYFCQQGNTLPWTF

GGGTKLEIK amino acid sequence of light chain variable
region (VL) of mAb001
                                  SEQ ID NO. 24
DIQMTQSPASLSVSVGETVTITCRASENIYSNLAWYQLKQGKSPHLLVY

AATNLADGVPSRFSGSGSGTQYSLKIISLQSEDFGTYYCQHFWGTPLTF

GAGTKLELK

Example 3 Preparation of Human-Mouse Chimeric Antibodies

Figure 3:
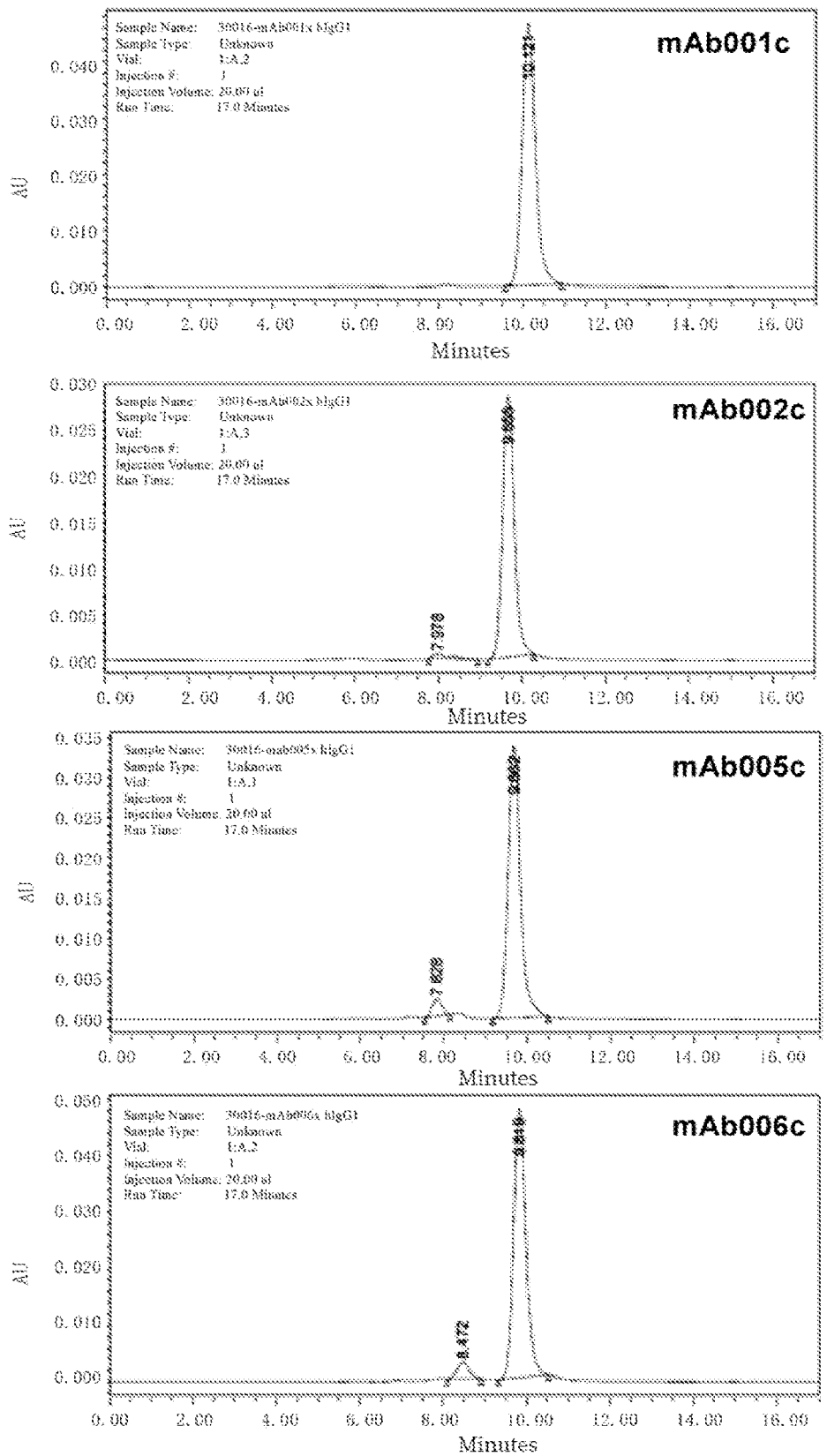
FIG. 3 shows the purification profile of four human-mouse chimeric antibodies mAb001c, mAb002c, mAb005c and mAb006c expressed by HEK293T cells using the MabSelect™ SuRe™ column.

Using gene recombination technology, 3 sets of variable region sequences (see SEQ ID NO. 7, SEQ ID NO. 15, SEQ ID NO. 23, SEQ ID NO. 8, SEQ ID NO. 16 and SEQ ID NO. 24) were cloned into a vector containing recombinant heave chain constant region and Kappa chain constant region of human IgG1. The vector was confirmed to be correct by sequencing, and then the constructed chimeric antibodies were expressed and purified using transfection technology and mammalian expression system (FreeStyle™ 293T cells) (see FIG. 3). The number, heavy chain and light chain components of the obtained human-mouse chimeric antibodies are listed in Table 2. The humanized antibody AXL07 disclosed in the invention patent application CN201580045131.4 was prepared by the same method and used as a control.

TABLE 2

| Preparation of human-mouse chimeric antibody | | |
|---|---|---|
| Chimeric Antibody | VH SEQ ID NO: | VL SEQ ID NO: |
| mAb001c | 7 | 8 |
| mAb002c | 15 | 16 |
| mAb005c | 23 | 24 |
| mAb006c | Not marked | Not marked |
| AXL107 | 37 | 38 |

Example 4 ELISA Determination of the Affinities of Chimeric Antibodies to Human AXL Protein The extracellular domain of AXL protein (AXL-ECD) was diluted to 1 μg/mL with the coating solution, and coated onto ELISA plate with 100 μL/well at 4° C. overnight. The excess antigen was washed off. The plate was blocked with 1% BSA at room temperature for 2 h, then each monoclonal antibody in a 3-fold dilution was added at 100 □L/well. The plate was incubated at room temperature for 1 h; the unbound antibody was washed off, and appropriate concentration of anti-mouse secondary antibody labeled with horseradish peroxidase was added at 100 μL/well. The plate was incubated at room temperature for 0.5 h. The unbound secondary antibody was washed off. TMB Substrate was added and reacted for about 15 minutes. 1N HCL was added at 50 μL/well to stop the color reaction. Then the absorbance was measured at 450 nm and the obtained data was analyzed.

Figure 4:
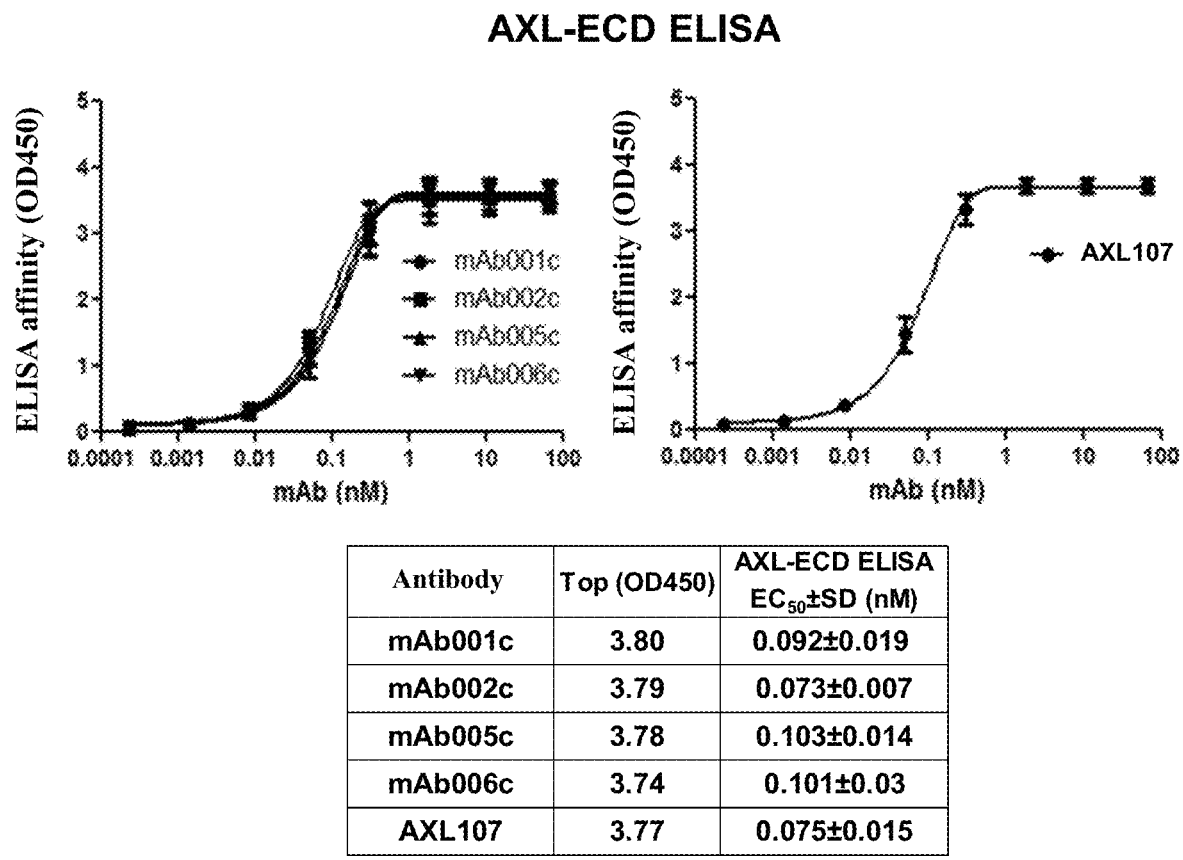
FIG. 4 shows the binding affinity $EC_{50}$ of human-mouse chimeric antibodies mAb001c, mAb002c, mAb005c and mAb006c to AXL-ECD as detected by ELISA.

The detection results are shown in FIG. 4. mAb001c, mAb002c, mAb005c and mAb006c had a strong affinity to AXL-ECD. The specific $EC_{50}$ values are shown in Table-3. The affinity of mAb002c to AXL-ECD was slightly higher than that of control antibody AXL107.

TABLE 3

| activity of chimeric antibodies by ELISA | | |
|---|---|---|
| Chimeric antibody | Highest reading (OD450 nm) | AXL-ECD ELISA $EC_{50}$ ± SD (nM) |
| mAb001c | 3.80 | 0.092 ± 0.019 |
| mAb002c | 3.79 | 0.073 ± 0.007 |
| mAb005c | 3.78 | 0.103 ± 0.014 |
| mAb006c | 3.74 | 0.101 ± 0.03 |
| AXL107 | 3.77 | 0.075 ± 0.015 |

Example 5 AXL Protein was Highly Expressed in a Variety of Tumor Cells

Figure 5:
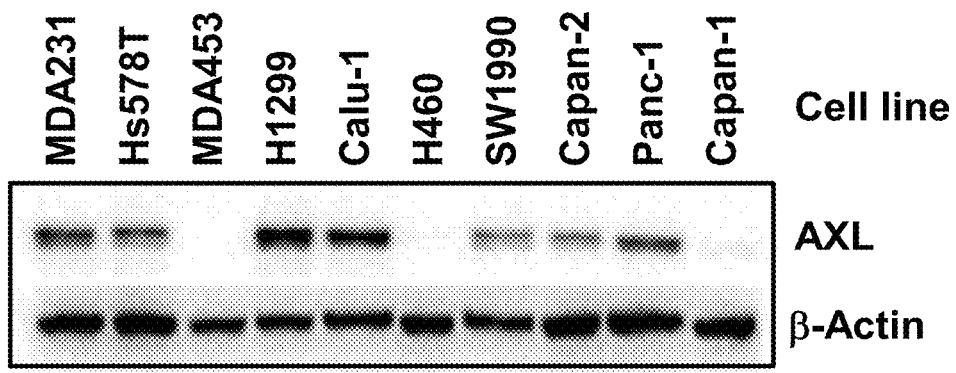
FIG. 5 shows the expression levels of AXL protein in cell lines of breast cancer (MDA231, Hs587T and MDA453), lung cancer (NCI-H1299, Calu-1 and NCI-H460) and pancreatic cancer (SW1990, Capan-2, Panc-1 and Capan-2) as detected by Western blot.

The total cell proteins of a variety of different molecular classification of breast cell lines (MDA-MB-231, Hs578T and MDA-MB-453), lung cancer cell lines (NCI-H1299, Calu-1 and NCI-H460), pancreatic cancer cell lines (SW1990, Capan-2, Panc-1 and Canpan-1) were prepared and accurately quantified, and then the expression level of AXL protein was detected by Western blot. The results are shown in FIG. 5. AXL protein was abnormally activated and expressed in most of the tested breast cancer, lung cancer and pancreatic cancer cell lines.

Example 6 Gene Expression Analysis of Human Tumor and Normal Tissues with Database By downloading the gene expression information in CCLE (Cancer cell line encyclopedia) database, G-Tex (human normal tissue) database, and database of 51 human breast cancer cell lines (Neve R M et al., Cancer Cell 2006; 10: 515-27), the expression levels of AXL mRNA in tumor strain groups (such as breast cancer, lung cancer, glioma, and melanoma) relative to that in human normal tissues were analyzed. The expression levels of AXL mRNA in breast cancers of different molecular classification (for example, luminal-type vs. basal-type) and lung cancers of different malignancies (for example, epithelial vs. interstitial) were also analyzed and compared in this example.

Figure 6:
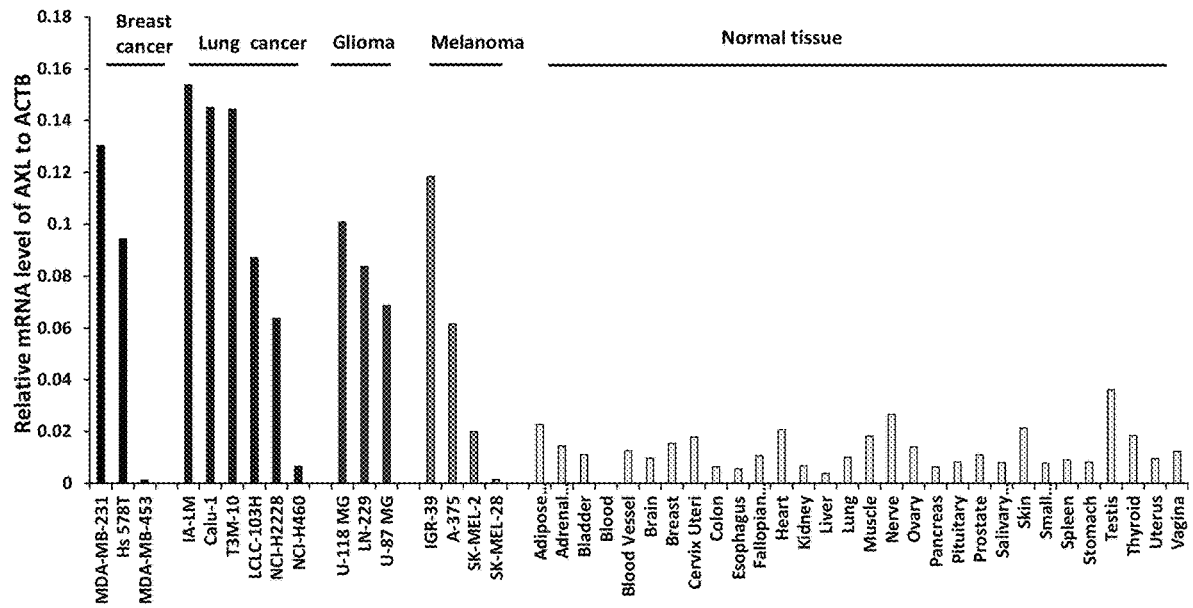
FIG. 6 shows the analysis and comparison of AXL mRNA expression levels (ratio to □-actin) in multiple tumor cell lines (breast cancer, lung cancer, glioma and melanoma) and human normal tissues.

The results are shown in FIG. 6. By comparing CCLE database and G-Tex database, the average AXL mRNA expression levels in highly invasive breast cancer, lung cancer, glioma and melanoma cell lines were significantly higher than that in normal tissues. The AXL-targeted antibody of the present invention will have significant effects in the applications of diagnosis, prevention and treatment of triple negative breast cancer, lung cancer, and glioma.

Figure 7:
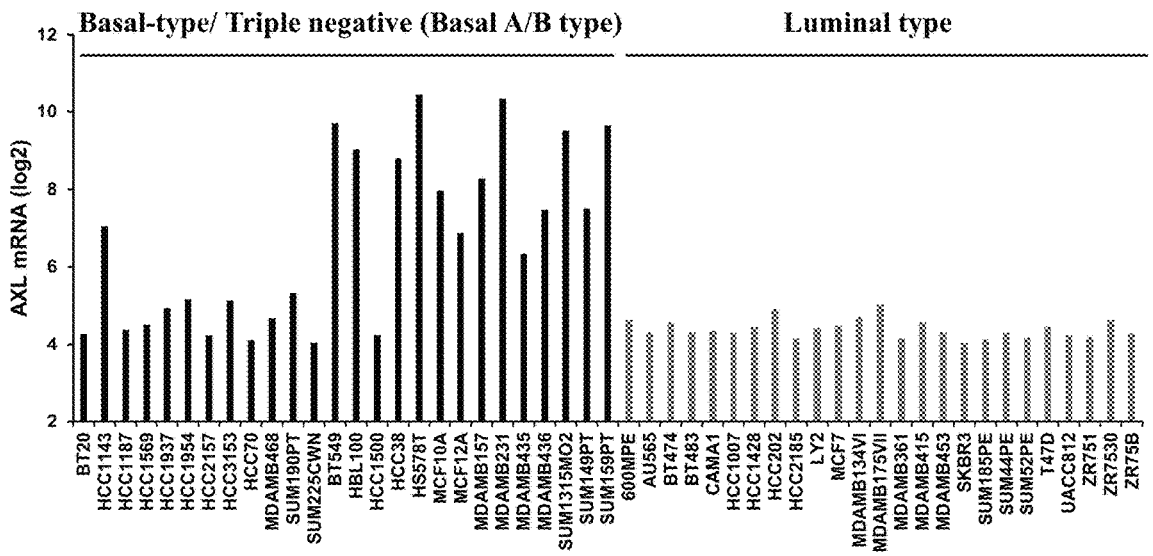
FIG. 7 shows the analysis of expression levels of AXL mRNA in the highly invasive and highly metastatic Basal-type vs. Luminal-type breast cancer cell line in the gene expression database of 51 human breast cancer cell lines (Neve R M et al., Cancer Cell 2006; 10:515-27).

The results are shown in FIG. 7. The average AXL mRNA expression level in the highly invasive and highly metastatic basal-type breast cancer cell line was significantly higher than that in the Luminal-type breast cancer cell line, and the results had statistical significance. In view of the fact that basal-type breast cancer is the main source of clinically "triple negative" breast cancer, the AXL-targeted antibody of the present invention will have a more significant effect in the applications of diagnosis, prevention and treatment of triple negative breast cancer.

Figure 8:
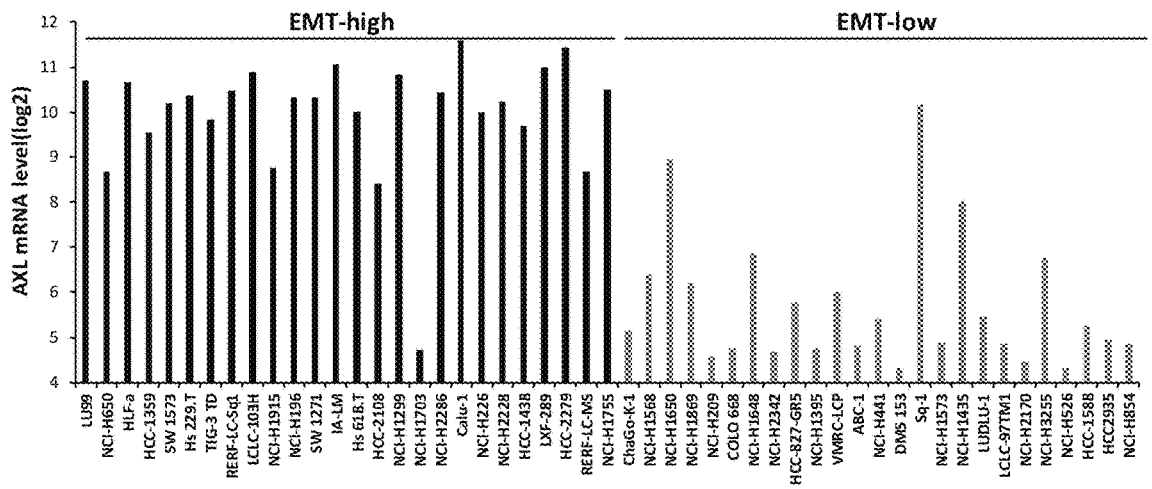
FIG. 8 shows the analysis of the expression levels of AXL mRNA in the epithelial vs. interstitial lung cancer cell lines in the CCLE database.

The results are shown in FIG. 8. The average AXL mRNA expression level in the highly metastatic/interstitial (EMT-high) lung cancer cell line was significantly higher than that in the low metastatic/epithelial (EMT-low) lung cancer cell lines, and the results had statistical significance. In view of the fact that highly metastatic lung cancer is clinically resistant and has a poor prognosis, the AXL-targeted antibody of the present invention will have a more significant effect in the applications of diagnosis and treatment of highly metastatic, resistant and advanced lung cancer.

Example 7 FACS Detection of Specific Binding of AXL Protein on Tumor Cell Surface to Chimeric Antibodies AXL-high-expression non-small cell lung cancer cells NCI-1299, LCLC-103H and Calu-1, high-expression triple negative breast cancer cells MDA-MB-231 and Hs578T, and AXL-low-expression breast cancer cells MDA-MB-453 were used as target cells to determine the binding of chimeric antibody mAb002c to AXL on the cell surface. $3\times10^5$ tumor cells were mixed well with the antibody (final concentration was 5 μg/mL), and then incubated at 4° C. for 1 hour. The cells were washed twice with PBS to remove unbound primary antibody. Then 200 μL (2 μg/mL) PE-labeled secondary antibody was added and incubated at 4° C. for 30 min. The cells were washed twice with PBS to remove unbound secondary antibodies. Finally, the cells were resuspended in 200 μL PBS. The Binding affinity of the tested antibody to AXL on the cell surface or the overall binding fluorescence intensity (MFI) of different tumor cells at the same antibody concentration was determined with a flow cytometer (FACSCalibur).

Figure 9:
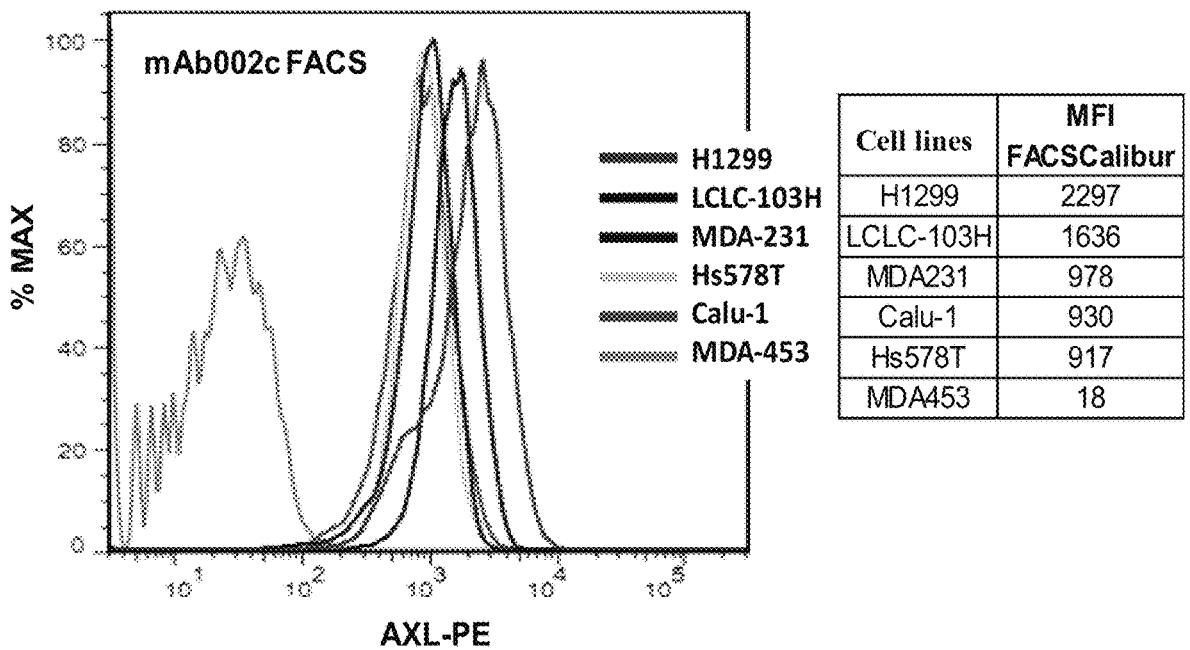
FIG. 9 shows the binding levels of mAb002c (5 □g/mL) to AXL on the surface of tumor cells with AXL high expression (NCI-H1299, LCLC-103H, CaLu-1, MDA-MB-231 and Hs578T) or AXL low expression (MDA-MB-453).

The detection results are shown in FIG. 9. The chimeric antibody mAb002c could specifically recognize and bind tumor cells with AXL high expression. The order of fluorescence intensity of binding rate were NCI-H1299, LCLC-103H, MDA-MB-231, and Hs578T. The tumor cells MDA-MB-453 with AXL low expression showed weak binding fluorescence intensity. By comparing the binding rate (MFI) of NCI-H1299 and LCLC-103H with antibody to the binding rate of MDA-MB-453 with antibody, the differences of binding rates for mAb002c were 127 and 91 times, respectively.

Example 8 Determination of the Binding Affinities of Chimeric Antibodies to AXL on the Surface of Tumor Cells AXL-high-expression triple negative breast cancer cells MDA-MB-231 were used as target cells. 100 μL of the test antibody diluted in a 3-fold gradient from 200 nM to 0.091 nM was used as primary antibody, and mixed with $1\times10^5$ MDA-MB-231 suspended in 100 μL RPMI-1640 serum-free medium, respectively. Then the obtained solutions were incubated at 4° C. for 1 h, the cells were washed twice with PBS to remove unbound primary antibody, and then the target cells were incubated with 200 μL PE-labeled secondary antibody (2 μg/mL) at 4° C. for 30 min. The cells were washed twice with PBS to remove unbound secondary antibody. Finally, the cells were resuspended in 200 μL PBS, and the binding affinity of the test antibody to AXL on the cell surface was determined by a flow cytometer (FACSCalibur)

Figure 10:
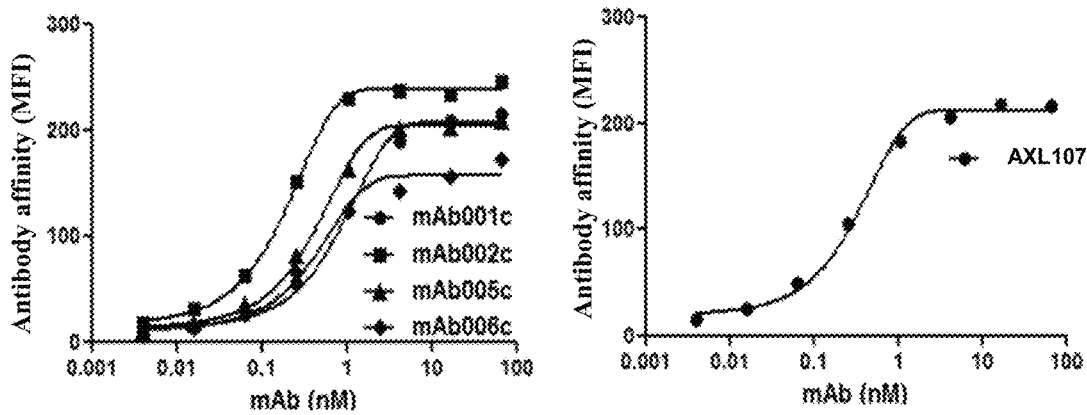
FIG. 10 shows the test results of binding affinity $EC_{50}$ of chimeric antibodies mAb001c, mAb002c, mAb005c and mAb006c to AXL on the surface of MDA-MB-231 cells, wherein $1 \times 10^5$ cells were mixed with the antibody of a concentration gradient as shown, and then detected and analyzed by FACS after incubation for 1 hour using a flow cytometer (FACSCalibur).

The detection results are shown in FIG. 10 and Table-4. mAb001c, mAb002c, mAb005c and mAb006c had strong affinities to MDA-MB-231 cells, wherein the affinity of mAb002c to MDA-MB-231 cells was significantly higher than that of the control antibody AXL107.

TABLE 4

Binding activity of chimeric antibodies to MDA-MB-231 cells

| Chimeric antibody | Highest MFI value (FACSCalibur) | Mean $EC_{50}$ (nM) |
|---|---|---|
| mAb001c | 216.94 | 0.840 |
| mAb002c | 242.32 | 0.174 |
| mAb005c | 208.46 | 0.400 |
| mAb006c | 168.52 | 0.477 |
| AXL107 | 217.93 | 0.433 |

AXL-high-expression lung cancer cells NCI-H1299 were used as target cells. 100 μL of the test antibody diluted in a 3-fold gradient was used as primary antibody, and mixed with $1\times10^5$ NCI-H1299 cells suspended in 100 μL RPMI-1640 serum-free medium. The operation method was the same as above. Finally, the cells were resuspended in 200 μL PBS, and the binding affinity of the tested antibody to AXL on the cell surface was determined by a flow cytometer (FACSAria II).

Figure 11:
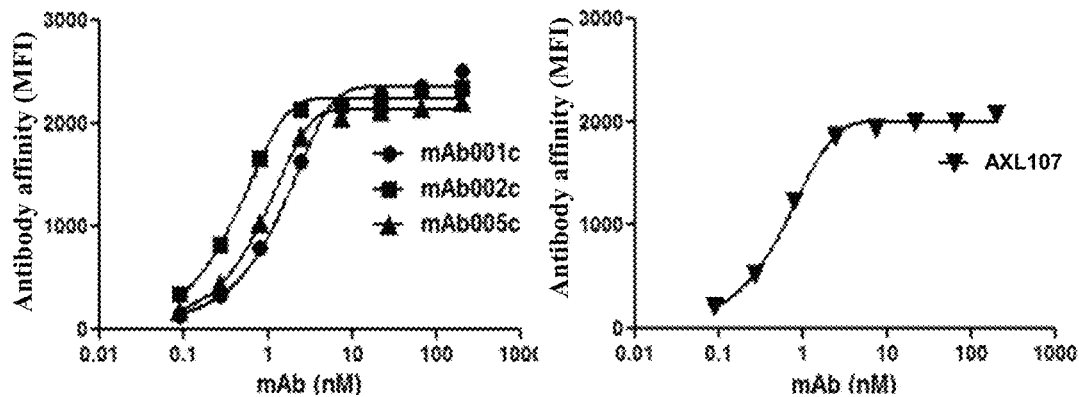
FIG. 11 shows the test results of binding affinity $EC_{50}$ of chimeric antibodies mAb001c, mAb002c and mAb005c to AXL on the surface of NCI-H1299 cells, wherein $1 \times 10^5$ cells were mixed with the antibody of a concentration gradient as shown, and then detected and analyzed by FACS after incubation for 1 hour using a flow cytometer (FACSAria II).

The detection results are shown in FIG. 11 and Table-5. mAb001c, mAb002c, mAb005c and mAb006c had strong affinities for NCI-H1299 cells, wherein the affinity of mAb002c to NCI-H1299 cells was significantly higher than that of the control antibody AXL107.

TABLE 5

Binding activity of chimeric antibodies to NCI-H1299 cells

| Chimeric antibody | Highest MFI value (FACSAria II) | EC$_{50}$ (nM) |
|---|---|---|
| mAb001c | 2366.33 | 1.487 |
| mAb002c | 2259.67 | 0.4564 |
| mAb005c | 2136.33 | 0.9076 |
| AXL107 | 2006.67 | 0.6547 |

Example 9 Preparation of Humanized Antibodies

The humanized templates that best matched mAb002 non-CDR regions were searched and selected from the Germline database, and then the CDR regions of the antibody were transplanted to the selected humanized templates, and the CDR regions of the human template were replaced, and then the obtained sequences were recombined with IgG1 constant region. Meanwhile, based on the three-dimensional structure of the murine antibody, the embedded residues which directly interacted with the CDR regions and had an important influence on the conformation of VL and VH were back mutated.

Specifically, by humanization of mAb002c, 3 humanized heavy chain variable regions (SEQ ID NO. 25, SEQ ID NO. 26 and SEQ ID NO. 27), and 8 humanized light chain variable regions (SEQ ID NO. 28, SEQ ID NO. 29, SEQ ID NO. 30, SEQ ID NO. 31, SEQ ID NO. 32, SEQ ID NO. 33, SEQ ID NO. 34 and SEQ ID NO. 35) were obtained.

mAb002_VHg0
SEQ ID NO. 25
QVQLVQSGAEVKKPGASVKVSCKASGYPFTDFYINWVRQAPGQGLEWMG
WIYPGSGNTKYNEKFKGRVTMTRDTSISTAYMELSRLRSDDTAVYYCAR
STGFFDYWGQGTLVTVSS mAb002_VHg1
SEQ ID NO. 26
QVQLVQSGAEVKKPGASVKVSCKASGYPFTDFYINWVRQAPGQGLEWMG
WIYPGSGNTKYNEKFKGRVTLTVDTSISTAYMELSRLRSDDTAVYYCAR
STGFFDYWGQGTLVTVSS mAb002_VHg2
SEQ ID NO. 27
QVQLVQSGAEVKKPGASVKVSCKASGYPFTDFYINWVKQAPGQGLE
WIGWIYPGSGNTKYNEKFKGRVTLTVDTSISTAYMELSRLRSDDTAVYY
CARSTGFFDYWGQGTLVTVSS mAb002_VKg0
SEQ ID NO. 28
EIVLTQSPATLSLSPGERATLSCSASSSIGYMYWYQQKPGQAPRLLIY
LTSNLASGIPARFSGSGSGTDFTLTISSLEPEDFAVYYCQQWSSNPPT
FGQGTKLEIK mAb002_VKg1
SEQ ID NO. 29
EIVLTQSPATLSLSPGERATLSCSASSSIGYMYWYQQKPGQAPRLLIY
LTSNLASGIPARFSGSGSGTDYTLTISSLEPEDFAVYYCQQWSSNPPT
FGQGTKLEIK mAb002_VKg2
SEQ ID NO. 30
EIVLTQSPATLSLSPGERATLSCSASSSIGYMYWYQQKPGQSPRSLIY
LTSNLASGIPARFSGSGSGTDYTLTISSLEPEDFAVYYCQQWSSNPPT
FGQGTKLEIK mAb002_VKg3
SEQ ID NO. 31
QIVLTQSPATLSLSPGERATLSCSASSSIGYMYWYQQKPGQSPRSLIY
LTSNLASGIPARFSGSGSGTDYTLTISSLEPEDFAVYYCQQWSSNPPT
FGQGTKLEIK mAb002_VKg4
SEQ ID NO. 32
EIVLTQSPDFQSVTPKEKVTITCSASSSIGYMYWYQQKPDQSPKLLIK
LTSNLASGVPSRFSGSGSGTDFTLTINSLEAEDAATYYCQQWSSNPPT
FGQGTKLEIK mAb002_VKg5
SEQ ID NO. 33
EIVLTQSPDFQSVTPKEKVTITCSASSSIGYMYWYQQKPDQSPKLLIY
LTSNLASGVPSRFSGSGSGTDYTLTINSLEAEDAATYYCQQWSSNPPT
FGQGTKLEIK mAb002_VKg6
SEQ ID NO. 34
EIVLTQSPDFQSVTPKEKVTITCSASSSIGYMYWYQQKPDQSPKSLIY
LTSNLASGVPSRFSGSGSGTDYTLTINSLEAEDAATYYCQQWSSNPPT
FGQGTKLEIK mAb002_VKg7
SEQ ID NO. 35
QIVLTQSPDFQSVTPKEKVTITCSASSSIGYMYWYQQKPDQSPKSLIY
LTSNLASGVPSRFSGSGSGTDYTLTINSLEAEDAATYYCQQWSSNPPT
FGQGTKLEIK

The designed humanized variable region sequence was cloned into a vector containing human IgG1 heavy chain constant region and Kappa chain constant region by using gene recombination technology. The vector was confirmed to be correct by sequencing, and then the constructed humanized antibodies were expressed using transfection technology and mammalian expression system (FreeStyle™ 293T cells). These humanized heavy and light chains were combined and expressed, respectively. Finally, in the mAb002c group, 24 humanized antibodies were obtained. The corresponding heavy and light chain combinations of each antibody are shown in following Table-6.

TABLE 6

Preparation of humanized antibodies

| Humanized antibody name | VH SEQ ID NO: | VL SEQ ID NO: |
|---|---|---|
| Hu002-1 | 25 | 28 |
| Hu002-2 | 26 | 28 |
| Hu002-3 | 27 | 28 |
| Hu002-4 | 25 | 29 |
| Hu002-5 | 26 | 29 |
| Hu002-6 | 27 | 29 |
| Hu002-7 | 25 | 30 |
| Hu002-8 | 26 | 30 |

TABLE 6-continued

Preparation of humanized antibodies

| Humanized antibody name | VH SEQ ID NO: | VL SEQ ID NO: |
|---|---|---|
| Hu002-9 | 27 | 30 |
| Hu002-10 | 25 | 31 |
| Hu002-11 | 26 | 31 |
| Hu002-12 | 27 | 31 |
| Hu002-13 | 25 | 32 |
| Hu002-14 | 26 | 32 |
| Hu002-15 | 27 | 32 |
| Hu002-16 | 25 | 33 |
| Hu002-17 | 26 | 33 |
| Hu002-18 | 27 | 33 |
| Hu002-19 | 25 | 34 |
| Hu002-20 | 26 | 34 |
| Hu002-21 | 27 | 34 |
| Hu002-22 | 25 | 35 |
| Hu002-23 | 26 | 35 |
| Hu002-24 | 27 | 35 |

Example 10 Binding Affinities of Humanized Antibodies to AXL-ECD 24 humanized antibodies in Table-6 were diluted by gradient, and their affinity to AXL-ECD protein was determined by ELISA. The experimental method was referred to Example 4.

Figure 12:
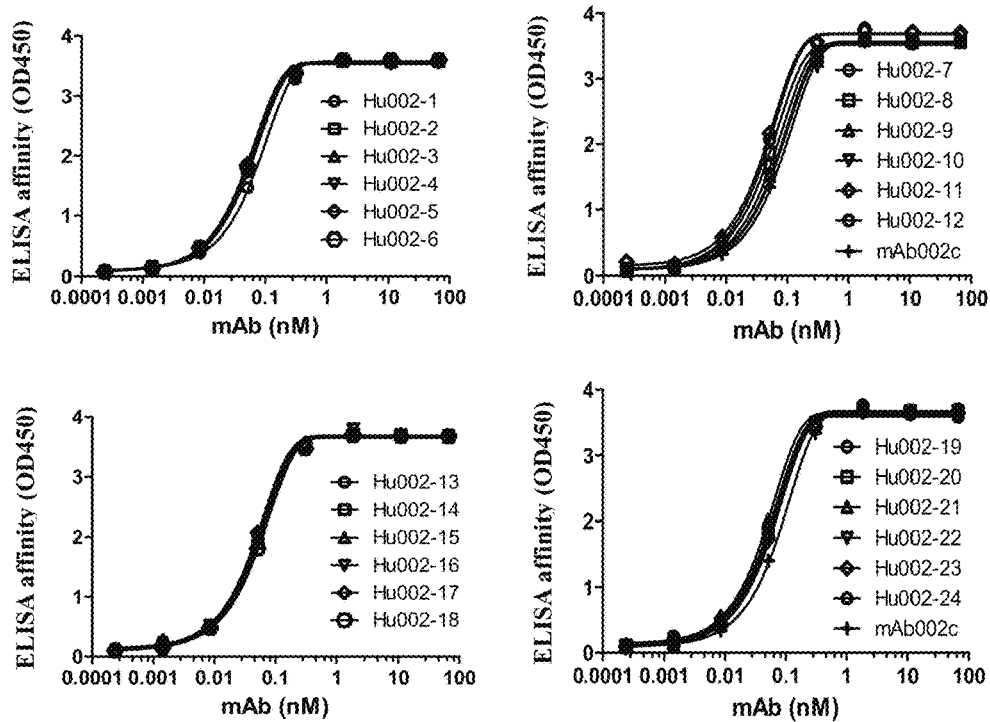
FIG. 12 shows the binding affinity $EC_{50}$ of a series of humanized antibodies (Hu002-1 to Hu002-24) to AXL-ECD as detected by ELISA.

Experimental results are shown in FIG. 12 and Table-7. The humanized antibodies Hu002c-1 to Hu002c-24 all had strong binding affinities to AXL-ECD protein, and the $EC_{50}$ values were 0.043 nM-0.082 nM.

TABLE 7 activity of humanized antibodies by ELISA

| Humanized antibody number | TOP (OD450) | AXL-ECD ELISA $EC_{50}$ (nM) |
|---|---|---|
| mAb002c | 3.58 | 0.076 |
| Hu002-1 | 3.62 | 0.070 |
| Hu002-2 | 3.60 | 0.055 |
| Hu002-3 | 3.60 | 0.048 |
| Hu002-4 | 3.60 | 0.055 |
| Hu002-5 | 3.59 | 0.050 |
| Hu002-6 | 3.63 | 0.052 |
| Hu002-7 | 3.59 | 0.058 |
| Hu002-8 | 3.59 | 0.049 |
| Hu002-9 | 3.62 | 0.067 |
| Hu002-10 | 3.58 | 0.068 |
| Hu002-11 | 3.74 | 0.043 |
| Hu002-12 | 3.73 | 0.045 |
| mAb002c | 3.64 | 0.082 |
| Hu002-13 | 3.73 | 0.047 |
| Hu002-14 | 3.72 | 0.052 |
| Hu002-15 | 3.72 | 0.050 |
| Hu002-16 | 3.76 | 0.047 |
| Hu002-17 | 3.71 | 0.045 |
| Hu002-18 | 3.71 | 0.055 |
| Hu002-19 | 3.73 | 0.059 |
| Hu002-20 | 3.71 | 0.054 |
| Hu002-21 | 3.71 | 0.046 |
| Hu002-22 | 3.67 | 0.059 |
| Hu002-23 | 3.69 | 0.057 |
| Hu002-24 | 3.65 | 0.051 |

Example 11 Binding Affinities of Humanized Antibodies to Tumor Cell AXL 24 humanized antibodies in Table-6 were diluted by gradient, and their affinities to AXL, on the surface of MDA-MB-231 cells were determined by flow cytometer. The experimental method was referred to Example 8.

Figure 13:
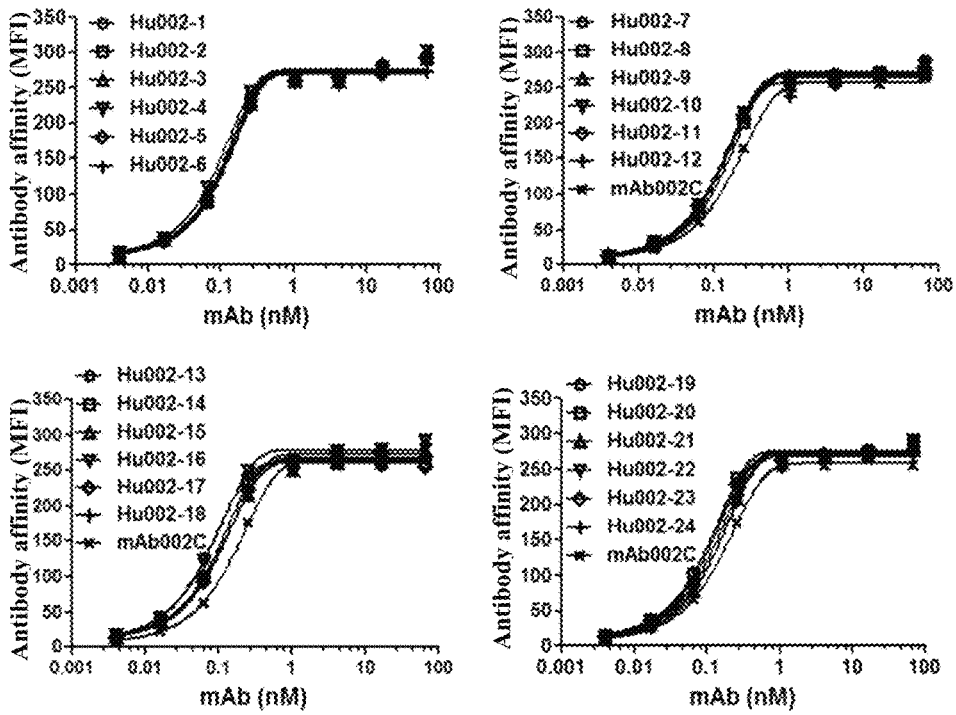
FIG. 13 shows the test results of binding affinity $EC_{50}$ of a series of humanized antibodies (Hu002-1 to Hu002-24) to AXL on the surface of MDA-MB-231 cells, wherein $1 \times 10^5$ cells were mixed with the antibody of a concentration gradient as shown, and then detected and analyzed by FACS after incubation for 1 hour using a flow cytometer (FACSCalibur).

Experimental results are shown in FIG. 13 and Table-8. The humanized antibodies had very high binding affinities to AXL on the surface of MDA-MB-231 cells, and the $EC_{50}$ values were 0.073 nM-0.17 nM, indicating that their affinities were higher than that of the control AXL107 (0.43 nM).

TABLE 8

Binding activity of humanized antibodies to MDA-MB-231 cells

| Humanized antibody Number | Highest MFI value (FACSCalibur) | $EC_{50}$ (nM) |
|---|---|---|
| mAb002c | 261.52 | 0.160 |
| Hu002-1 | 277.17 | 0.101 |
| Hu002-2 | 277.59 | 0.112 |
| Hu002-3 | 276.72 | 0.108 |
| Hu002-4 | 276.70 | 0.090 |
| Hu002-5 | 274.51 | 0.114 |
| Hu002-6 | 270.65 | 0.101 |
| Hu002-7 | 275.28 | 0.129 |
| Hu002-8 | 270.10 | 0.138 |
| Hu002-9 | 268.17 | 0.121 |
| Hu002-10 | 272.85 | 0.118 |
| Hu002-11 | 271.10 | 0.123 |
| Hu002-12 | 261.48 | 0.116 |
| mAb002c | 269.90 | 0.169 |
| Hu002-13 | 262.13 | 0.073 |
| Hu002-14 | 263.73 | 0.094 |
| Hu002-15 | 267.78 | 0.099 |
| Hu002-16 | 281.56 | 0.082 |
| Hu002-17 | 269.21 | 0.107 |
| Hu002-18 | 277.17 | 0.111 |
| Hu002-19 | 277.76 | 0.121 |
| Hu002-20 | 277.46 | 0.099 |
| Hu002-21 | 272.85 | 0.132 |
| Hu002-22 | 276.49 | 0.134 |
| Hu002-23 | 275.74 | 0.098 |
| Hu002-24 | 261.69 | 0.098 |

4 humanized antibodies in Table-6 were diluted by gradient, and their affinities to AXL on the surface of LCLC-103H cells were determined by flow cytometer. The experimental method was referred to Example 8.

Figure 14:
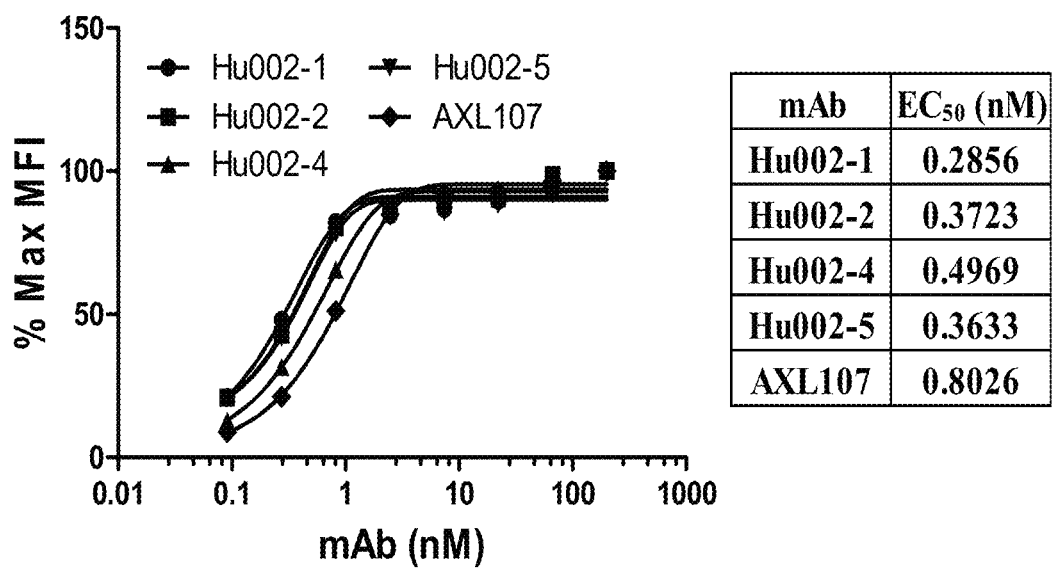
FIG. 14 shows the test results of binding affinity $EC_{50}$ of a series of humanized antibodies (Hu002-1 to Hu002-5) to AXL on the surface of LCLC-103H cells, wherein 1×10⁵ cells were mixed with the antibody of a concentration gradient as shown, and then detected and analyzed by FACS after incubation for 1 hour using a flow cytometer.

Experimental results are shown in FIG. 14. The humanized antibodies Hu002-1, Hu002-2, Hu002-4 and Hu002-5 had very high binding affinities to AXL on the surface of LCLC-103H cells, and the $EC_{50}$ values were 0.28 nM, 0.37 nM, 0.49 nM, 0.36 nM, respectively. The results indicated that their affinities were higher than that of the control AXL107 (0.80 nM).

Example 12 Binding of Humanized Antibodies to Tumor Cells Leads to Internalization to Intracellular Lysosome The AXL-high-expression breast cell line MDA-MB-231 was used as target cells. MDA-MB-231 cells of 50% density were spread in a laser confocal culture dish and cultured for 16 hours. Then 5 μg/mL (diluted in 1640 medium containing 10% Fetal calf serum) anti-AXL humanized antibody Hu002-2 was added and respectively incubated in 37° C. for 4 hours or 4° C. for 1 hour (as a control). The cells were washed three times with PBS to remove the antibodies unbound to the cells, and immobilized with 4% paraformaldehyde (diluted in PBS) at room temperature for 30 minutes. The cells were washed three times with PBS and permeabilized with 0.4% Triton X-100 (diluted in PBS) at room temperature for 10 minutes. The cells were washed three times with PBS, and the Lamp-2 (rabbit anti-human) antibody was used to incubate at 37° C. for 1 hour to mark the position of cell lysosome. The unbound antibodies were washed off with PBS, and R-PE-labeled goat anti-human and Alexa 488 secondary antibodies were added and incubated at 37° C. for 30 min. The unbound secondary antibodies were washed off with PBS, the cells were stained with DAPI for 10 minutes to mark the position of the nucleus, and the antibody endocytosis situation was observed with a Fluorescence microscope (Leica, 20×).

Figure 15:
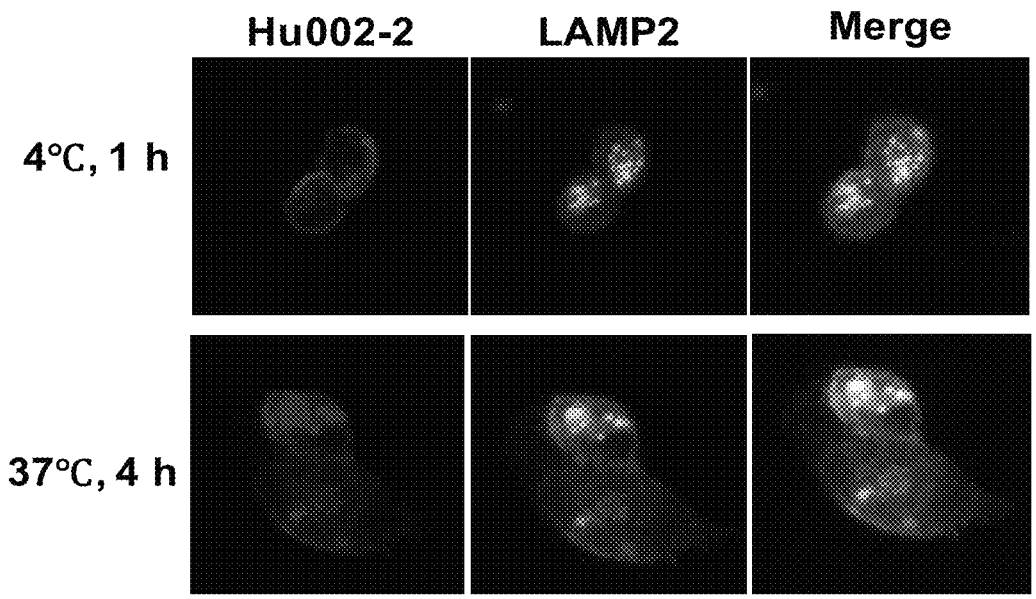
FIG. 15 shows that the binding of Hu002 to MDA-MB-231 cells results in internalization to intracellular lysosome. The antibodies (5 μg/mL) were incubated with the cells at 4° C. for 1 hour, or at 37° C. for 4 hours, and then placed in a laser scanning confocal microscope to observe the results.

The results are shown in FIG. 15. Hu002-2 could be quickly and largely endocytosed by MDA-MB-231 cells into lysosome. The results indicate that the antibody of the present invention is suitable for preparing antibody-drug conjugates (ADC), suggesting that AXL-ADC will have good ADC drug properties and showing prospects as broad-spectrum and highly specific drugs for treatment of AXL-positive tumors.

Example 13 Binding of Humanized Antibodies to Tumor Cells LED to a Decrease in AXL Protein Expression Level in Tumor AXL-high-expression lung cancer cells LCLC-103H were used as target cells, and spread in a 12-well plate at 16% confluence. After 16 hours of adherent culture, the medium was changed to serum-free medium containing PBS, 2 μg/mL of subtype control hIgG1, Hu002-2, or antibody-drug conjugate (ADC) Hu002-2-BL20-MMAE (prepared in Example 15 below), respectively, with two wells for each. Protein samples were collected after incubation of 24 hours and 48 hours, respectively. The changes in AXL protein expression in cells were detected by western blotting.

Figure 16:
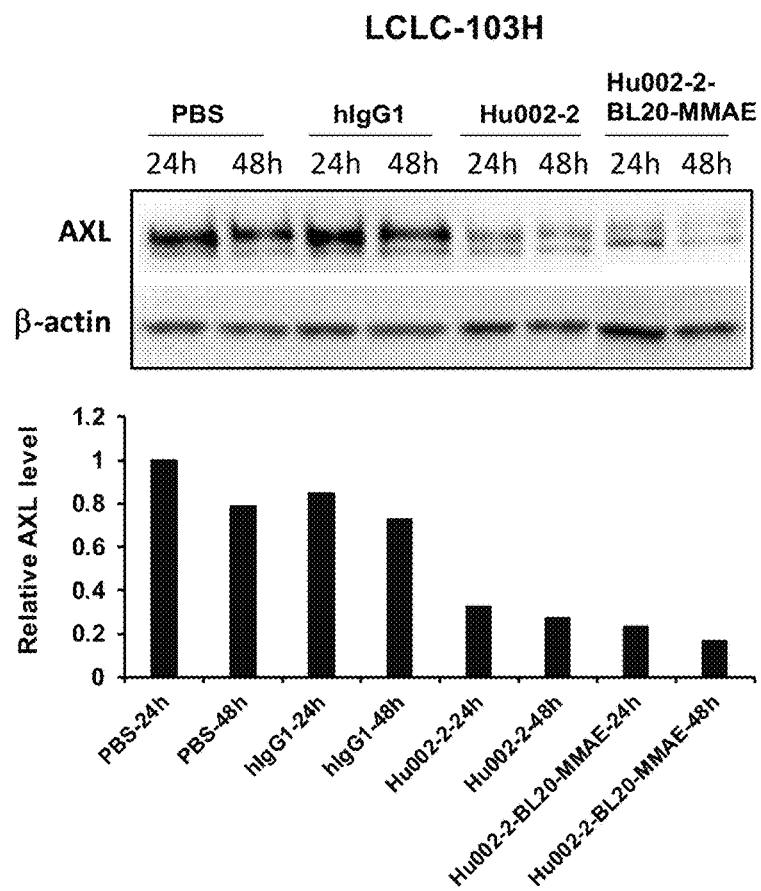
FIG. 16 shows that inhibiting effect on AXL protein expression in LCLC-103H cells treated with Hu002-2 or Hu002-2-BL20-MMAE for 24 or 48 hours as detected by Western blot.

The results are shown in FIG. 16. After the administration of PBS or hIgG1, there was no significant change in the overall AXL expression of the cells. However, after the administration of Hu002-2 or its ADC, the AXL expression in LCLC-103H cells was significantly down-regulated. It was caused by the binding of antibodies or ADCs to cells and their degradation in the lysosome after endocytosis.

Example 14 Preparation of AXL107-Vc-MMAE and AXL107-BL20-MMAE

PBS/EDTA (pH=7.4) buffer was added into the stock solution of humanized antibody AXL107 targeting AXL to make the concentration at 20 mg/ml, and the antibody was reduced with 2.6 eq of TCEP at 25° C. for 2 hours. The obtained solution was cooled on ice, added with 6.0 eq of mc-VC-PAB-MMAE (purchased from Shanghai Haoyuan Chemical Co., LTD, pre-dissolved in DMA) without purification, and reacted for 1 hour at 0° C. Then cysteine was added to stop the reaction. The excess small molecules were removed using a G25 desalting column, and the obtained product was placed into 20 mM citrate-sodium citrate/6% sucrose buffer (pH 6.6), sterilized through a filter device of 0.22 micron pore and preserved at −80° C. The obtained antibody conjugate was named AXL107-vc-MMAE.

Figure 17:
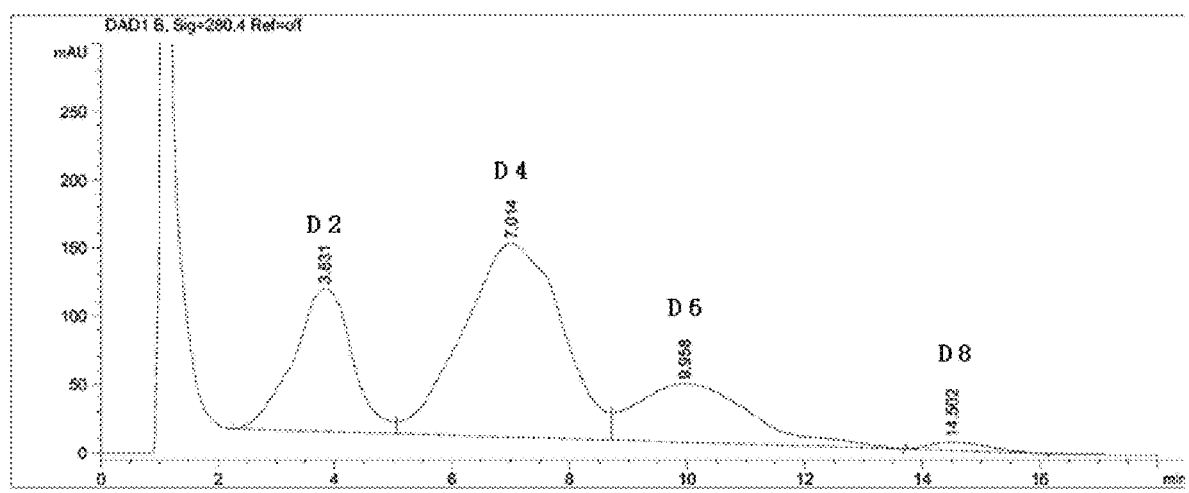
FIG. 17 shows the hydrophobic interaction chromatography (HIC) profile of the antibody-drug conjugate AXL107-vc-MMAE.
Figure 19:
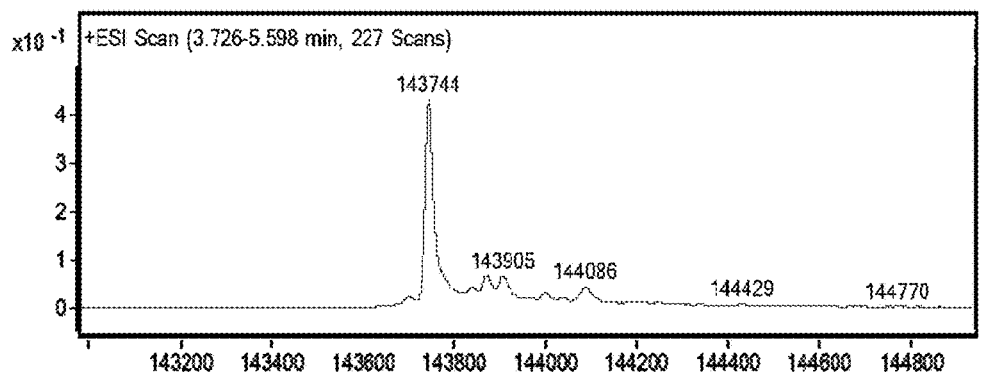
FIG. 19 shows the mass spectrum profile of the monoclonal antibody AXL107.
Figure 20:
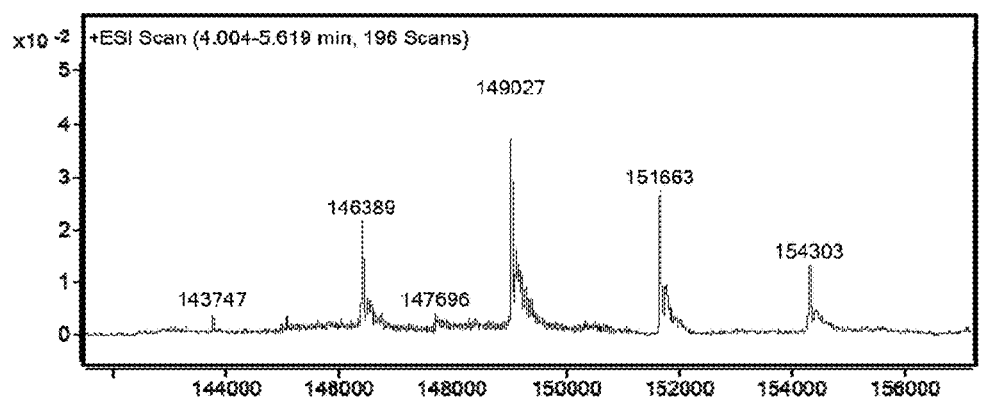
FIG. 20 shows the mass spectrum profile of the antibody-drug conjugate AXL107-vc-MMAE.

The results are shown in FIGS. 17, 19 and 20. The mass spectrum graph of humanized antibody AXL107 (FIG. 19) and the HIC and mass spectrum graph of its antibody conjugate AXL107-vc-MMAE (FIG. 17 and FIG. 20) all showed that the antibody AXL107 was conjugated to form the antibody conjugate AXL107-vc-MMAE. The molecular weight of the conjugate was consistent with the expected value, and the average DAR value was about 4.0.

The stock solution of antibody AXL107 was replaced with 50 mM sodium dihydrogen phosphate-disodium hydrogen phosphate ($NaH_2PO_4$—$Na_2HPO_4$)/150 mM sodium chloride (NaCl)/2 mM ethylenediaminetetraacetic acid (EDTA) reaction buffer (pH 7.0), to make the concentration at 10 mg/mL. Tris(2-carboxyethyl)phosphine hydrochloride (TCEP) in a 10-fold excess molar ratio was added, and the reaction solution was stirred at 25° C. for 4 hours. The excess TCEP were removed using a G25 desalting column. An appropriate amount of diethyl acetamide (DMA) was added to the collected reduction antibodies. Then Compound Ic-4 (10 mg/ml, pre-dissolved in DMA) in a 6-fold excess molar ratio was added, ensuring that the volume of DMA in the reaction system did not exceed 10%. The obtained solution was stirred at 20° C. for 2.0 hours for coupling. The coupling reaction mixture was filtrated and purified by a desalting column with pH 7.5 Tris-hydrochloric acid/sucrose gel filtration, and peak samples were collected according to the UV280 absorption value. Then the peak samples were sterilized through a filter device of 0.22 micron pore, preserved at −80° C. The obtained antibody conjugate was named AXL107-BL20-MMAE.

Figure 18:
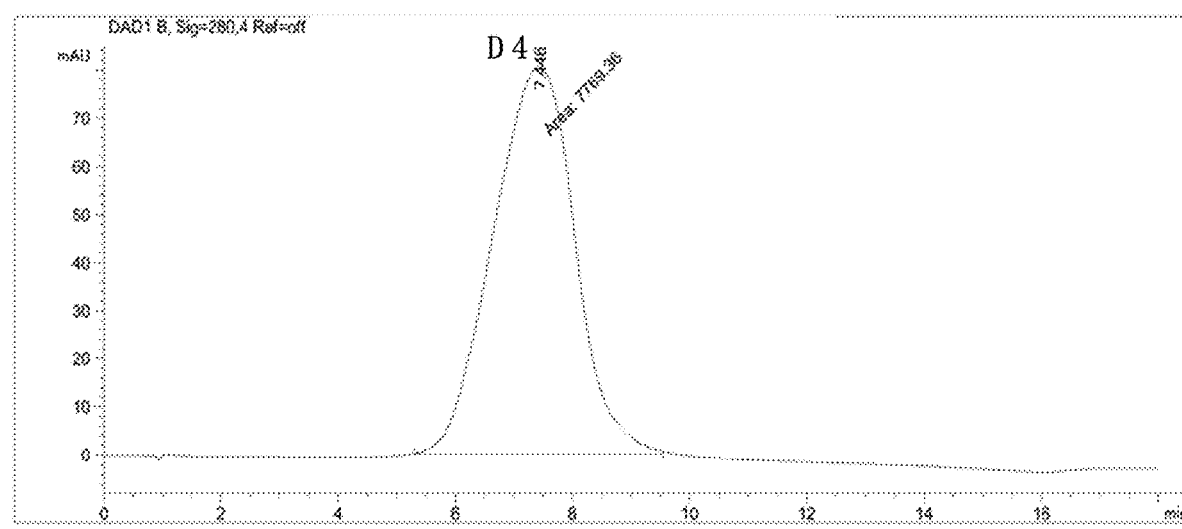
FIG. 18 shows the hydrophobic interaction chromatography (HIC) profile of the antibody-drug conjugate AXL107-BL20-MMAE.
Figure 21:
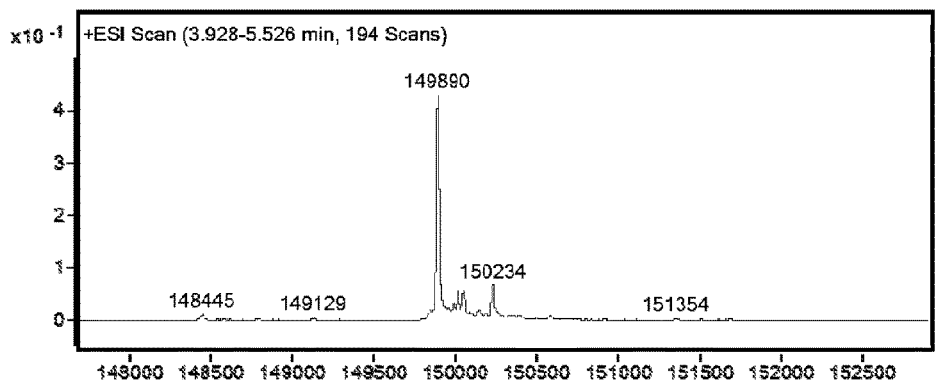
FIG. 21 shows the mass spectrum profile of the antibody-drug conjugate AXL107-BL20-MMAE.

The results are shown in FIGS. 18, 19 and 21. The mass spectrum graph of humanized antibody AXL107 (FIG. 19) and the HIC and mass spectrum graph of its antibody conjugate AXL107-BL20-MMAE (FIG. 18 and FIG. 21) all showed that the antibody AXL107 was conjugated to form the antibody conjugate AXL107-BL20-MMAE. The molecular weight of the conjugate was consistent with the expected value, and the DAR was about 4.0.

Example 15 Preparation of mAb002c-Vc-MMAE, mAb002c-BL20-MMAE and Humanized Antibody Series Hu002-BL20-MMAE PBS/EDTA (pH=7.4) buffer was added into the stock solution of chimeric antibody mAb002c targeting AXL to make the concentration at 20 mg/ml, and the antibody was reduced with 2.6 eq of TCEP at 25° C. for 2 hours. The obtained solution was cooled on ice, added with 6.0 eq of mc-VC-PAB-MMAE (purchased from Shanghai Haoyuan Chemical Co., LTD, pre-dissolved in DMA) without purification, and reacted for 1 hour at 0° C. Then cysteine was added to stop the reaction. The excess small molecules were removed using a G25 desalting column, and the obtained product was placed into 20 mM citrate-sodium citrate/6% sucrose buffer (pH 6.6), sterilized through a filter device of 0.22 micron pore and preserved at −80° C. The obtained antibody conjugate was named mAb002c-vc-MMAE.

Figure 22:
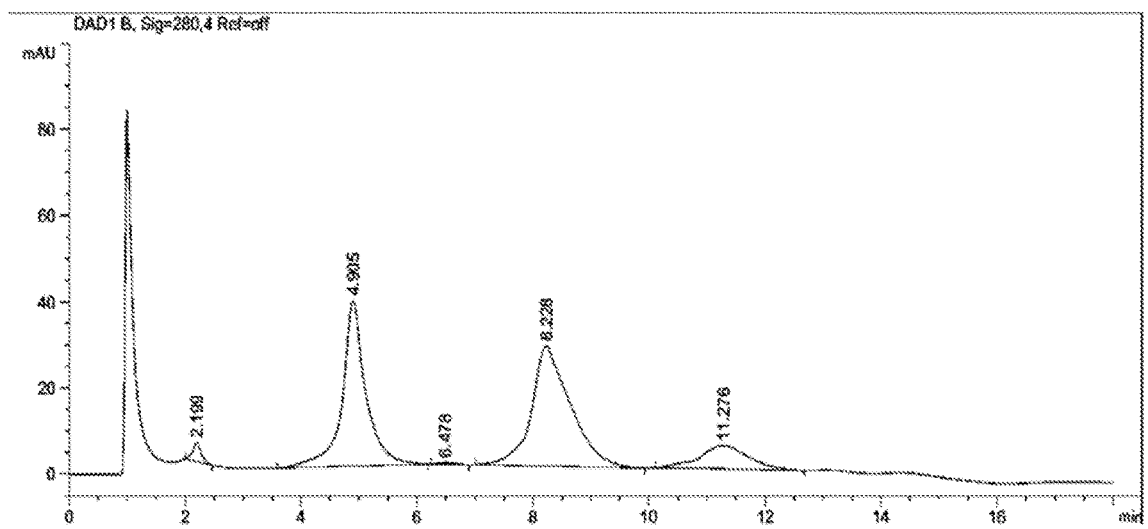
FIG. 22 shows the hydrophobic interaction chromatography (HIC) profile of the antibody-drug conjugate mAb002c-vc-MMAE.
Figure 24:
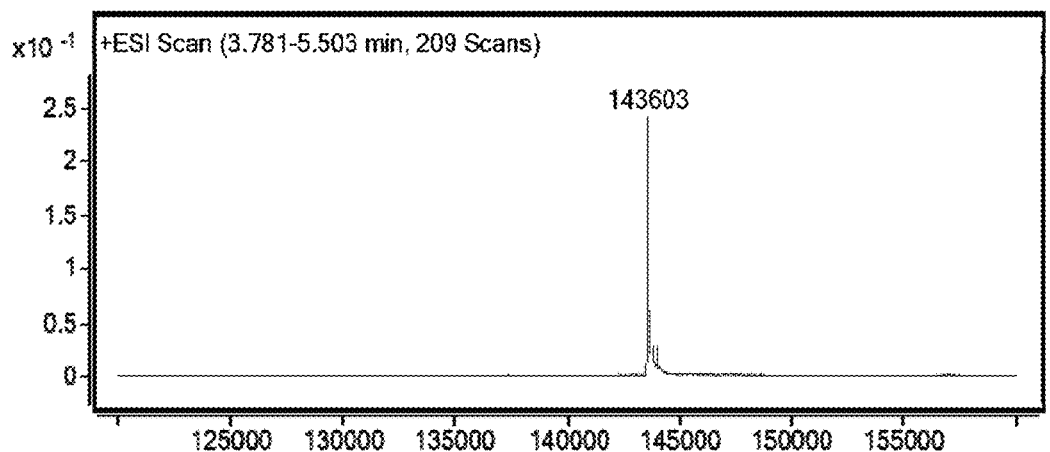
FIG. 24 shows the mass spectrum profile of the monoclonal antibody mAb002c.
Figure 25:
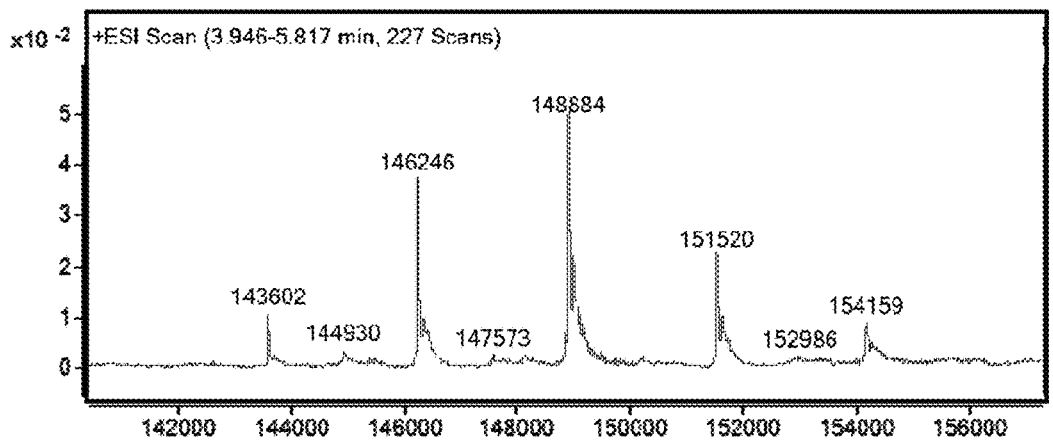
FIG. 25 shows the mass spectrum profile of the antibody-drug conjugate mAb002c-vc-MMAE.

The results are shown in FIGS. 22, 24 and 25. The mass spectrum graph of antibody mAb002c (FIG. 24) and the HIC and mass spectrum graph of its antibody conjugate mAb002c-vc-MMAE (FIG. 22 and FIG. 25) all showed that the antibody mAb002c was conjugated to form the antibody conjugate mAb002c-vc-MMAE. The molecular weight of the conjugate was consistent with the expected value, and the average DAR value was about 4.0.

The stock solution of antibody mAb002c was replaced with 50 mM sodium dihydrogen phosphate-disodium hydrogen phosphate ($NaH_2PO_4$—$Na_2HPO_4$)/150 mM sodium chloride (NaCl)/2 mM ethylenediaminetetraacetic acid (EDTA) reaction buffer (pH 7.0), to make the concentration at 10 mg/mL. Tris(2-carboxyethyl)phosphine hydrochloride (TCEP) in a 10-fold excess molar ratio was added, and the reaction solution was stirred at 25° C. for 4 hours. The excess TCEP were removed using a G25 desalting column. An appropriate amount of diethyl acetamide (DMA) was added to the collected reduction antibodies. Then Compound Ic-4 (10 mg/ml, pre-dissolved in DMA) in a 6-fold excess molar ratio was added, ensuring that the volume of DMA in the reaction system did not exceed 10%. The obtained solution was stirred at 20° C. for 2.0 hours for coupling. The coupling reaction mixture was filtrated and purified by a desalting column with pH 7.5 Tris-hydrochloric acid/sucrose gel filtration, and peak samples were collected according to the UV280 absorption value. Then the peak samples were sterilized through a filter device of 0.22 micron pore, preserved at −80° C. The obtained antibody conjugate was named mAb002c-BL20-MMAE.

Figure 23:
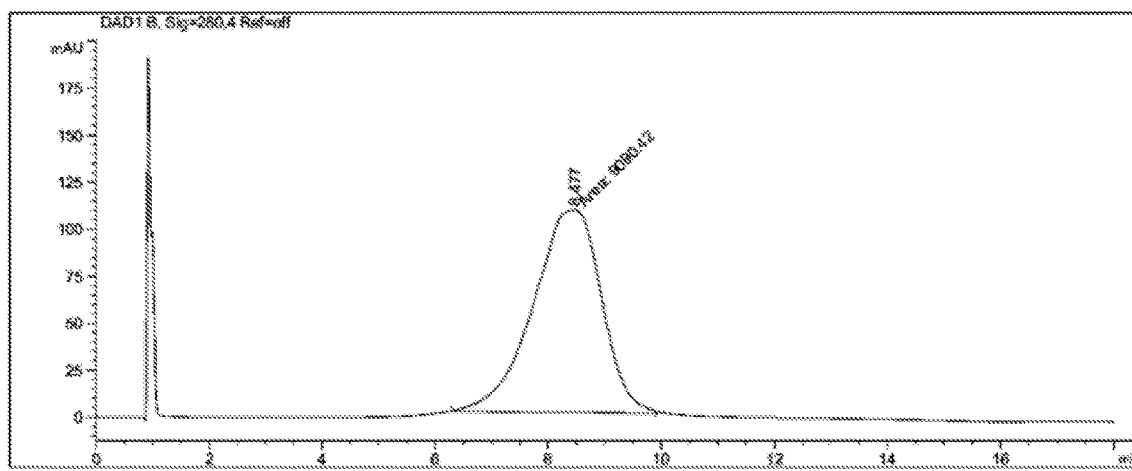
FIG. 23 shows the hydrophobic interaction chromatography (HIC) profile of the antibody-drug conjugate mAb002c-BL20-MMAE.
Figure 26:
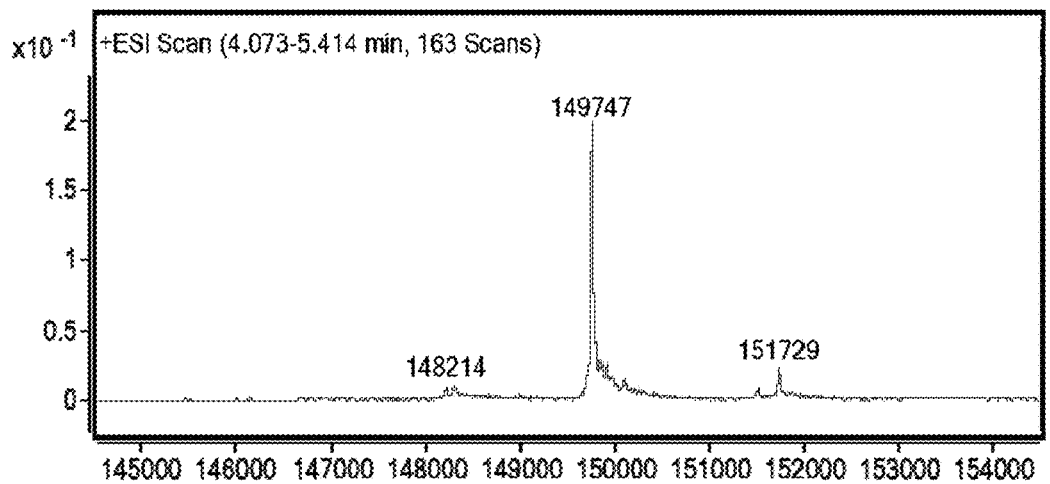
FIG. 26 shows the mass spectrum profile of the antibody-drug conjugate mAb002c-BL20-MMAE.

The results are shown in FIGS. 23, 24 and 26. The mass spectrum graph of antibody mAb002c (FIG. 24) and the HIC and mass spectrum graph of its antibody conjugate mAb002c-BL20-MMAE (FIG. 23 and FIG. 26) all showed that the antibody mAb002c was conjugated to form the antibody conjugate mAb002c-BL20-MMAE. The molecular weight of the conjugate was consistent with the expected value, and the DAR was about 4.0.

Figure 27:
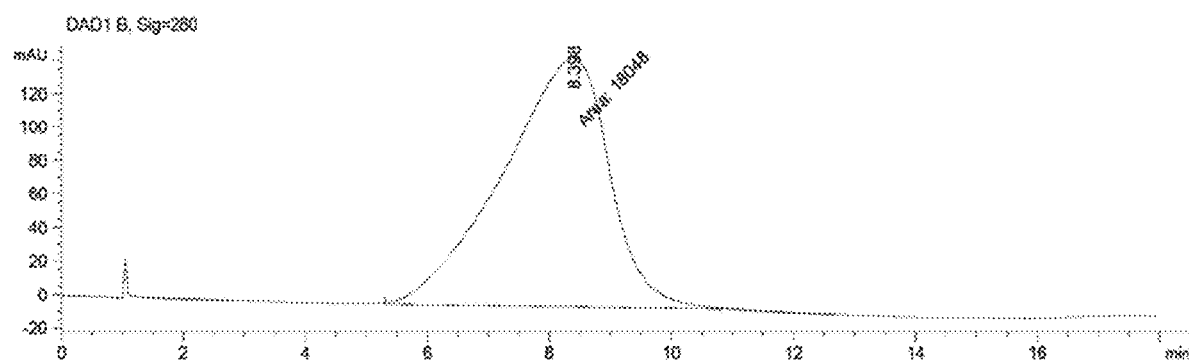
FIG. 27 shows the hydrophobic interaction chromatography (HIC) profile of the antibody-drug conjugate Hu002-2-BL20-MMAE.
Figure 28:
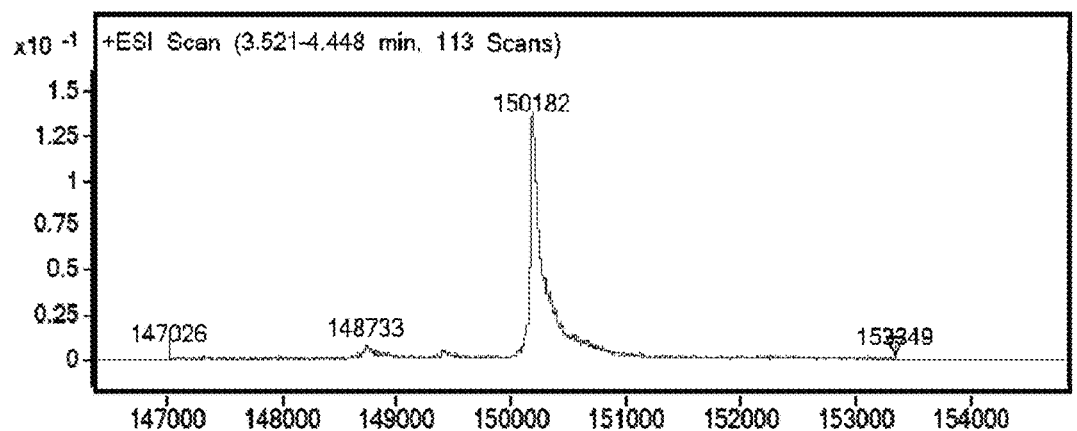
FIG. 28 shows the mass spectrum profile of the antibody-drug conjugate Hu002-2-BL20-MMAE.
Figure 29:
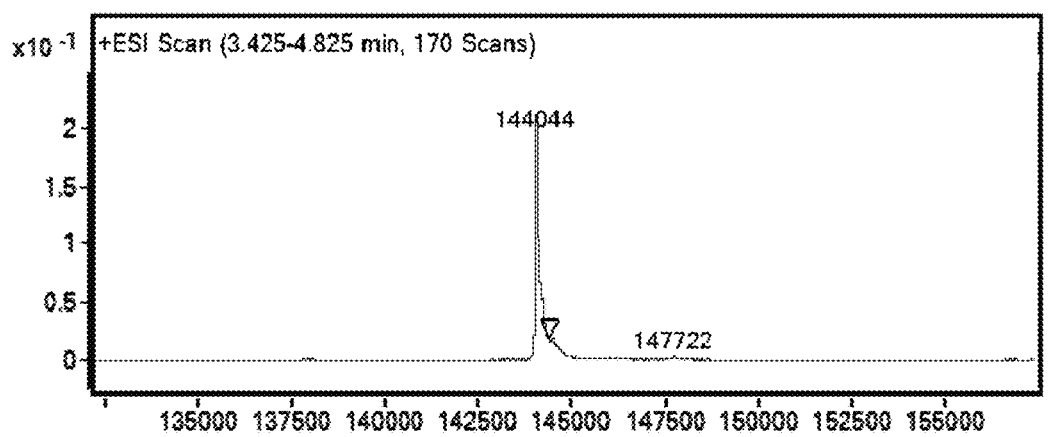
FIG. 29 shows the mass spectrum profile of the humanized monoclonal antibody Hu002-2.

The preparation method of Hu002-BL20-MMAE using a series of humanized antibodies was the same as the preparation method of the aforementioned mAb002c-BL20-MMAE. Taking the humanized antibody Hu002-2-BL20-MMAE as an example, the results are shown in FIGS. 27, 28 and 29. The mass spectrum graph of antibody Hu002-2 (FIG. 52) and the HIC and mass spectrum graph of its antibody conjugate Hu002-2-BL20-MMAE (FIG. 27 and FIG. 28) all showed that the antibody Hu002-2 was conjugated to form the antibody conjugate Hu002-2-BL20-MMAE. The molecular weight of the conjugate was consistent with the expected value, and the DAR was about 4.0.

µL/well, the cells were cultured at 37° C., 5% $CO_2$ for about 4-12 hours, and then AXL-ADCs of different concentrations (setting 3 multiple wells for each drug concentration) and the corresponding solvent control and blank control were added, respectively. After 4-6 days of reaction, the culture medium was poured, and MTS reaction solution (purchased from Promega, cat #G3581) was added at 100 µL/well, and reacted at 37° C. to the expected color depth, and then placed into a multifunctional microplate reader (BioTek Synergy II) to detect the cell viability of each group (OD490 nm), and the cell survival rate was calculated according to the following formula: survival rate=(OD administration−OD blank)/(OD control−OD blank)×100%. Each proliferation assay was set to be repeated 3-4 times independently. The above datas were analyzed with GraphPad Prism 5 software, and the $IC_{50}$ value of the drugs on different cell lines was calculated, respectively.

Figure 30:
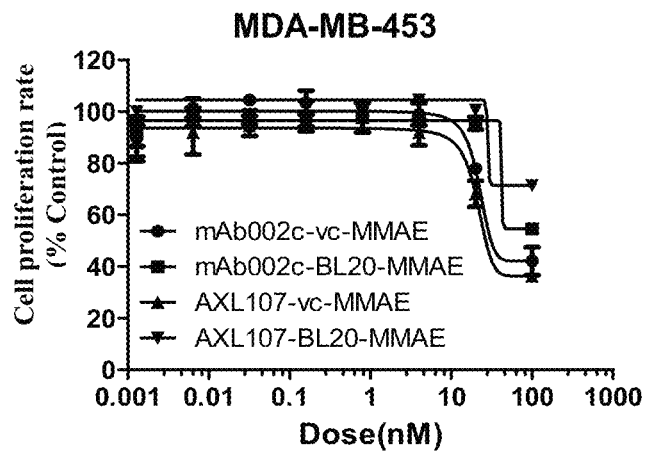
FIG. 30 shows the test results of inhibitory activity ($IC_{50}$) of mAb002c-ADC and AXL107-ADC on the proliferation of MDA-MB-453 cells in vitro.
Figure 31:
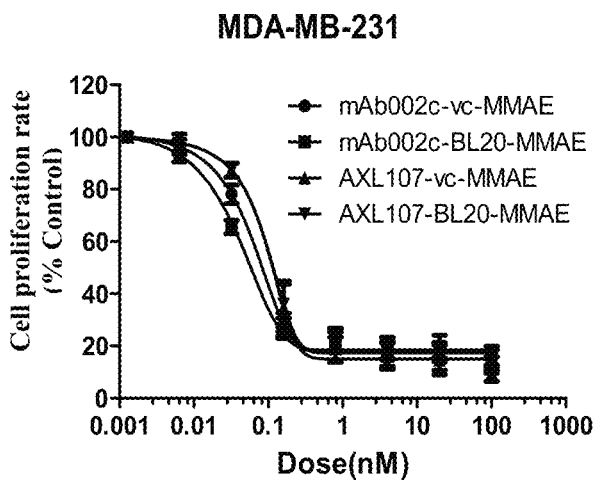
FIG. 31 shows the test results of inhibitory activity ($IC_{50}$) of mAb002c-ADC and AXL107-ADC on the proliferation of MDA-MB-231 cells in vitro.
Figure 32:
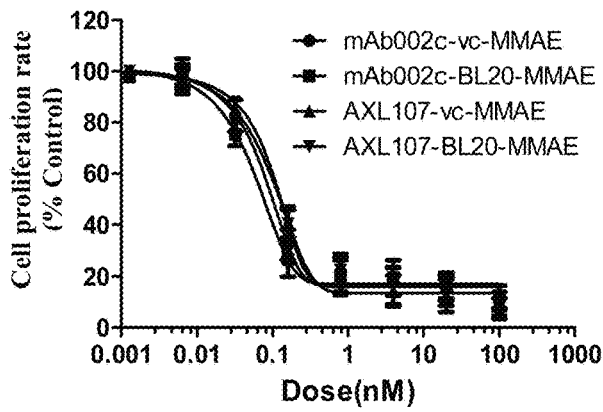
FIG. 32 shows the test results of inhibitory activity ($IC_{50}$) of mAb002c-ADC and AXL107-ADC on the proliferation of Hs578T cells in vitro.
Figure 33:
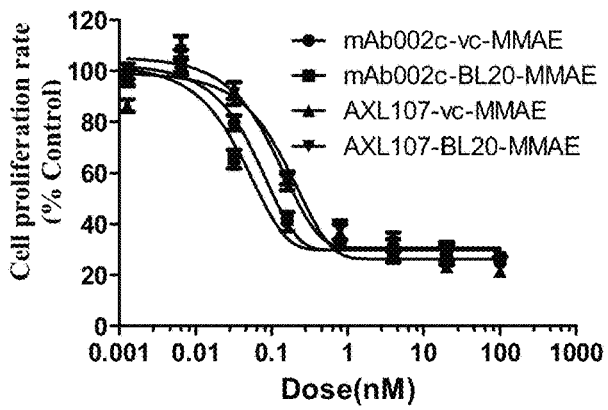
FIG. 33 shows the test results of inhibitory activity ($IC_{50}$) of mAb002c-ADC and AXL107-ADC on the proliferation of Calu-1 cells in vitro.
Figure 34:
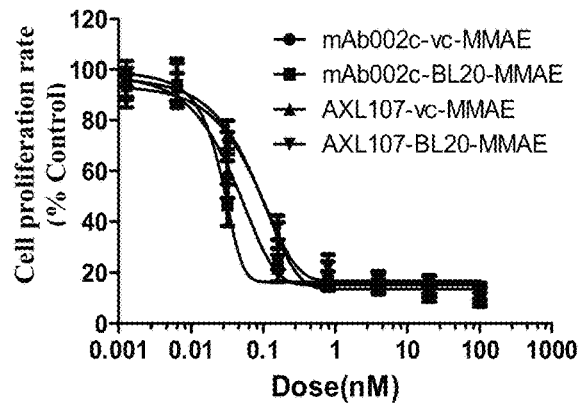
FIG. 34 shows the test results of inhibitory activity ($IC_{50}$) of mAb002c-ADC and AXL107-ADC on the proliferation of LCLC-103H cells in vitro.
Figure 35:
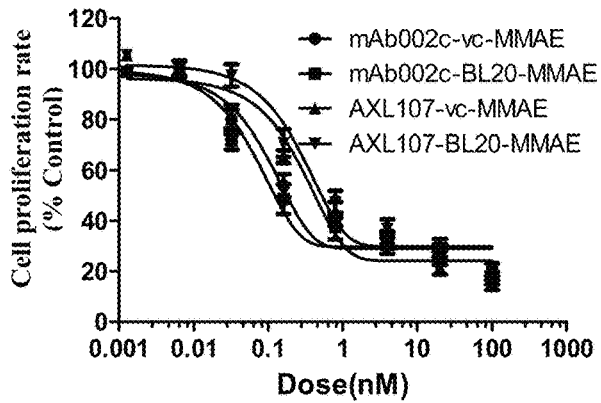
FIG. 35 shows the test results of inhibitory activity ($IC_{50}$) of mAb002c-ADC and AXL107-ADC on the proliferation of U87MG cells in vitro.

The experimental results show that the AXL antibody-drug conjugates mAb002c-vc-MMAE and mAb002c-BL20-MMAE of the present invention had high AXL-targeting specific cytotoxic activities, that is, had no obvious proliferation inhibitory effect on AXL-low-expression MDA-MB-453 cells (FIG. 30), but had very strong proliferation inhibitory effects on AXL-high-expression cells of triple negative breast cancer MDA-MB-231 (FIG. 31), Hs578T (FIG. 32), lung cancer Calu-1 (FIG. 33), LCLC-103H (FIG. 34) and glioma U87MG (FIG. 35), and the $IC_{50}$ values were 0.03 nM to 0.07 nM (Table-9). In addition, the antibody-drug conjugates mAb002c-vc-MMAE and mAb002c-BL20-MMAE of the present invention had significantly stronger inhibitory activities on AXL-highly expressed tumor cells than the control antibody-drug conjugates AXL107-vc-MMAE and AXL107-BL20-MMAE.

TABLE 9

In vitro anti-tumor activity of chimeric antibody-drug conjugates

| Name of antibody-drug conjugate | Cell proliferation inhibition rate $IC_{50}$ ± SD (nM) | | | | | |
|---|---|---|---|---|---|---|
| | MDA-MB-453 (n = 3) | MDA-MB-231 (n = 4) | Hs578T (n = 4) | Calu-1 (n = 4) | LCLC-103H (n = 4) | U87MG (n = 4) |
| mAb002c-vc-MMAE | >10 | 0.0596 ± 0.0112 | 0.0718 ± 0.0159 | 0.0574 ± 0.0094 | 0.04597 ± 0.0098 | 0.01186 ± 0.0432 |
| mAb002c-BL20-MMAE | >10 | 0.0391 ± 0.0051 | 0.0531 ± 0.0101 | 0.0378 ± 0.0082 | 0.02742 ± 0.0026 | 0.0621 ± 0.0196 |
| AXL107-vc-MMAE | >10 | 0.0912 ± 0.0274 | 0.1007 ± 0.0045 | 0.1694 ± 0.0349 | 0.0810 ± 0.0157 | 0.1948 ± 0.0680 |

Example 16 In Vitro Anti-Tumor Activities of AXL Chimeric Antibody-Drug Conjugates (AXL-ADCs) Against Triple Negative Breast Cancer Cells, Lung Cancer Cells and Glioma Cells with AXL High Expression The cell lines used in this example were purchased from the American Type Culture Collection (ATCC) or the Cell Bank of the Chinese Academy of Sciences, and were cultured according to the corresponding instructions, including: MDA-MB-453, MDA-MB-231, Hs578T, Calu-1, NCI-H1299, LCLC-103H, NCI-H292, NCI-H441, NCI-H2228, NCI-H460, and U87MG.

Cell proliferation test: the above-mentioned cells in a logarithmic growth phase were inoculated respectively into a 96-well cell culture plate at a density of 600-2,500 cells per well (depending on the growth rate of different cells), 150

Example 17 In Vitro Anti-Tumor Activities of Humanized AXL-ADCs

Figure 36:
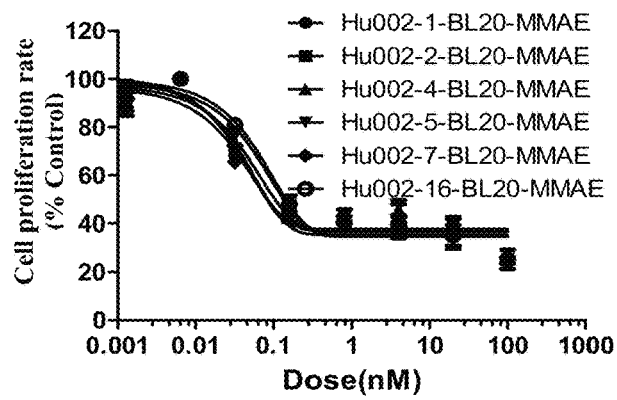
FIG. 36 shows the test results of inhibitory activity ($IC_{50}$) on the proliferation of MDA-MB-231 cells in vitro by ADCs of humanized antibodies Hu002 series coupled to BL20-MMAE.
Figure 37:
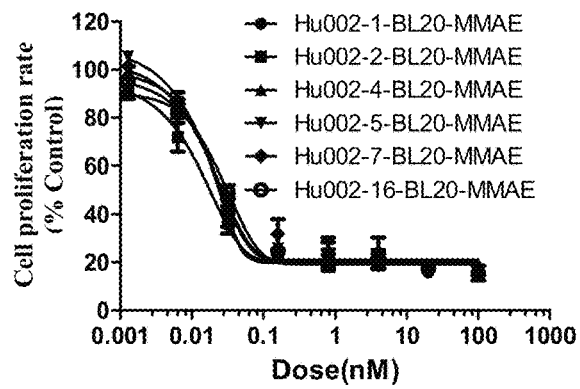
FIG. 37 shows the test results of inhibitory activity ($IC_{50}$) on the proliferation of Hs578T cells in vitro by ADCs of humanized antibodies Hu002 series coupled to BL20-MMAE.
Figure 38:
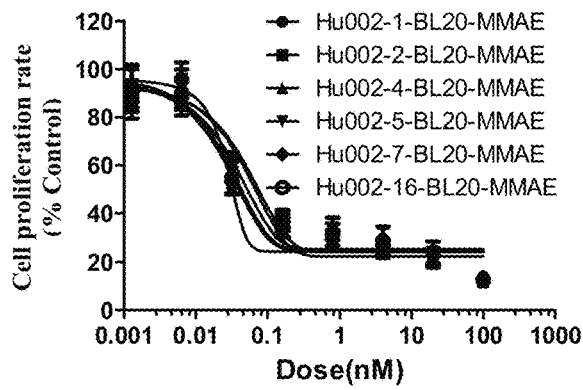
FIG. 38 shows the test results of inhibitory activity ($IC_{50}$) on the proliferation of U87MG cells in vitro by ADCs of humanized antibodies Hu002 series coupled to BL20-MMAE.
Figure 39:
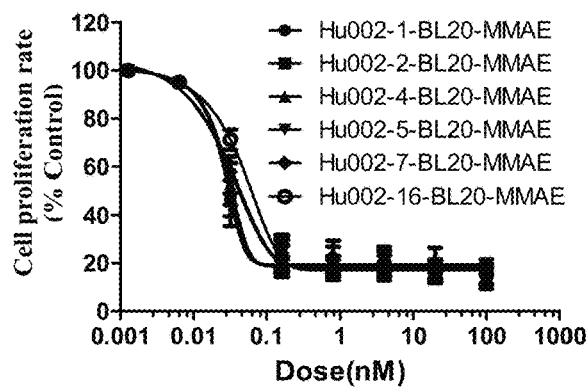
FIG. 39 shows the test results of inhibitory activity ($IC_{50}$) on the proliferation of LCLC-103H cells in vitro by ADCs of humanized antibodies Hu002 series coupled to BL20-MMAE.

Similarly, by referring to the detection method in Example 16, the AXL humanized series antibody-drug conjugates Hu002-1/2/4/5/7/16-BL20-MMAE of the present invention had high AXL-targeting specific cytotoxic activities, that is, had no obvious proliferation inhibitory effect on AXL-low-expression MDA-MB-453 cells, but had very strong proliferation inhibitory effects on AXL-high-expression cells of triple negative breast cancer MDA-MB-231 (FIG. 36), Hs578T (FIG. 37), glioma U87MG (FIG. 38) and lung cancer LCLC-103H (FIG. 39) cells, and the $IC_{50}$ value were 0.013 nM-0.05 nM (Table-1).

TABLE 10

In vitro anti-tumor activities of humanized AXL-ADCs

| Name of antibody-drug conjugate | Cell proliferation inhibition rate $IC_{50}$ ± SD (nM) | | | |
|---|---|---|---|---|
| | U87MG | MDA-MB-231 | Hs578T | LCLC-103H |
| Hu002-1-BL20-MMAE | 0.0450 ± 0.0124 | 0.0368 ± 0.0046 | 0.0172 ± 0.0018 | 0.0302 ± 0.0011 |
| Hu002-2-BL20-MMAE | 0.0453 ± 0.0067 | 0.0424 ± 0.0038 | 0.0130 ± 0.0115 | 0.0281 ± 0.0019 |
| Hu002-4-BL20-MMAE | 0.0445 ± 0.0074 | 0.0361 ± 0.0002 | 0.0165 ± 0.0012 | 0.03103 ± 0.0008 |
| Hu002-5-BL20-MMAE | 0.0440 ± 0.0169 | 0.0598 ± 0.0110 | 0.0151 ± 0.0013 | 0.0334 ± 0.0028 |
| Hu002-7-BL20-MMAE | 0.0332 ± 0.0050 | 0.0368 ± 0.0027 | 0.0139 ± 0.0018 | 0.0304 ± 0.0016 |
| Hu002-16-BL20-MMAE | 0.0413 ± 0.0013 | 0.0660 ± 0.0046 | 0.0229 ± 0.0075 | 0.0408 ± 0.0052 |

Example 18 In Vivo Anti-Tumor Activities of AXL-ADCs

200 μL of cell suspension containing 5×10⁶ U87MG or LCLC-103H was subcutaneously inoculated into the back of female immunodeficiency mice (Balb/c nude, 6-8 weeks old), respectively. When the tumor volume reached 100-300 mm³ and obvious tumor growth could be observed, the mice were randomly grouped according to tumor size and nude mouse body weight (n=6-8), and administrated once a week through the tail vein for a total of 2 weeks in a dose of 25 mg/kg, 3 mg/kg, 1 mg/kg, 0.5 mg/kg, respectively. At the same time, hIgG1-BL20-MMAE was set as a negative control. The tumor volume and nude mice body weight were measured 2-3 times a week and recorded to draw a tumor growth curve. After the experiment, the experimental data were collected and analyzed, the tumor growth curve and nude mouse weight change curve were drawn. The subcutaneous transplanted tumor was surgically removed and weighted, and the calculation formula for tumor volume (V) was: $V=L \times W^2/2$, wherein L and W represented the length and width of the tumor, respectively.

The chimeric antibody mAb002c, 4 kinds of preferred humanized antibodies Hu002-1, Hu002-2, Hu002-4, and Hu002-5 were coupled to vc-MMAE or BL20-MMAE, respectively, while the existing technology AXL107-vc-MMAE was used as a comparation to evaluate the anti-tumor activity in vivo. The preparation of humanized AXL-ADC was carried out with reference to Example 15.

Figure 40:
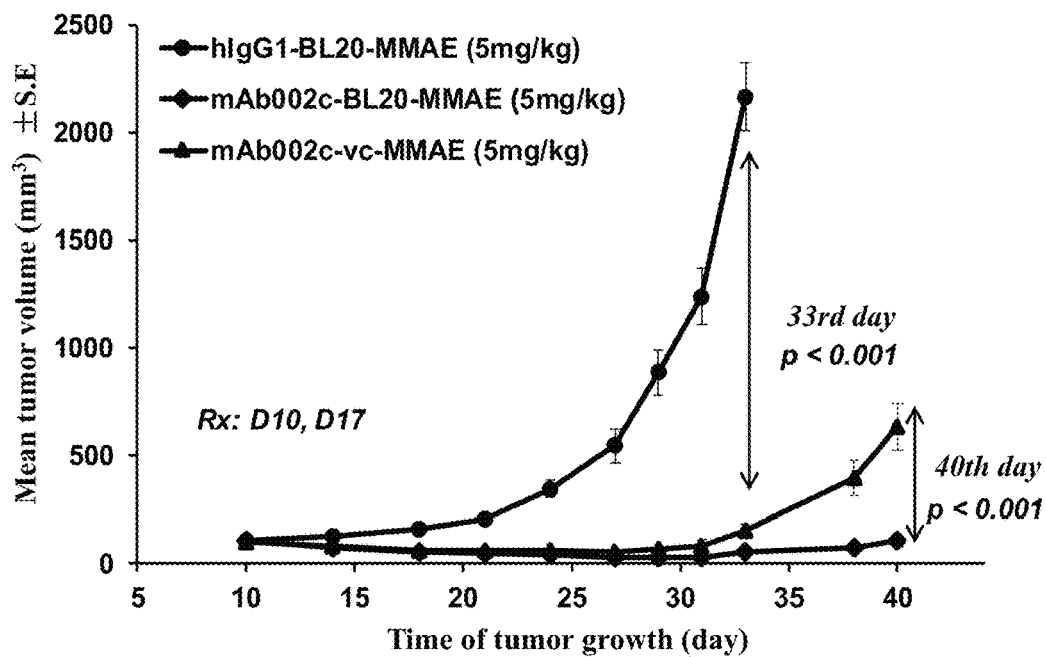
FIG. 40 shows the anti-tumor efficacy on U87MG glioma model in vivo by ADCs (both 5 mg/kg) of chimeric antibody mAb002c coupled to vc-MMAE or BL20-MMAE, respectively. The results show that compared with vc-MMAE, BL20-MMAE has better therapeutic effect in vivo.

As shown in FIG. 40, in the U87MG tumor model, the anti-tumor effect of mAb002c-BL20-MMAE or mAb002c-vc-MMAE in a dose of 5 mg/kg was very significant and similar during the administration period, but mAb002c-vc-MMAE group shown tumor regrowth 3 weeks after drug withdrawal, and its anti-tumor effect was significantly lower than that of the mAb002c-BL20-MMAE group, which indicated that the BL20-MMAE linker was more superior in vivo.

Figure 41:
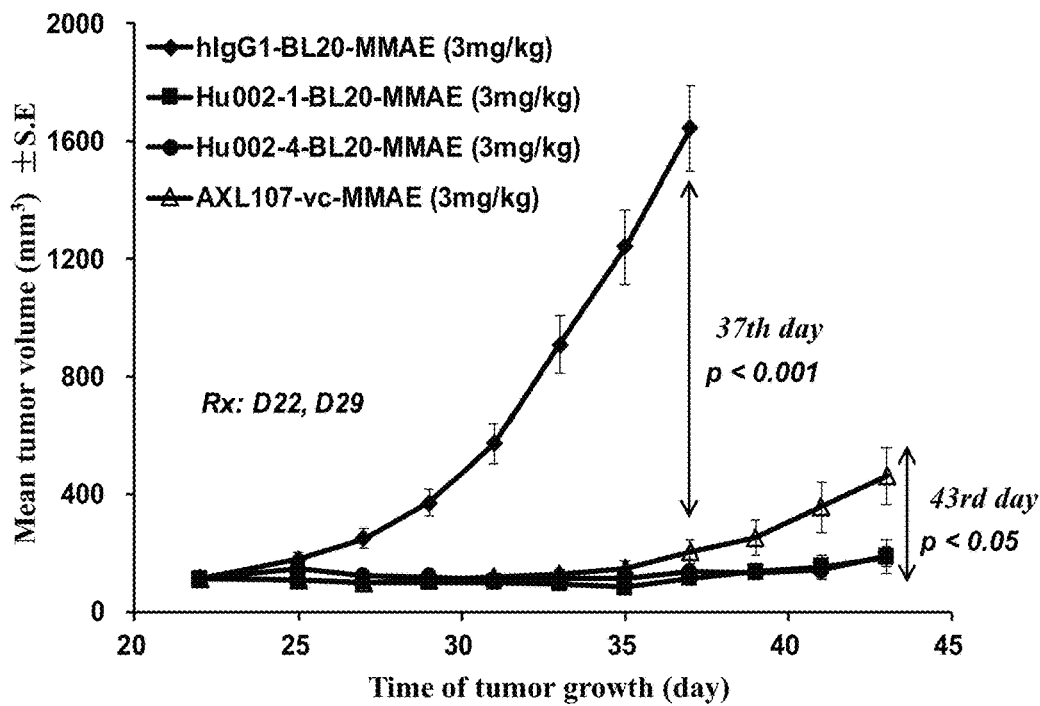
FIG. 41 shows the anti-tumor efficacy on U87MG glioma model in vivo by humanized Hu002-1 and Hu002-4 antibodies coupled to BL20-MMAE (3 mg/kg) or AXL107-vc-MMAE (3 mg/kg).
Figure 42:
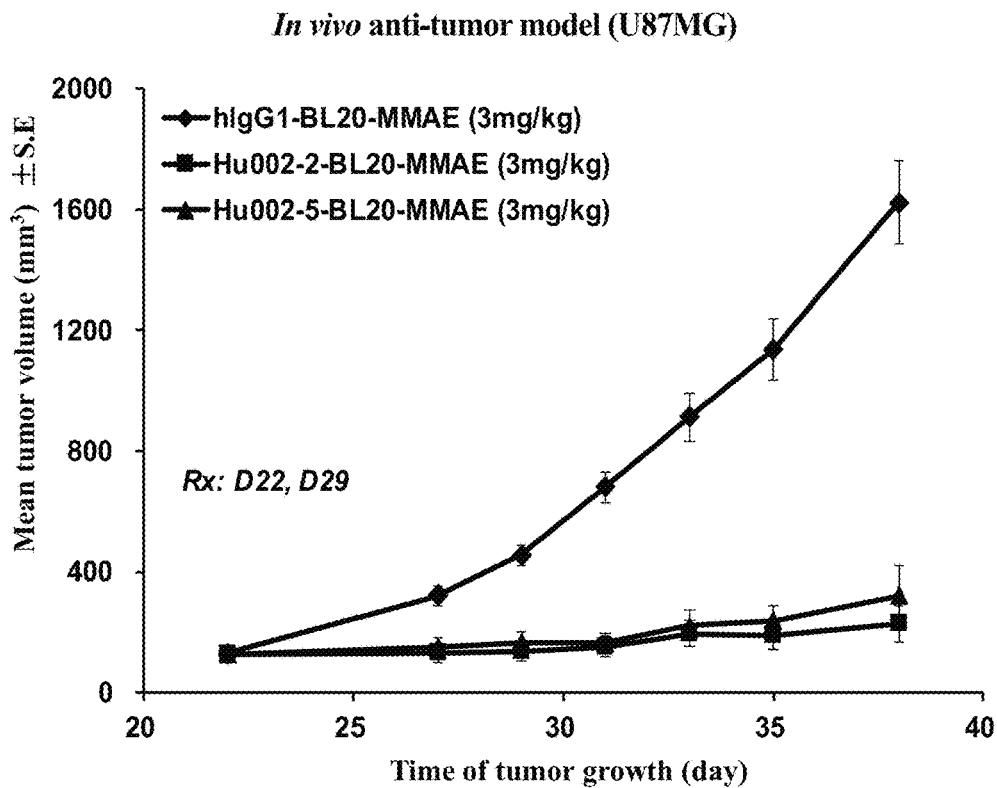
FIG. 42 shows the results of anti-tumor efficacy on U87MG glioma model in vivo by ADCs (3 mg/kg; once a week for 2 times) of humanized Hu002-2 and Hu002-5 antibodies coupled to BL20-MMAE, respectively.

As shown in FIG. 41 and FIG. 42, in the U87MG tumor model, when the 4 preferred humanized AXL-ADC and AXL107-vc-MMAE were used for in vivo drug efficacy test in a dose of 3 mg/kg, it was observed that all ADCs had excellent anti-tumor activity, and the preferred AXL-ADC of the present invention had more significant tumor treatment effects in vivo than AXL107-vc-MMAE.

The results of the three in vivo efficacy trials of U87MG described above were summarized and counted (Table-11).

TABLE 11

Anti-tumor activity of AXL-ADC in vivo (U87MG model)

| U87MG in vivo-1 (FIG. 40) | | | |
|---|---|---|---|
| | Tumor volume on day 33 ± SE (mm³) | Tumor inhibition rate on day 33 (%); P value | Tumor volume on day 40 ± SE (mm³); % control; P value |
| hIgG1-BL20-MMAE (5 mg/kg) | 2164.3 ± 156.7 | Control | / |
| mAb002c-vc-MMAE (5 mg/kg) | 156.4 ± 28.4 | 93; p < 0.001 | 631.5 ± 109.5 (Control) |
| mAb002c-BL20-MMAE (5 mg/kg) | 53.1 ± 7.6 | 98; p < 0.001 | 108.7 ± 28.1 (17.2); p < 0.001 |

| U87MG in vivo-2 (FIG. 41) | | | |
|---|---|---|---|
| | Tumor volume on day 37 ± SE (mm³) | Tumor inhibition rate on day 37 (%); P value | Tumor volume on day 43 ± SE (mm³); % control; P value |
| hIgG1-BL20-MMAE (3 mg/kg) | 1642.9 ± 145.7 | Control | / |
| AXL107-vc-MMAE (3 mg/kg) | 203.3 ± 39.4 | 88; p < 0.001 | 461.3 ± 96.9 (Control) |
| Hu002-1-BL20-MMAE (3 mg/kg) | 113.9 ± 19.9 | 93; p < 0.001 | 186.5 ± 56.9 (40.4); p < 0.05 |
| Hu002-4-BL20-MMAE (3 mg/kg) | 135.1 ± 18.2 | 92; p < 0.001 | 187.7 ± 35.3 (40.7); p < 0.05 |

| U87MG in vivo-3 (FIG. 42) | | | |
|---|---|---|---|
| | Tumor volume on day 38 ± SE (mm³) | Tumor inhibition rate on day 38 (%); P value | |
| hIgG1-BL20-MMAE (3 mg/kg) | 1621.7 ± 137.7 | Control | / |
| Hu002-2-BL20-MMAE (3 mg/kg) | 229.6 ± 59.8 | 86; p < 0.001 | / |
| Hu002-5-BL20-MMAE (3 mg/kg) | 321.4 ± 96.3 | 80; p < 0.001 | / |

Figure 43:
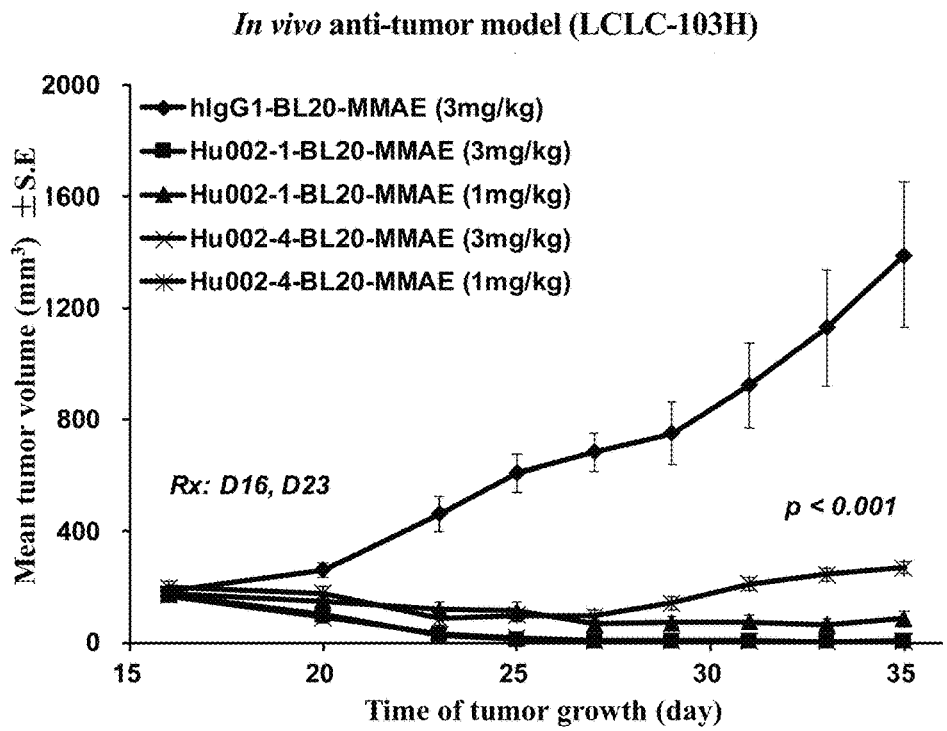
FIG. 43 shows the results of anti-tumor efficacy on LCLC-103H lung cancer model in vivo by ADCs (3 mg/kg or 1 mg/kg; once a week for 2 times) of humanized Hu002-1 and Hu002-4 antibodies coupled to BL20-MMAE, respectively.
Figure 44:
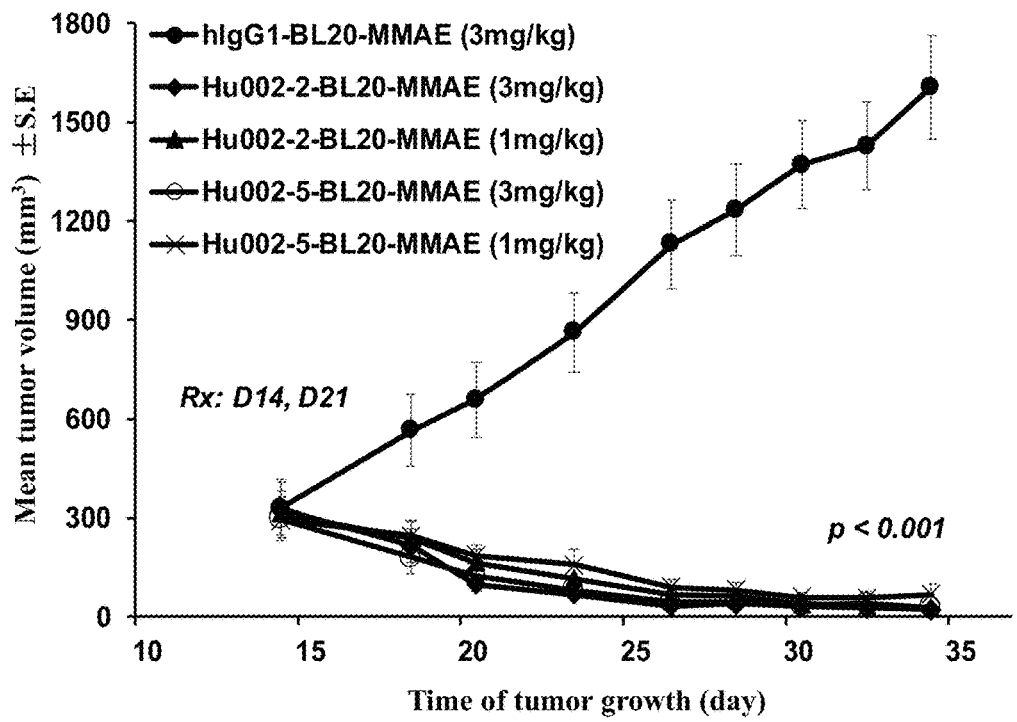
FIG. 44 shows the results of anti-tumor efficacy on LCLC-103H lung cancer model in vivo by ADCs (3 mg/kg or 1 mg/kg; once a week for 2 times) of humanized Hu002-2 and Hu002-5 antibodies coupled to BL20-MMAE, respectively.

As shown in FIG. 43 and FIG. 44, in the LCLC-103H tumor model, the four preferred AXL-ADCs of the present invention showed dose-related treatments in the doses of 3 mg/kg and 1 mg/kg, and could lead to extremely significant tumor regression, which showed that LCLC-103H tumor was highly sensitive to the treatment of AXL-ADCs.

Figure 45:
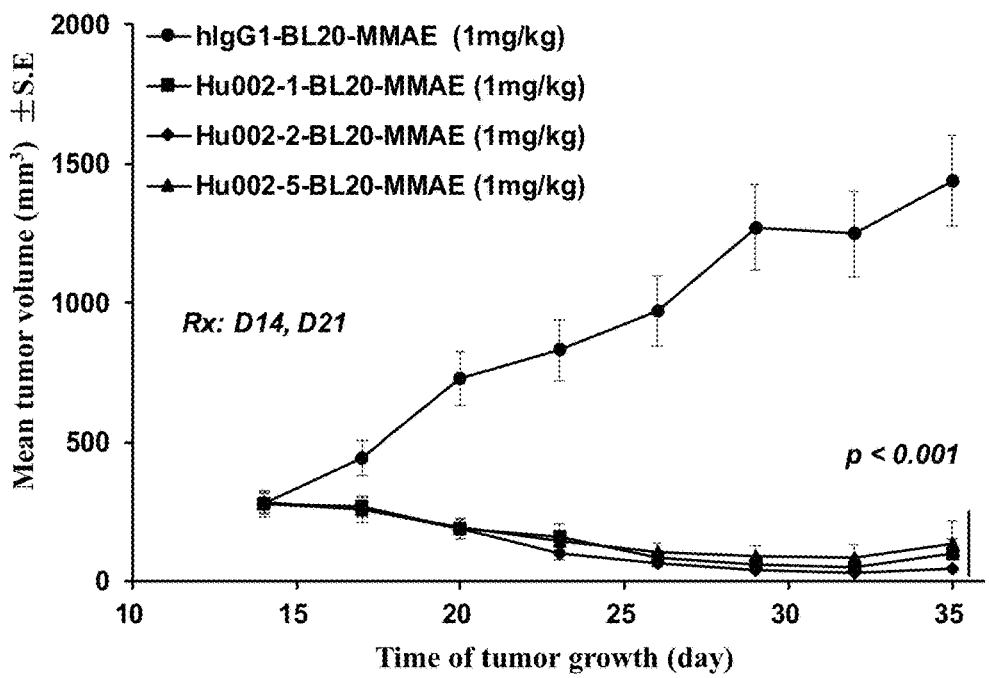
FIG. 45 shows the results of anti-tumor efficacy on LCLC-103H lung cancer model in vivo by ADCs (all 1 mg/kg; once a week for 2 times) of humanized Hu002-1, Hu002-2 and Hu002-5 antibodies coupled to BL20-MMAE, respectively.

As shown in FIG. 45, in the repeated trial of LCLC-103H tumor, the administration of Hu002-1-BL2-MMAE, Hu02-2-BL2-MMAE and Hu02-5-BL2-MMAE in a dose of 1 mg/kg could lead to significant tumor regression, wherein Hu002-2-BL20-MMAE had the most significant tumor regression effect.

The results of the three in vivo efficacy trials of LCLC-03H described above were summarized and counted (Table-12).

TABLE 12

Anti-tumor activity of AXL-ADC in vivo (LCLC-103H model)

LCLC-103H in vivo-1 (FIG. 43)

| | Tumor volume on day 35 ± SE ($mm^3$) | Tumor inhibitory rate (%) | P value (compared with hIgG1-BL20-MMAE) |
|---|---|---|---|
| hIgG1-BL20-MMAE (3 mg/kg) | 1390.3 ± 259.1 | Control | Control |
| Hu002-1-BL20-MMAE (3 mg/kg) | 4.8 ± 0.3 | 100 | <0.001 |
| Hu002-1-BL20-MMAE (1 mg/kg) | 87.1 ± 28.2 | 94 | <0.001 |
| Hu002-4-BL20-MMAE (3 mg/kg) | 5.9 ± 0.5 | 100 | <0.001 |
| Hu002-4-BL20-MMAE (1 mg/kg) | 269.7 ± 173.3 | 81 | <0.001 |

LCLC-103H in vivo-2 (FIG. 44)

| | Tumor volume on day 34 ± SE ($mm^3$) | Tumor inhibitory rate (%) | P value (compared with hIgG1-BL20-MMAE) |
|---|---|---|---|
| hIgG1-BL20-MMAE (3 mg/kg) | 1607.1 ± 157.2 | Control | Control |
| Hu002-2-BL20-MMAE (3 mg/kg) | 22.0 ± 5.2 | 99 | <0.001 |
| Hu002-2-BL20-MMAE (1 mg/kg) | 26.5 ± 6.6 | 98 | <0.001 |
| Hu002-5-BL20-MMAE (3 mg/kg) | 28.6 ± 7.4 | 98 | <0.001 |
| Hu002-5-BL20-MMAE (1 mg/kg) | 67.7 ± 31.2 | 96 | <0.001 |

LCLC-103H in vivo-3 (FIG. 45)

| | Tumor volume on day 35 ± SE ($mm^3$) | Tumor inhibitory rate (%) | P value (compared with hIgG1-BL20-MMAE) |
|---|---|---|---|
| hIgG1-BL20-MMAE (1 mg/kg) | 1439.0 ± 160.6 | Control | Control |
| Hu002-1-BL20-MMAE (1 mg/kg) | 100.4 ± 53.8 | 93 | <0.001 |
| Hu002-2-BL20-MMAE (1 mg/kg) | 42.8 ± 9.9 | 97 | <0.001 |
| Hu002-5-BL20-MMAE (1 mg/kg) | 133.3 ± 81.6 | 91 | <0.001 |

Figure 46:
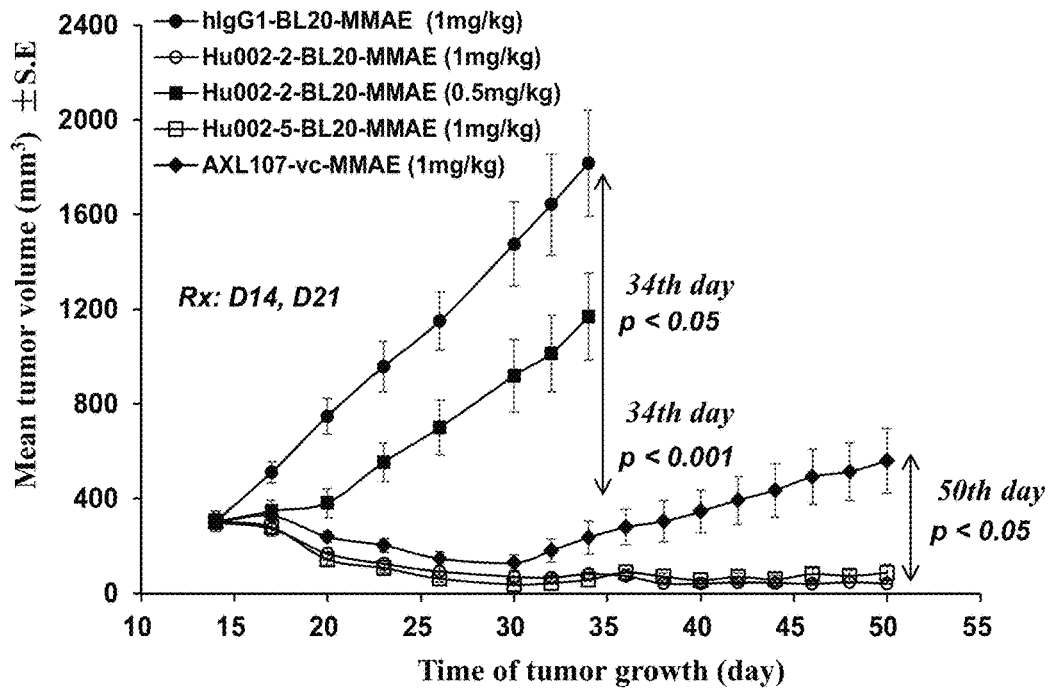
FIG. 46 shows the results of anti-tumor efficacy on LCLC-103H lung cancer model in vivo by ADCs of humanized Hu002-2 and Hu002-5 antibodies respectively coupled to BL20-MMAE (1 mg/kg or 0.5 mg/kg), and AXL107-vc-MMAE (1 mg/kg), wherein the ADCs were administrated once a week for 2 times.

As shown in FIG. 46 and Table-13, in another repeated trial of LCLC-103H, the administration of Hu002-2-BL2-MMAE and Hu02-5-BL2-MMAE in a dose of 1 mg/kg was confirmed again to induce tumor regression, and their effects were significantly better than the administration of AXL107-vc-MAE in a same dose. At the same time, 0.5 mg/kg of Hu002-2-BL20-MMAE also had certain anti-tumor effect.

TABLE 13

Anti-tumor activity of AXL-ADC in vivo (LCLC-103H model)

LCLC-103H in vivo-4 (FIG. 46)

| | Tumor volume on day 34 ± SE ($mm^3$) | Tumor inhibition rate on day 34 (%); P value | Tumor volume on day 50 ± SE ($mm^3$); % control; P value |
|---|---|---|---|
| hIgG1-BL20-MMAE (1 mg/kg) | 1816.7 ± 225.3 | Control | / |
| Hu002-2-BL20-MMAE (0.5 mg/kg) | 1169.9 ± 184.4 | 36; p < 0.05 | / |
| Hu002-2-BL20-MMAE (1 mg/kg) | 82.0 ± 20.8 | 95; p < 0.001 | 41.5 ± 2.3 (7.4); p < 0.05 |
| Hu002-5-BL20-MMAE (1 mg/kg) | 58.2 ± 4.6 | 97; p < 0.001 | 87.2 ± 35.7 (15.6); p < 0.05 |
| AXL107-vc-MMAE (1 mg/kg) | 236.6 ± 69.7 | 87; p < 0.001 | 559.2 ± 136.8 (Control) |

Example 19 Regression Activity of Humanized AXL-ADC on Large Tumors

Based on the high sensitivity of LCLC-103H lung cancer to AXL-ADC, this example studied the activity of AXL-ADC on extra-large tumors. When the tumor growth volume reached 1000-2000 $mm^3$, the drug was administered, and the inhibition of tumor growth or tumor regression was observed. The test method may be referred to Example 18.

Figure 47:
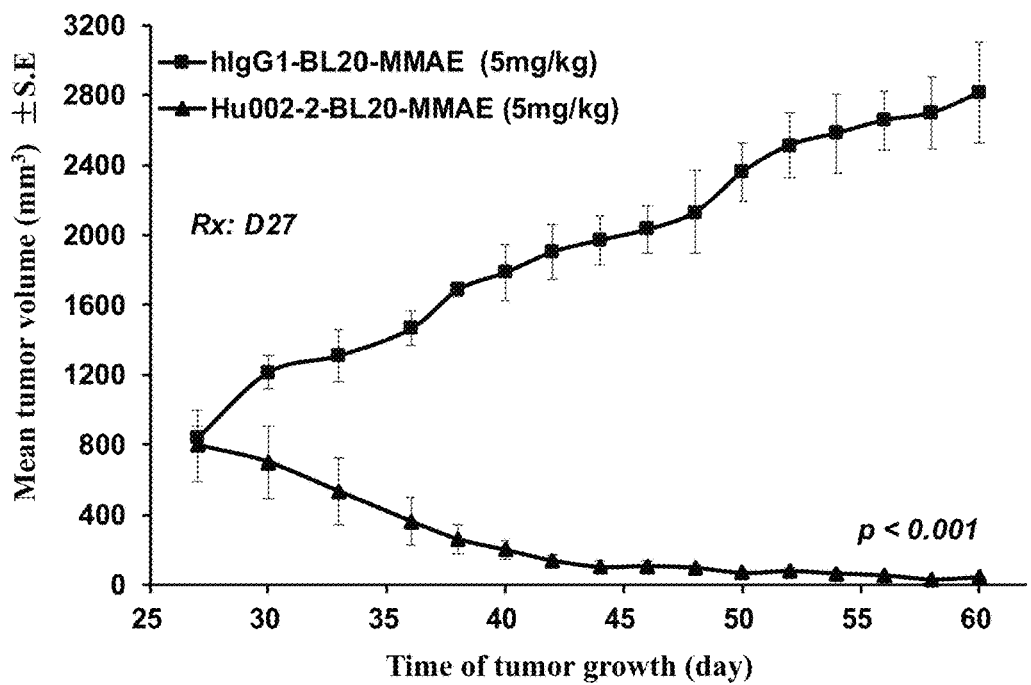
FIG. 47 shows that the humanized Hu002-2-BL20-MMAE (5 mg/kg; single dose) targeting LCLC-103H large tumors (800 mm³ is the volume at the initial dose) can lead to a result of tumor regression.

The results are shown in FIG. 47. When LCLC-103H tumor grew to a volume of 800 $mm^3$ in vivo, a single dose of 5 mg/kg Hu002-2-BL20-MMAE was administered, and complete regression of the tumor was observed on the 34th day of treatment.

Figure 48:
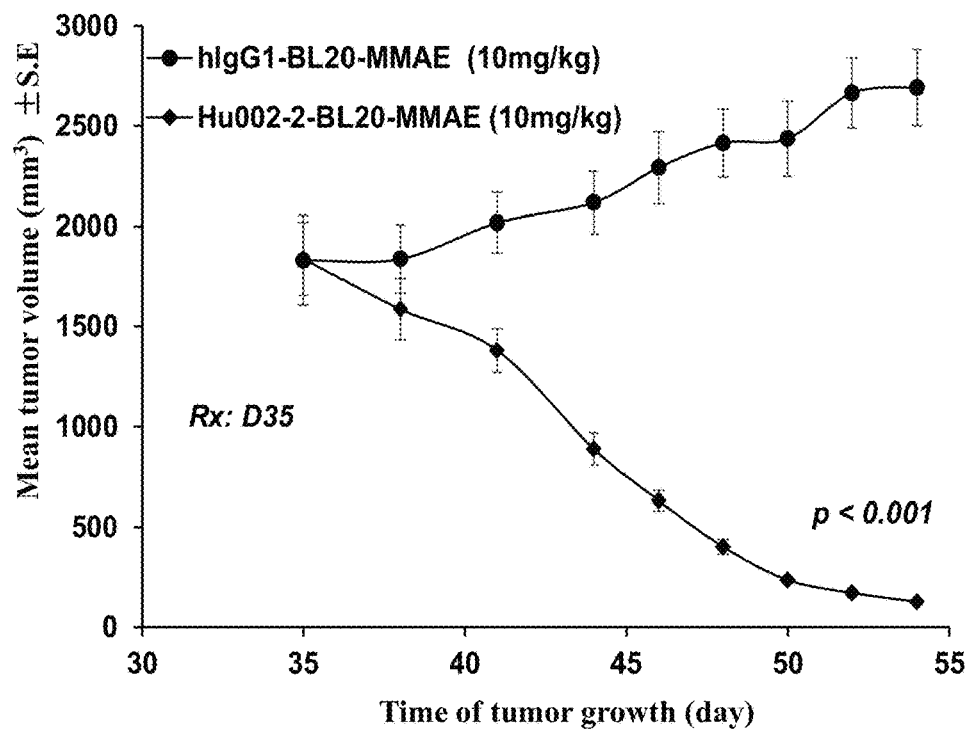
FIG. 48 shows that the humanized Hu002-2-BL20-MMAE (10 mg/kg; single dose) targeting LCLC-103H large tumors (1800 mm³ is the volume at the initial dose) can lead to a result of tumor regression.

The results are shown in FIG. 48. Similarly, when LCLC-103H tumor grew to a volume of 1800 $mm^3$ in vivo, a single dose of 10 mg/kg Hu002-2-BL20-MMAE was administered, and the tumor regression rate was >90% on the 20th day of treatment.

Example 20 Determination of Binding Activities of Humanized AXL Antibody to Mouse AXL and Cynomolgus AXL 1. The full-length AXL protein sequence of monkey (Genebank ID: XP_014979499.1; 894 amino acids), and the full-length AXL protein sequence of mouse (Genebank ID: NP_033491.2; 888 amino acids) were used. The specific amino acid sequences were listed in SEQ ID NO: 39 and SEQ ID NO: 40, respectively.

2. The synthetic full-length gene sequences from cynomolgus monkey and mouse were constructed into mammalian expression vector pcDNA3.1, and the positive expression vector plasmids were prepared.

3. HEK293T cells were spread to a 50% density in a culture dish, and cultured overnight at 37° C. to a confluence of about 80%. 2 g of monkey/mouse-AXL vector plasmid prepared above was transiently transfected into the cells with Liposome Lipo2000 (Invitrogen). 24 hours after transfection, the proteins were collected for Western blot analysis, and the cells were collected for FACS to detect the binding activity of Hu002-2 and monkey/mouse AXL on HEK293T cell surface. The FACS detection test method may be referred to Example 18.

Figure 49:
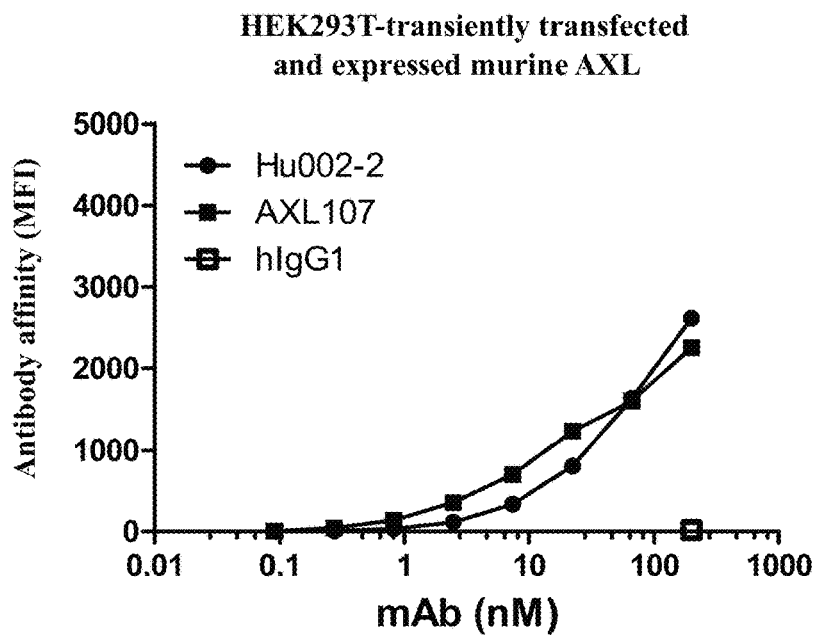
FIG. 49 shows the detection of FACS binding activity of Hu002-2 to HEK293T transiently transfected to express murine AXL protein; compared with human-derived AXL, Hu002-2 or AXL107 shows very weak binding activity to murine AXL.

The results are as shown in FIG. 49. The AXL humanized antibody Hu002-2 had similar effects to the control antibody AXL107, and had poor binding ability to mouse AXL on the surface of HEK-293T, and the binding saturation plateau was not reached at the highest antibody concentration (200 nM).

Figure 50:
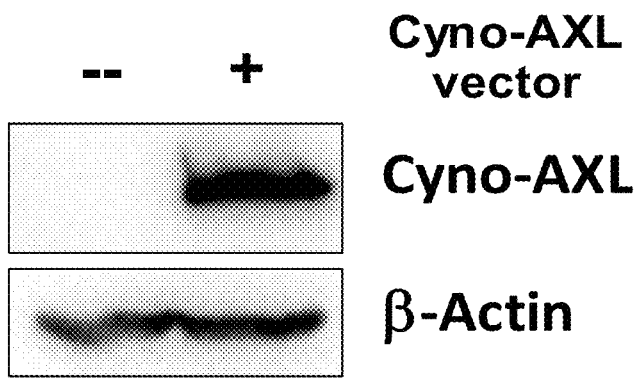
FIG. 50 shows the binding affinity of Hu002-2 to cynomolgus monkey AXL.
Figure 50:
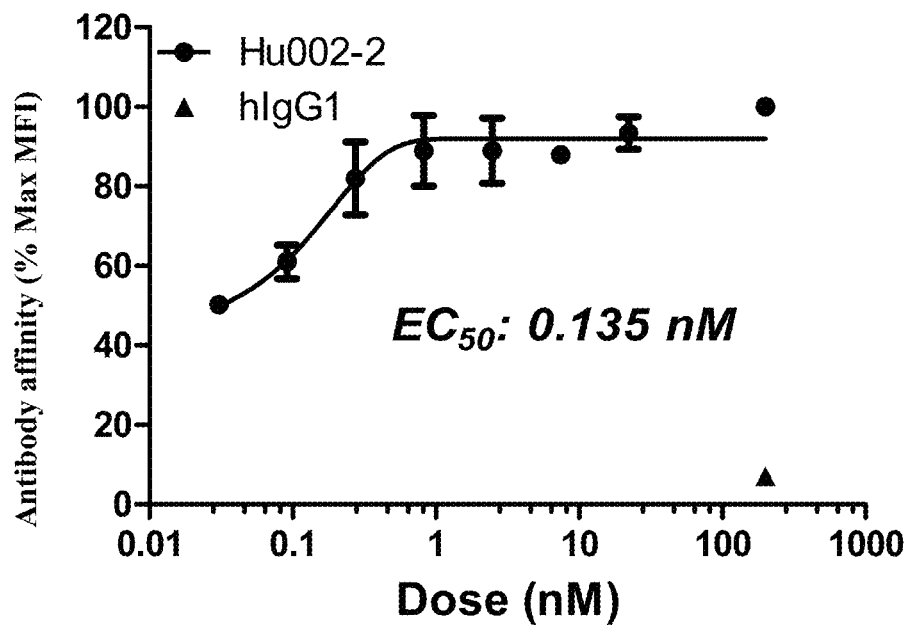

The results are shown in FIG. 50. The transient transfection efficiency of monkey AXL and the binding ability of humanized antibody Hu002-2 to it were proved by immunoblotting method (FIG. 50A). At the same time, FACS tests showed that Hu002-2 had excellent binding affinity to cynomolgus monkey AXL on the surface of HEK-293T cells, and the EC$_{50}$ was 0.135 nM (FIG. 50B). These results support the feasibility of using cynomolgus monkeys as preclinical models to evaluate toxicity, pharmacokinetics, and toxicities of Hu002 series antibodies.

Example 21 Comparison of the Antibody and Antibody-Drug Conjugate with the Prior Art The heavy chain and light chain variable region sequences (VH/VL) of AXL107 antibody disclosed in the invention patent application No. CN201580045131 were artificially synthesized and cloned into a vector comprising human IgG1 heavy chain constant region and Kappa chain constant region. The obtained vector was confirmed by sequencing, then expressed and purified in the FreeStyle™ 293T cell system to obtain AXL107 (Example 3), which was then prepared into an antibody-drug conjugate of AXL107 (Example 14). AXL107, AXL107-vc-MMAE, and AXL107-BL20-MMAE were added as reference drugs to the study of the present invention.

```
AXL107- Heavy Chain Variable Region (VH)
                                       SEQ ID NO. 37
EVQLLESGGGLVQPGGSLRLSCAASGFTFSSYAMNWVRQAPGKGLEWVST

TSGSGASTYYADSVKGRFTISRDNSKNTLYLQMNSLRAEDTAVYYC

AKIWIAFDIWGQGTMVTV
```

```
AXL107-Light Chain Variable Region (VL)
                                       SEQ ID NO. 38
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPYT

FGQGTKLEIK
```

The activity results of the comparison test are summarized as follows:
1. The results are shown in Table-3, Table-4, Table-5, Table-7 and Table-8. Compared with AXL107, the mAb005c of the present invention had comparable target affinity, while mAb002c and multiple antibodies in the humanized Hu002 series had a higher affinity to AXL in tumor cells, and higher tumor suppressor activity was expected.
2. The results are shown in Table-9 and Table-10. Based on their higher tumor cell affinities, mAb002c-vc-MMAE, mAb002c-BL20-MMAE, and the corresponding AXL-ADCs prepared by the humanized Hu002 antibody had shown stronger AXL-targeting specific anti-tumor effects in vitro.
3. The results are as shown in Table-11 (FIG. 41) and Table-13 (FIG. 46). Consistent with the results in vitro, multiple preferred humanized AXL-ADCs of the present invention had excellent anti-tumor effect in vivo, and their activities were better than that of the prior art AXL107-VC-MMAE.
4. The results are shown in FIG. 23 and FIG. 26. The mAb002c-BL20-MMAE had higher substance uniformity than that of the prior art AXL107-vc-MMAE (FIG. 17 and FIG. 20). The single distribution component (DAR4) account for more than 90%.
5. The therapeutic effects of BL20-MMAE linker and vc-MMA linker were directly compared in further efficacy tests for tumors in vivo, and the results showed that BL20-MMAE was more superior to vc-MMAE (FIG. 40 and Table-11).

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. An antibody, which binds to AXL, wherein the antibody comprises a heavy chain and a light chain, wherein the heavy chain has a heavy chain variable region comprising the following three complementarity determining regions or CDRs:
   CDR1 as shown in SEQ ID NO. 1,
   CDR2 as shown in SEQ ID NO. 2, and
   CDR3 as shown in SEQ ID NO. 3; and
   the light chain has a light chain variable region comprising the following three complementarity determining regions or CDRs:
   CDR1' as shown in SEQ ID NO. 4,
   CDR2' as shown in SEQ ID NO. 5, and
   CDR3' as shown in SEQ ID NO. 6;
or,
the heavy chain has a heavy chain variable region comprising the following three complementarity determining regions or CDRs:
   CDR1 as shown in SEQ ID NO. 9,
   CDR2 as shown in SEQ ID NO. 10, and
   CDR3 as shown in SEQ ID NO. 11; and
   the light chain has a light chain variable region comprising the following three complementarity determining regions or CDRs:
   CDR1' as shown in SEQ ID NO. 12,
   CDR2' as shown in SEQ ID NO. 13, and
   CDR3' as shown in SEQ ID NO. 14;
or,
the heavy chain has a heavy chain variable region comprising the following three complementarity determining regions or CDRs:

CDR1 as shown in SEQ ID NO. 17,
CDR2 as shown in SEQ ID NO. 18, and
CDR3 as shown in SEQ ID NO. 19; and
the light chain has a light chain variable region comprising the following three complementarity determining regions or CDRs:
CDR1' as shown in SEQ ID NO. 20,
CDR2' as shown in SEQ ID NO. 21, and
CDR3' as shown in SEQ ID NO. 22.

2. A recombinant protein which comprises:
(i) the antibody of claim 1; and
(ii) an optional tag sequence that assists expression and/or purification.

3. A CAR construct, wherein the scFv segment of the monoclonal antibody antigen binding region of the CAR construct is a binding region that specifically binds to AXL, and the scFv has a heavy chain variable region comprising the following three complementarity determining regions or CDRs:
CDR1 as shown in SEQ ID NO. 1,
CDR2 as shown in SEQ ID NO. 2, and
CDR3 as shown in SEQ ID NO. 3;
and a light chain variable region comprising the following three complementarity determining regions or CDRs:
CDR1' as shown in SEQ ID NO. 4,
CDR2' as shown in SEQ ID NO. 5, and
CDR3' as shown in SEQ ID NO. 6;
or,
the scFv has a heavy chain variable region comprising the following three complementarity determining regions or CDRs:
CDR1 as shown in SEQ ID NO. 9,
CDR2 as shown in SEQ ID NO. 10, and
CDR3 as shown in SEQ ID NO. 11; and
a light chain variable region comprising the following three complementarity determining regions or CDRs:
CDR1' as shown in SEQ ID NO. 12,
CDR2' as shown in SEQ ID NO. 13, and
CDR3' as shown in SEQ ID NO. 14;
or,
the scFv has a heavy chain variable region comprising the following three complementarity determining regions or CDRs:
CDR1 as shown in SEQ ID NO. 17,
CDR2 as shown in SEQ ID NO. 18, and
CDR3 as shown in SEQ ID NO. 19; and
a light chain variable region comprising the following three complementarity determining regions or CDRs:
CDR1' as shown in SEQ ID NO. 20,
CDR2' as shown in SEQ ID NO. 21, and
CDR3' as shown in SEQ ID NO. 22.

4. A recombinant immune cell expressing an exogenous CAR construct of claim 3.

5. An antibody-drug conjugate which comprises:
(a) the antibody of claim 1; and
(b) a coupling moiety coupled to the antibody moiety, and the coupling moiety is selected from the group consisting of a detectable label, a cytotoxic drug, a cytokine, a radionuclide, an enzyme, and a combination thereof.

6. The antibody of claim 1, wherein the heavy chain variable region has the amino acid sequence as shown in SEQ ID NO. 7, SEQ ID NO. 15, SEQ ID NO. 23, SEQ ID NO. 25, SEQ ID NO. 26, or SEQ ID NO. 27.

7. The antibody of claim 1, wherein the light chain variable region has the amino acid sequence as shown in SEQ ID NO. 8, SEQ ID NO. 16, SEQ ID NO. 24, SEQ ID NO. 28, SEQ ID NO. 29, SEQ ID NO. 30, SEQ ID NO. 31, SEQ ID NO. 32, SEQ ID NO. 33, SEQ ID NO. 34, or SEQ ID NO. 35.

8. The antibody of claim 1, wherein the antibody is selected from the group consisting of an animal-derived antibody, a chimeric antibody, a humanized antibody, and a combination thereof.

9. The an antibody-drug conjugate of claim 5, wherein the coupling moiety (D) is a cytotoxic drug, and the cytotoxic drug is a microtubule targeting drug and/or a DNA targeting drug and/or a topoisomerase inhibitor.

10. The an antibody-drug conjugate of claim 9, wherein the microtubule targeting drug is selected from the group consisting of: monomethyl auristatin E (MMAE), monomethyl auristatin F (MMAF), maytansine derivative DM1 and tubulysin; and/or
the DNA targeting drug is selected from the group consisting of docamycin, and pyrrolo[2,1-c][1,4]benzodiazepine (PBD); and/or
the topoisomerase inhibitor is selected from the group consisting of: 7-ethyl-10-hydroxycamptothecin (SN38), Exatecan and analogs thereof.

11. A method for treating AXL-related diseases, wherein the method comprises: administering the antibody of claim 1, an antibody-drug conjugate of the antibody, or a CAR-T cell expressing the antibody, and a combination thereof, to a subject in need.

12. The method of claim 11, wherein the AXL-related disease is selected from the group consisting of cancer, an autoimmune disease, a metabolism-related disease, an infectious disease, and a combination thereof.

13. The method of claim 11, wherein the cancer is a tumor with high AXL expression.

14. The antibody-drug conjugate of claim 5, wherein the antibody moiety is coupled to the coupling moiety via a chemical bond or a linker.

15. The antibody-drug conjugate of claim 5, wherein the linker is selected from the group consisting of 4-(N-maleimidomethyl)cyclohexane-1-carboxylic acid succinate (MCC), maleimidocaproyl (MC), 6-maleimidocaproyl-valine-citrulline-p-aminobenzyloxycarbonyl (mc-val-cit-PAB) and disubstituted maleimide linkers.

\* \* \* \* \*